US008058510B2

(12) United States Patent
Babiychuk et al.

(10) Patent No.: US 8,058,510 B2
(45) Date of Patent: **\*Nov. 15, 2011**

(54) METHOD AND MEANS TO MODULATE PROGRAMMED CELL DEATH IN EUKARYOTIC CELLS

(75) Inventors: Elena Babiychuk, Ghent (BE); Sergei Kushnir, Ghent (BE); Marc De Block, Merelbeke (BE)

(73) Assignee: Bayer Bioscience N.V., Gent (BE)

( * ) Notice: Subject to any disclaimer, the term of this patent is extended or adjusted under 35 U.S.C. 154(b) by 923 days.

This patent is subject to a terminal disclaimer.

(21) Appl. No.: 11/802,343

(22) Filed: May 22, 2007

(65) Prior Publication Data

US 2009/0205069 A1    Aug. 13, 2009

Related U.S. Application Data

(63) Continuation of application No. 10/705,197, filed on Nov. 12, 2003, now Pat. No. 7,241,936, which is a continuation of application No. 09/118,276, filed on Jul. 17, 1998, now Pat. No. 6,693,185.

(51) Int. Cl.
*C12N 15/82* (2006.01)
*A01H 5/00* (2006.01)
*A01H 5/10* (2006.01)

(52) U.S. Cl. ............... 800/285; 435/468; 435/320.1; 800/306; 800/320.1

(58) Field of Classification Search .................. None
See application file for complete search history.

(56) References Cited

U.S. PATENT DOCUMENTS

| | | | |
|---|---|---|---|
| 6,693,185 B2 | 2/2004 | Babiychuk et al. | |
| 7,241,936 B2 * | 7/2007 | Babiychuk et al. | 800/285 |
| 2001/0011381 A1 | 8/2001 | Babiychuk et al. | |

FOREIGN PATENT DOCUMENTS

| | | |
|---|---|---|
| WO | WO 97/06267 | 2/1997 |
| WO | WO 99/37789 | 7/1999 |

OTHER PUBLICATIONS

Bennet M.D. Plant genome values: how much do we know? Proc Natl Acad Sci U S A. Mar. 3, 1998;95(5):2011-6.*
Baulcombe D.C. RNA as a target and an initiator of post-transcriptional gene silencing in transgenic plants. Plant Mol Biol. Oct. 1996;32(1-2):79-88. Review.*
Kurland C.G. Codon bias and gene expression. FEBS Lett. Jul. 22, 1991;285(2):165-9.*
Thierry D. et al. Sequence homology requirements for transcriptional silencing of 35S transgenes and post-transcriptional silencing of nitrite reductase (trans)genes by the tobacco 271 locus. Plant Mol Biol. Dec. 1996;32(6):1075-83.*
Amor, Y. et al., The involvement of poly (ADP-ribose) polymerase in the oxidative stress responses in plants FEBS Letters, vol. 440, Nov. 1998, 1-7.
Bosher et al., "RNA Interference Can Target Pre-mRNA: Consequences for Gene Expression in a *Caenorhabditis elegans* Operon", Nov. 1999, Genetics vol. 153, 1245-1256.
Babiychuk, E. et al., Higher plants possess two structurally different poly (ADP-ribose) polymerases, The Plant Journal, vol. 15, No. 5, Sep. 1998, 635-645.
Babiychuck et al., GenBank database entry AJ222589, Higher Plants Possess Two Poly (ADP-ribose) Polymerases (Nov. 14, 1997).
Babiychuck et al., GenBank database entry AJ222588, Higher Plants Possess Two Poly (ADP-ribose) Polymerases (Nov. 14, 1997).
Boase et al., In Viro Cellular and Developmental Biology, vol. 34, 46-51, 1998.
Chen et al., Poly (ADP-ribose) polymerase in plant nuclei, Eur. J. Biochem. 224 (1994), 135-142.
du Murcia et al., Poly (ADP-ribose) polymerase: a molecular nicksensor, Trends Biochem. Sci., Elsevier Science Ltd., Apr. 1994, 172-176.
Ding et al., Deletion of Ploy (ADP-ribose) Polymerase by Antisense RNA Expression Results in a Delay in DNA Strand Break Rejoining, vol. 267, No. 18, The Journal of Biological Chemistry, Jun. 25, 1992, 12804-12812.
Ellis et al., Mechanisms and Functions of Cell Death, Annual Reviews Cell Biology, Jul. 1991, 663-698.
Fire et al. (Feb. 1998) Potent and specific genetic interference by double-stranded RNA in *Caenorhabditis elegans*. Nature 19(391): 806-811.
Heller et al., Inactivation of the Poly (ADP-ribose) Polymerase Gene Affects Oxygen Radical and Nitric Oxide Toxicity in Islet Cells, vol. 270, No. 19, The Journal of Biological Chemistry, May 12, 1995, 11176-11180.
Helliwell et al. (Aug. 2003) Constructs and methods for high-throughput gene silencing in plants. Methods 30(4): 289-95.
Ikejima et al., The Zinc Fingers of Human Poly (ADP-ribose) Polymerase Are Differentially Required for the Recognition of DNA Breaks and Nicks and the Consequent Enzyme Activation, vol. 265, No. 35, The Journal of Biological Chemistry, Dec. 15, 1990, 21907-21913.
Jeggo, P. A., DNA repair: PARP—another guardian angel?, Current Biology, vol. 8, No. 2, Jan. 1998, R49-R51.
Küpper et al., Inhibition of Poly(ADP-ribose)ation by overexpressing the Poly(ADP-ribose) Polymerase DNA-binding Domain in Mammalian Cells, vol. 268, No. 31, The Journal of Biological Chemistry, Nov. 5, 1990, 18721-18724.
Küepper, J. H. et al., Molecular genetic systems to study the role of poly(ADP-ribosyl)ation in the cellular response to DNA damage, Biochimie, vol. 77, No. 6, 1995, 450-455.
Lautier, D. et al., Molecular and biochemical features of poly (ADP-ribose) metabolism, Molecular and Cellular Biochemistry, vol. 122, No. 2, May 26, 1993, 171-193.
Lazebnik et al., Cleavage of poly (ADP-ribose) polymerase by a proteinase with properties like ICE, vol. 371, Nature, Sep. 1994, 346-347.

(Continued)

*Primary Examiner* — Cynthia Collins
(74) *Attorney, Agent, or Firm* — Hunton & Williams LLP

(57) ABSTRACT

The invention provides for the use of isolated polynucleotides encoding maize poly (ADP-ribose) polymerase (PARP) proteins to produce eukaryotic cells and organisms, particularly plant cells and plants, with modified programmed cell death. Eukaryotic cells and organisms particularly plant cells and plants, are provided wherein either in at least part of the cells, preferably selected cells, the programmed cell death (PCD) is provoked, or wherein, on the contrary, PCD of the cells or of at least part of the cells in an organism is inhibited, by modulation of the level or activity or PARP proteins in those cells.

35 Claims, 6 Drawing Sheets

OTHER PUBLICATIONS

Lepiniec et al., Characterization of an *Arabidopsis thaliana* cDNA homologue to animal poly (ADP-ribose) polymerase, Federation of European Biochemical Societies, 1995, vol. 364, 103-108.

Lepiniec et al., FEBS., 1995, vol. 364, 405-411.

Lindahl et al., Post-translational modification of poly (ADP-ribose) polymerase induced by DNA strand breaks, Trends Biochem. Sci. Elsevier Science Ltd., Apr. 1995, 405-411.

Mahajan et al., Purification and cDNA Cloning of Maize Poly (ADP)-Ribose Polymerase, Plant Physiol. (1998) 118: 895-905.

Ménissier de Murcia et al., Requirement of Poly (ADP-ribose) polymerase in recovery from DNA damage in mice and in cells, vol. 94, Proc. Natl. Acad. Sci., USA, Cell Biology, Jul. 1997, 7303-7307.

Molinete et al., Overproduction of the poly (ADP-ribose) polymerase DNA-binding domain blocks alkylation-induced DNA repair synthesis in mammalian cells, vol. 12, The EMBO Journal, 1993, 2109-2117.

O'Farrell, ADP-ribosylation reactions in plants, Biochemie 77, 1995, 486-491.

Pennell et al., Programmed Cell Death in Plants, vol. 9, The Plant Cell, Jul. 1997, 1157-1168.

Puchta et al., Induction of intrachromosomal homologous recombination in whole plants, The Plants Journal, 1995, 203-210.

Schreiber et al., The human poly (ADP-ribose) polymerase nuclear localization signal is a bipartite element functionally separate from DNA binding and catalytic activity, vol. 11, No. 9, The EMBO Journal, 1992, 3263-3269.

Shoji et al., Involvement of poly (ADP-ribose) synthesis in transdifferentiation of isolated mesophyll cells of *Zinnia elegans* into tracheary elements, Plant Cell Physiol., 1997, 36-43.

Smulson et al., Requirement for the expression of poly (ADP-ribose) polymerase during the early stages of differentiation of 3T3-L1 preadipocytes, as studied by antisense RNA induction, vol. 270, No. 1, The Journal of Biological Chemistry, Jan. 6, 1995, 119-127.

Wang et al., Apoptosis: a functional paradigm for programmed plant cell death induced by a host-selective phytotoxin and invoked during development, vol. 8, The Plant Cell, Mar. 1996, 375-391.

Wang et al., Mice lacking ADPRT and poly (ADP-ribosyl)ation develop normally but are susceptible to skin disease, Genes & Development, 1995, 509-520.

Wang et al., PARP is important for genomic stability but dispensable in apoptosis, Genes & Development, 1997, 2347-2358.

Wang et al. (Apr. 2002) Application of gene silencing in plants. Curr Opin Plant Biol 5(2): 146-150.

Willmitzer et al., Poly (ADP-ribose) Synthesis in Plants, ADP-Ribosylation Reactions, 1982, 241-252.

Zhang et al., Nitric oxide activation of poly (ADP-ribose) synthetase in neurotoxicity, vol. 263, Science, Feb. 4, 1994, 687-689.

\* cited by examiner

EDTKKEESKSKRKRNSSNDTYESNKLIAIGE

B

METHOD AND MEANS TO MODULATE PROGRAMMED CELL DEATH IN EUKARYOTIC CELLS

CROSS-REFERENCE TO RELATED APPLICATIONS

This application is a continuation of U.S. patent application Ser. No. 10/705,197, filed Nov. 12, 2003, now U.S. Pat. No. 7,241,936, which is a continuation of U.S. patent application Ser. No. 09/118,276, filed Jul. 17, 1998, now U.S. Pat. No. 6,693,185, the disclosures of each of which are hereby incorporated by reference.

FIELD OF THE INVENTION

The invention relates to the use of poly (ADP-ribose) polymerase (PARP) proteins, particularly mutant PARP proteins or parts thereof, and genes encoding the same, to produce eukaryotic cells and organisms, particularly plant cells and plants, with modified programmed cell death. Eukaryotic cells and organism, particularly plant cells and plants, are provided wherein either in at least part of the cells, preferably selected cells, the programmed cell death (PCD) is provoked, or wherein, on the contrary, PCD of the cells or of at least part of the cells in an organism is inhibited, by modulation of the level or activity of PARP proteins in those cells. The invention also relates to eukaryotic cells and organisms, particularly plant cells and plants, expressing such genes.

DESCRIPTION OF RELATED ART

Programmed cell death (PCD) is a physiological cell death process involved in the elimination of selected cells both in animals and in plants during developmental processes or in response to environmental cues (for a review see Ellis et al. 1991; Pennell and Lamb, 1997). The disassembly of cells undergoing PCD is morphologically accompanied by condensation, shrinkage and fragmentation of the cytoplasm and nucleus, often into small sealed packets (Cohen 1993, Wang at al. 1996). Biochemically, PCD is characterized by fragmentation of the nuclear DNA into generally about 50 kb fragments representing oligonucleosomes, as well as the induction of cysteine proteinases and endonucleases. The fragmentation of the DNA can be detected by terminal deoxy-nucleotidyl transferase-mediated dUTP nick end labeling (TUNEL) of DNA 3'-OH groups in sections of cells. (Gavrieli et al. 1992). Cell death by PCD is clearly distinct from cell death by necrosis, the latter involving cell swelling, lysis and leakage of the cell contents.

In animals, PCD is involved in the elimination or death of unwanted cells such as tadpole tail cells at metamorphosis, cells between developing digits in vertebrates, overproduced vertebrate neurons, cells during cell specialization such as keratocytes etc. Damaged cells, which are no longer able to function properly, can also be eliminated by PCD, preventing them from multiplying and/or spreading. PCD, or the lack thereof, has also been involved in a number of pathological conditions in humans (AIDS, Alzheimer's disease, Huntington's disease, Lou Gehring's disease, cancers).

In plants, PCD has been demonstrated or is believed to be involved in a number of developmental processes such as e.g., removal of the suspensor cells during the development of an embryo, the elimination of aleurone cells after germination of monocotyledonous seeds; the elimination of the root cap cells after seed germination and seedling growth; cell death during cell specialization as seen in development of xylem tracheary element or trichomes, or floral organ aborting in, unisexual flowers. Also the formation of aerochyma in roots under hypoxic conditions and the formation of leaf lobes or perforations in some plants seem to involve PCD. Large scale cell death in plants occurs during upon senescence of leaves or other organs. The hypersensitive response in plants, in other words the rapid cell death occurring at the site of entry of an avirulent pathogen leading to a restricted lesion, is an another example of PCD in response to an environmental cue.

Animal or plant cells dying in suspension cultures, particularly in low-density cell suspension cultures, also demonstrate the characteristics of PCD.

An enzyme which has been implied to be involved in PCD or apoptosis is poly(ADP-ribose) polymerase. Poly(ADP-ribose) polymerase (PARP), also known as poly(ADP-ribose) transferase (ADPRT) (EC 2.4.2.30), is a nuclear enzyme found in most eukaryotes, including vertebrates, arthropods, molluscs, slime moulds, dinoflagellates, fungi and other low eukaryotes with the exception of yeast. The enzymatic activity has also been demonstrated in a number of plants (Payne et al., 1976; Willmitzer and Wagner, 1982; Chen et al., 1994; O'Farrell, 1995).

PARP catalyzes the transfer of an ADP-ribose moiety derived from $NAD^+$, mainly to the carboxyl group of a glutamic acid residue in the target protein, and subsequent ADP-ribose polymerization. The major target protein is PARP itself, but also histones, high mobility group chromosomal proteins, a topoisomerase, endonucleases and DNA polymerases have been shown to be subject to this modification.

The PARP protein from animals is a nuclear protein of 113-120 kDa, abundant in most cell types, that consist of three major functional domains: an amino-terminal DNA-binding domain containing two Zn-finger domains, a carboxy-terminal catalytic domain, and an internal domain which is automodified (de Murcia and Ménissier de Murcia, 1994; Kameshita et al., 1984; Lindahl et al., 1995). The enzymatic activity in vitro is greatly increased upon binding to single-strand breaks in DNA. The in vivo activity is induced by conditions that eventually result in DNA breaks (Alvarez-Gonzalez and Althaus, 1989; Ikejima et al., 1990). Automodification of the central domain apparently serves as a negative feedback regulation of PARP.

PARP activity in plant cells was first demonstrated by examining the incorporation of $^3H$ from labelled $NAD^+$ into the nuclei of root tip cells (Payne et al., 1976; Willmitzer and Wagner, 1982). The enzymatic activity was also partially purified from maize seedlings and found to be associated with a protein of an apparent molecular mass of 113 kDa, suggesting that the plant PARP might be similar to the enzyme from animals (Chen et al., 1994; O'Farrell, 1995).

cDNAs corresponding to PARP proteins have isolated from several species including mammals, chicken, Xenopus, insects and Caenorhabditis elegans.

Chen et al. (1994) have reported PARP activity in maize nuclei and associated this enzymatic activity with the presence of an approximately 114 kDa protein present in an extract of maize nuclei. O'Farrel (1995) reported that RT-PCR-amplification on RNA isolated from maize (using degenerate primers based on the most highly conserved sequences) resulted in a 300 bp fragment, showing 60% identity at the amino acid level with the human PARP protein. Lepiniec et al (1995) have isolated and cloned a full length cDNA from Arabidopsis thaliana encoding a 72 kDa protein with high similarity to the catalytic domain of vertebrate PARP. The N-terminal domain of the protein does not reveal any sequence similarity with the corresponding domain of PARP from vertebrates but is composed of four stretches of amino acids (named A1, A2, B and C) showing similarity to the N-terminus of a number of nuclear and DNA binding proteins. The predicted secondary structure of A1 and A2 was a helix-loop-helix structure.

The Genbank database contains the sequences of two cDNAS from *Zea mays* for which the amino acid sequence of the translation products has either homology to the conventional PARP proteins (AJ222589) or to the non-conventional PARP proteins, as identified in *Arabidopsis* (AJ222588)

The function(s) of PARP and poly-ADP ribosylation in eukaryotic cells is (are) not completely clear. PARP is involved or believed to be involved either directly or indirectly in a number of cellular processes such as DNA repair, replication and recombination, in cell division and cell differentiation or in the signalling pathways that sense alterations in the integrity of the genome. As PARP activity may significantly reduce the cellular $NAD^+$ pool, it has also been suggested that the enzyme may play a critical role in programmed cell death (Heller et al., 1995; Zhang et al., 1994). Further, it has been suggested that nicotinamide resulting from $NAD^+$ hydrolysis or the products of the turn-over of poly-ADP-ribose by poly-ADP-ribose glycohydrolase may be stress response signals in eukaryotes.

The information currently available on the biological function of plant PARP has come from experiments involving PARP inhibitors suggesting an in vivo role in the prevention of homologous recombination at sites of DNA damage as rates of homologous intrachromosomal recombination in tobacco are increased after application of 3-aminobenzamide (3ABA) (Puchta et al., 1995). Furthermore, application of PARP inhibitors, such as 3ABA, nicotinamide, and 6(5H)-phenasthridinone, to differentiating cells of Zinnia or of *Helianthus tuberosum* has been shown to prevent development of tracheary elements (Hawkins and Phillips, 1983; Phillips and Hawkins, 1985; Shoji et al., 1997; Sugiyama et al., 1995), which is considered to be an example of programmed cell death in plants.

PCT application WO97/06267 describes the use of PARP inhibitors to improve the transformation (qualitatively or quantitatively) of eukaryotic cells, particularly plant cells.

Lazebnik et al. (1994) identified a protease with properties similar to the interleukin 1-β-converting enzyme capable of cleaving PARP, which is an early event in apoptosis of animal cells.

Kuepper et al. (1990) and Molinette et al. (1993) have described the overproduction of the 46 kDa human PARP DNA-binding domain and various mutant forms thereof, in transfected CV-1 monkey cells or human fibroblasts and have demonstrated the trans-dominant inhibition of resident PARP activity and the consequent block of base excision DNA repair in these cells.

Ding et al. (1992), and Smulson et al. (1995) have described depletion of PARP by antisense RNA expression in mammalian cells and observed a delay in DNA strand break joining, and inhibition of differentiation of 3T3-L1 preadipocytes.

Ménissier de Murcia et al., (1997) and Wang et al. (1995, 1997) have generated transgenic "knock-out" mice mutated in the PARP gene, indicating that PARP is not an essential protein. Cells of PARP-deficient mice are, however, more sensitive to DNA damage and differ from normal cells of animals in some aspects of induced cell death (Heller et al., 1995).

SUMMARY AND OBJECTS OF THE INVENTION

The invention provides a method for modulating programmed cell death in a eukaryotic cell, comprising reducing the functional level of the total PARP activity in a eukaryotic cell using the nucleotide sequence of a PARP gene of the ZAP class, and the nucleotide sequence of a PARP gene of the NAP class, preferably to reduce expression of the endogeneous PARP genes, to reduce the apparent activity of the proteins encoded by the endogenous PARP genes or to alter the nucleotide sequence of the endogenous PARP genes.

The invention also provides a method for modulating programmed cell death in a eukaryotic cell, comprising introducing a first and a second PCD modulating chimeric gene in a eukaryotic cell, preferably a plant cell, wherein the first PCD modulating chimeric gene comprises the following operably linked DNA regions: a promoter, operative in a eukaryotic cell; a DNA region, which when transcribed yields a RNA molecule which is either capable of reducing the functional level of a Zn-finger containing PARP protein of the ZAP class; or is capable of being translated into a peptide or protein which when expressed reduces the functional level of a PARP protein of ZAP class and a DNA region involved in transcription termination and polyadenylation and wherein the second PCD modulating chimeric gene comprises the following operably linked DNA regions: a promoter, operative in the eukaryotic cell; a DNA region, which when transcribed yields a RNA molecule which is either capable of reducing the functional level of a PARP protein of the NAP class; or capable of being translated into a peptide or protein which when expressed reduces the functional level of a PARP protein of the NAP class, and a DNA region involved in transcription termination and polyadenylation; and wherein the total apparent PARP activity in the eukaryotic cell is reduced significantly, (preferably the total apparent PARP activity is reduced from about 75% to about 90% of the normal apparent PARP activity in the eukaryotic cell, and the eukaryotic cell is protected against programmed cell death) or almost completely (preferably the total apparent PARP activity is reduced from about 90% to about 100% of the normal apparent PARP activity in the eukaryotic cell, and the cell is killed by programmed cell death).

Preferably the first transcribed DNA region or the second transcribed DNA region or both, comprise a nucleotide sequence of at least about 100 nucleotides with 75% identity to the sense DNA strand of an endogenous PARP gene of the ZAP or the NAP class, and encode a sense RNA molecule is capable of reducing the expression of the endogenous PARP gene of the ZAP or the NAP class.

In an alternative method for modulating programmed cell death, provided by the invention, the first transcribed DNA region or the second transcribed DNA region or both, comprise a nucleotide sequence of at least about 100 nucleotides with 75% identity to the complement of the sense DNA strand of an endogenous PARP gene of the ZAP or the NAP class, and encode RNA molecule is capable of reducing the expression of said endogenous PARP gene of the ZAP or the NAP class.

In yet an alternative method for modulating programmed cell death, provided by the invention, the first and/or second transcribed DNA region encodes a RNA molecule comprising a sense nucleotide sequence of at least about 100 nucleotides with 75% identity to the mRNA resulting from transcription of an endogenous PARP gene of the ZAP or the NAP class and the RNA molecule further comprising an antisense nucleotide sequence of at least about 100 nucleotides with 75% identity to the complement of the mRNA resulting from transcription of the endogenous PARP gene of the ZAP or the NAP class, wherein the sense and antisense nucleotide sequence are capable of forming a double stranded RNA region, and wherein that RNA molecule is capable of reducing the expression of the endogenous PARP gene of the ZAP or the NAP class.

In a further alternative method for modulating programmed cell death, provided by the invention, the first and/or second transcribed DNA region encodes a dominant negative PARP mutant capable of reducing the apparent activity of the PARP protein encoded by an endogenous PARP gene of the ZAP or the NAP class, preferably comprising amino acid sequence selected from the amino acid sequence of SEQ ID No 4 from amino acid 1 to 159 or the amino acid sequence of SEQ ID No 6 from amino acid 1 to 138 or comprising an amino acid sequence selected from the amino acid sequence of SEQ ID No 2 from amino acid 1 to 370, the amino acid sequence of SEQ ID No 11 from amino acid 1 to 98, or the amino acid sequence of SEQ ID No 2 from amino acid 1 to 370 wherein the amino acid sequence from amino acid 1 to 88 is replaced by the amino acid sequence of SEQ ID No 11.

The promoter of the first and second chimeric PCD modulating genes, or both, may be a tissue specific or inducible promoter such as a promoter is selected from a fungus-responsive promoter, a nematode-responsive promoter, an anther-selective promoter, a stigma-selective promoter, a dehiscence-zone selective promoter.

The invention also provides a method for modulating programmed cell death in a plant cell, comprising introduction of a PCD modulating chimeric gene in said plant cell, wherein the PCD modulating chimeric gene comprises the following operably linked DNA regions: a plant-expressible promoter, a DNA region, which when transcribed yields a RNA molecule, which is either capable of reducing the expression of endogenous PARP genes; or is capable of being translated into a peptide or protein which when expressed reduces the apparent PARP activity in the plant cell, and a DNA region involved in transcription termination and polyadenylation, wherein the total apparent PARP activity in the plant cell is reduced from about 75% to about 100% of the normal apparent PARP activity in the plant cell.

It is another objective of the invention to provide the first and second chimeric PCD modulating gene as well as a eucaryotic cell, particularly a plant cell comprising the first and second chimeric PCD modulating gene and non-human eukaryotic organisms, particularly plants comprising such cells.

Finally, the invention also provides an isolated DNA sequence comprising the nucleotide sequence of SEQ ID No 1 from the nucleotide at position 113 to the nucleotide at position 3022, an isolated DNA sequence comprising the nucleotide sequence of SEQ ID No 10 from the nucleotide at position 81 to the nucleotide at position 3020 and an isolated DNA sequence comprising the nucleotide sequence of SEQ ID No 3 from the nucleotide at position 107 to the nucleotide at position 2068.

(A) Alignment of the sequences upstream of the $NAD^+$-binding domain found in *Arabidopsis thaliana* APP (A.th. APP; EMBL accession number Z48243; SEQ ID No 6) and the maize homolog NAP (Z.m. NAP; EMBL accession number AJ222588; SEQ ID No 4). The domain division shown is as previously proposed (Lepiniec et al., 1995). The nuclear localization signal (NLS) located in the B domain is indicated by the bracket. The sequence of the B domain is not very well conserved between dicotyledonous and monocotyledonous plants. The C domain is probably comparable in function to the automodification domain of PARP from animals. The imperfect repeats, A1 and A2, are also present in maize NAP. To illustrate the internally imperfect two-fold symmetry within the repeat sequence, the properties of amino acid residues are highlighted below the sequences as follows: filled-in circles, hydrophobic residue; open circle, glycine; (+), positively charged residue; (−), negatively charged residue; wavy line, any residue. The axis of symmetry is indicated by the vertical arrowhead and arrowhead lines mark the regions with the inverted repetition of amino acid side chain properties.

(B) Alignment of the DNA-binding and auto-catalytic domains of mouse PARP and maize ZAP. Zn-finger-containing maize ZAP1 and ZAP2 (partial cDNA found by the 5'RACE PCR analysis) are indicated as Z.m. ZAP (EMBL accession number AJ222589; SEQ ID No 2) and Z.m. ZAP (race) (SEQ ID No 11 from amino acid at position 1 to amino acid at position 98), respectively, and the mouse PARP, M.m. ADPRT (Swissprot accession number P11103). The Zn-fingers and bipartite NLS of the mouse enzyme are indicated by brackets, the Caspase 3 cleavage site by the asterisk, and the putative NLS in the ZAP protein by the bracket in bold below the maize sequence. The amino acid residues that are conserved in all sequences are boxed; amino acid residues with similar physicochemical properties are shaded with the uppermost sequence as a reference.

Figure 1:
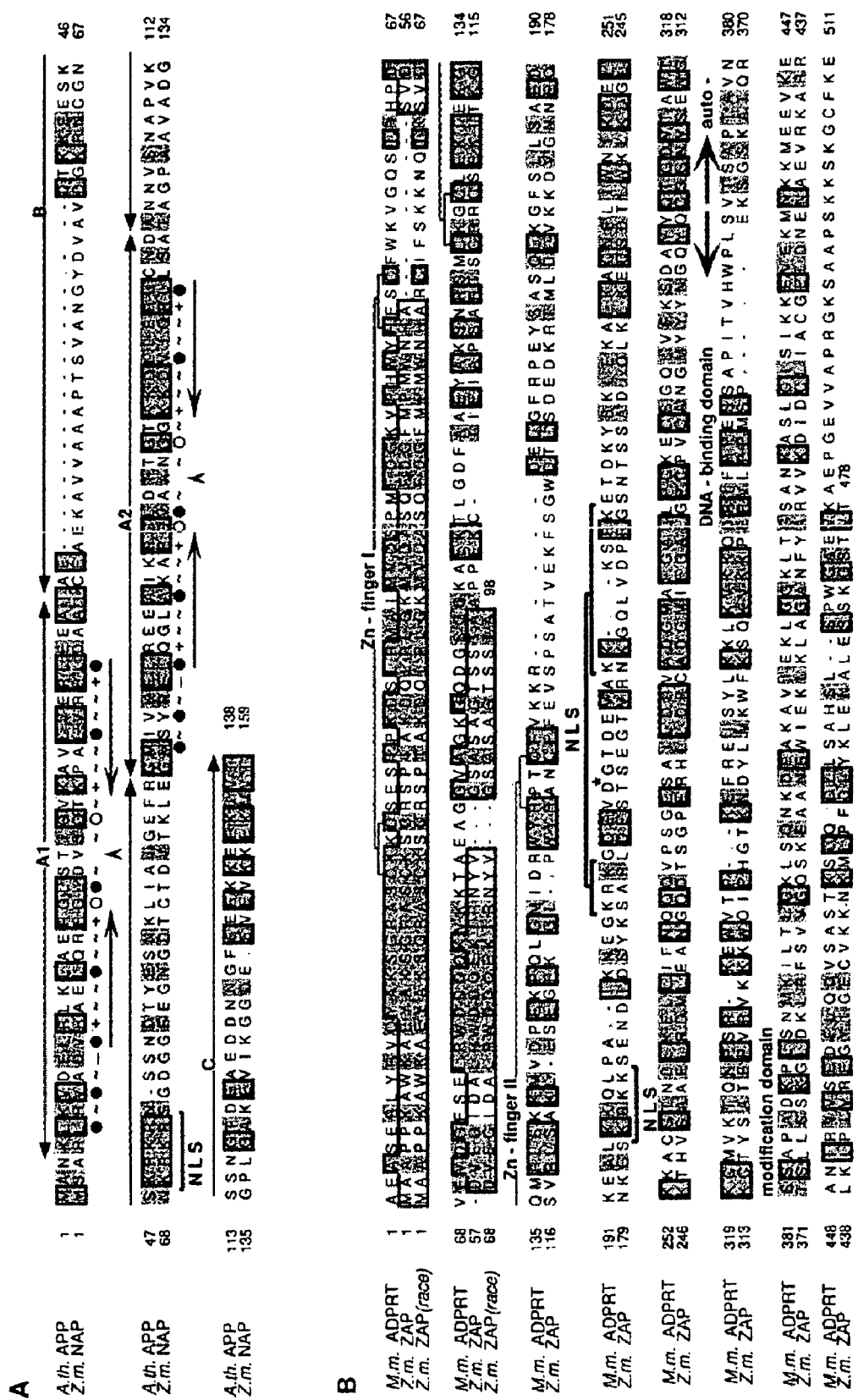
FIG. 1. The deduced N-terminal amino acid sequences of plant poly(ADP-ribose) polymerases.
Figure 2:
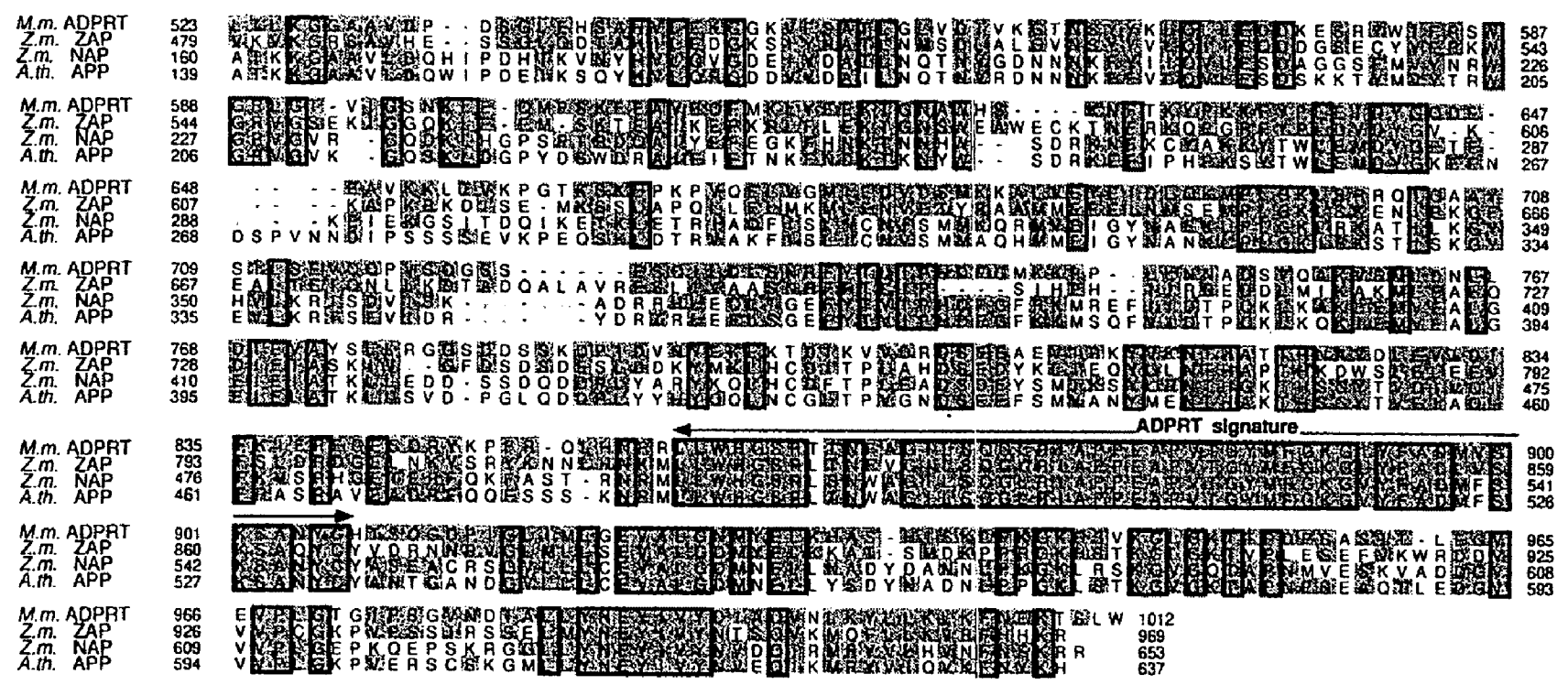

FIG. 2. Comparison of the NAD+-binding domain of mouse PARP and plant PARP proteins. The range of the "PARP signature" is indicated above the sequences. Names and sequence alignment are as in FIG. 1.

Figure 3:
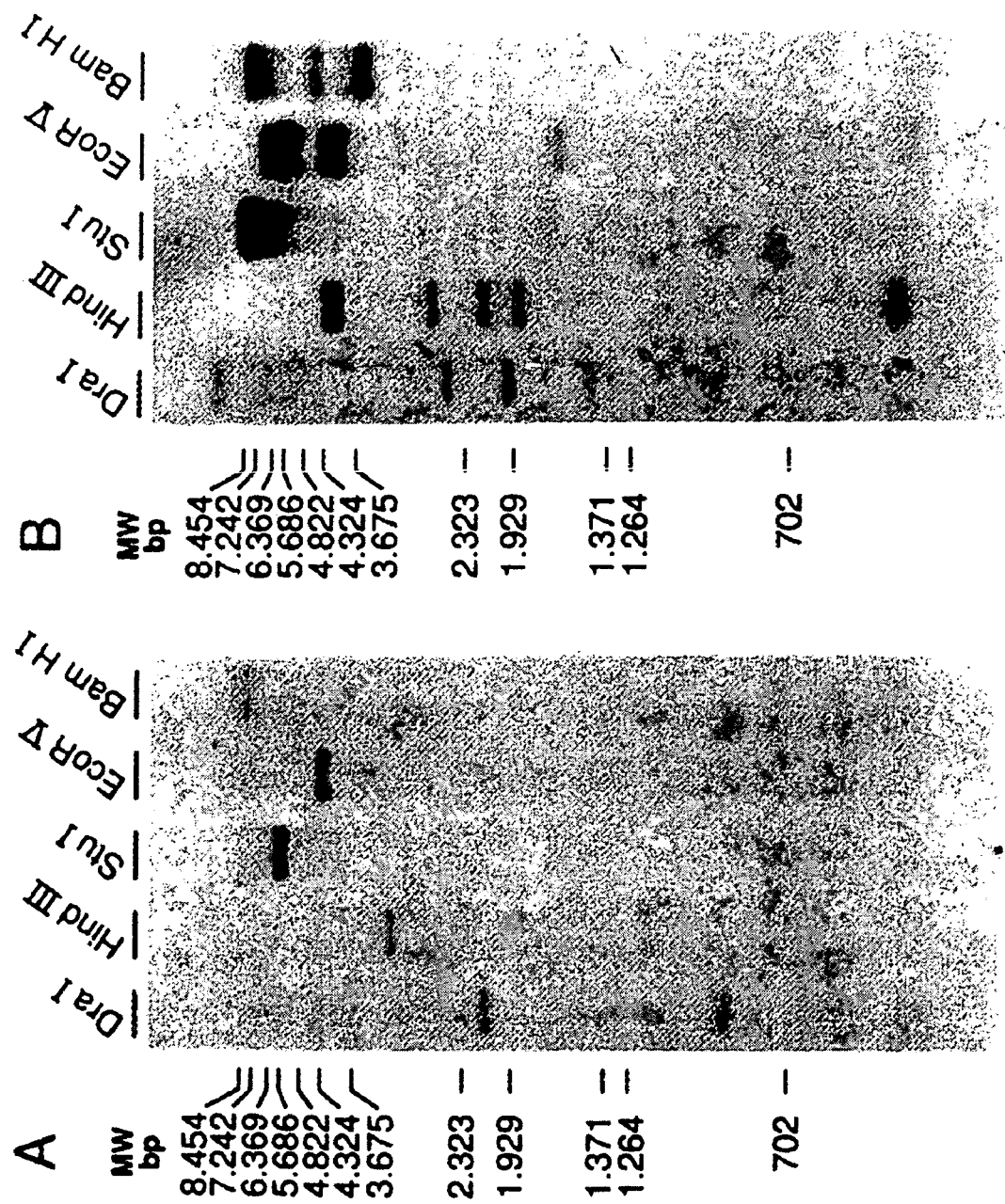

FIG. 3. Estimation of the gene copy number and transcript size for the nap and zap genes.

(A) and (B) Maize genomic DNA of variety LG2080 digested with the indicated restriction endonucleases, resolved by agarose gel electrophoresis, blotted, and hybridized with radioactively labelled DNA probes prepared from the 5' domains of the nap and zap cDNA, which do not encode the $NAD^+$-binding domain. The hybridization pattern obtained with the nap probe (A) is simple and indicates a single nap gene in: the maize genome. As can be seen from the hybridization pattern (B), there might be at least two zap genes. To determine the size of the transcripts encoded by the zap and nap genes, approximately 1 μg of poly(A)+ RNA extracted from roots (lane 1) and shoots (lane 2) of 6-day-old seedlings were resolved on an agarose gel after denaturation with glyoxal, blotted, and hybridized with nap (C) and zap (D) $^{32}P$-labelled cDNA. $^{33}P$ 5' end-labelled BstEII fragments of λDNA were used as a molecular weight markers in both DNA and RNA gel blot experiments; their positions are indicated in kb to the left of each panel.

Figure 4:
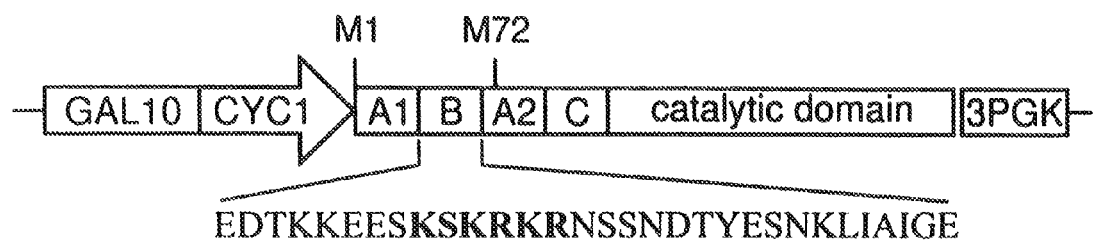
Figure 4:
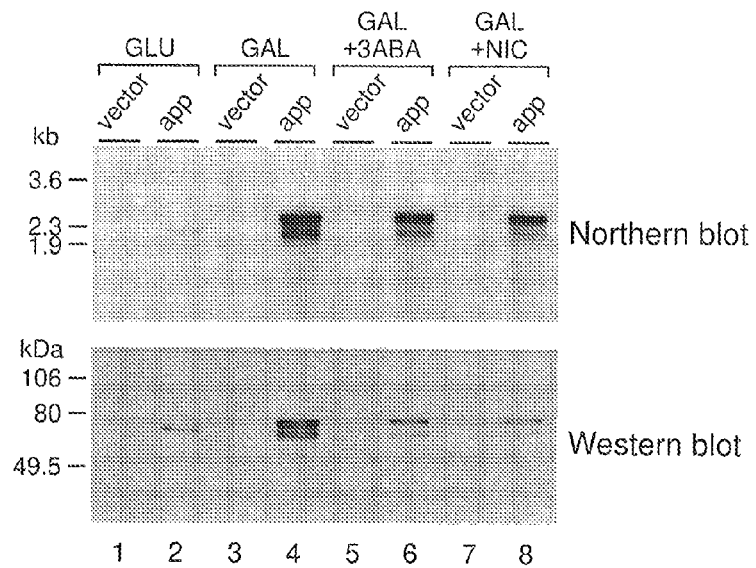

FIG. 4. Analysis of APP expression in yeast.

(A) Schematic drawing of the expression cassette in pV8SPA. The expression of the app cDNA is driven by a chimeric yeast promoter, which consists of the minimal TATA box-containing promoter region of the cyc1 gene (CYCL) and an upstream activating promoter region of the gal10 gene (GAL10), the latter providing promoter activation by galactose. Downstream regulatory sequences are derived from the gene encoding phosphoglycerol kinase (3PGK) (Kuge and Jones, 1994). The app-coding region is drawn with a division in putative domains as proposed earlier (Lepiniec et al., 1995): A1 and A2 correspond to imperfect 27-amino acid repeats, in between which there is a sequence (B domain), rich in positively charged amino acids and resembling the DNA-binding domains of a number of DNA-binding proteins. The amino acid sequence of the B domain is shown below the map and the stretch of arginine and lysine residues, which may function as an NLS is drawn in bold. Methionine residues ($M^1$, $M^{72}$), which may function as translation initiation codons, are indicated above the map. The C domain is rich in glutamic acid residues, resembling in its composition, but not in its sequence, the auto-modification domain of PARP from animals.

(B) Immunoblot (Western blot) and Northern blot analyses of the DY (pYeDP1/8-2) and DY(pV8SPA) strains, indicated as (vector) and (app), respectively. Strains were grown in SDC medium supplemented with glucose (GLU), galactose (GAL), galactose and 3 mM of 3ABA (GAL+3ABA), or galactose and 5 mM nicotinamide (GAL+NIC). Total RNA or total protein were extracted from the same cultures. Ten micrograms of total protein were fractionated by electrophoresis on 10% SDS-PAGE, electroblotted, and probed with anti-APP antisera. Five micrograms of total RNA were resolved by electrophoresis on an 1.5% agarose gel, blotted onto nylon membranes, and hybridized with $^{32}$P-labeled DNA fragments derived from the app cDNA. Positions of the molecular weight marker bands are indicated to the left in kilobases (kb) and kilodalton (kDa).

Figure 5:
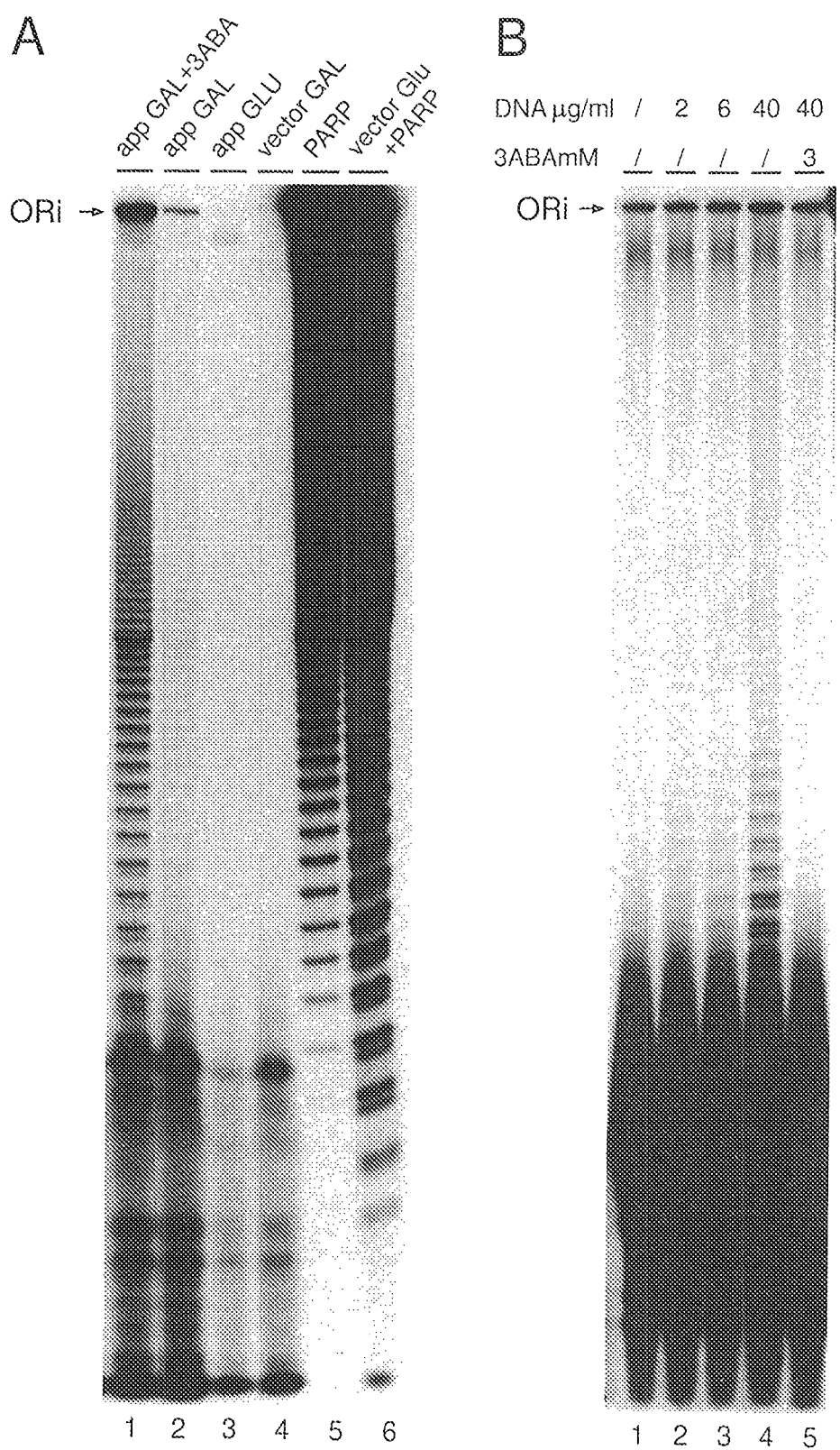

FIG. 5. Poly(ADP-ribose) polymerase activity of the APP protein.
(A) The total protein extracts were prepared from DY(pYeDP1/8-2) grown on SDC with 2% galactose (vector GAL) and DY(pV8SPA) grown either on SDC with 2% glucose (app GLU), on SDC with 2% galactose (app GAL), or on SDC with 2% galactose and 3 mM 3ABA (app GAL+3ABA). To detect the synthesis of the poly(ADP-ribose) in these extracts, samples were incubated with $^{32}$P-NAD$^+$ for 40 min at room temperature. Two control reactions were performed: 100 ng of the purified human PARP were incubated either in a reaction buffer alone (PARP) (lane 5), or with protein extract made from DY(pYeDP1/8-2) culture grown on glucose (vector GLU+PARP) (lane 6). The autoradiograph obtained after exposure of the dried gel to X-Omat Kodak film is shown. ORi corresponds to the beginning of the sequencing gel.
(B) Stimulation of poly(ADP-ribose) synthesis by DNA in protein extracts from DY(pV8SPA). Amounts of sonicated salmon sperm DNA added to the nucleic acid depleted yeast extracts are indicated in µg ml$^{-1}$. The synthesis of the poly(ADP-ribose) is blocked by 3ABA, which was added in one of the reactions at a concentration of 3 mM (lane 5). To ensure the maximal recovery of the poly(ADP-ribose), 20 µg of glycogen were included as a carrier during precipitation steps; this, as can be seen, however resulted in high carry-over of the unincorporated label.

Figure 6:
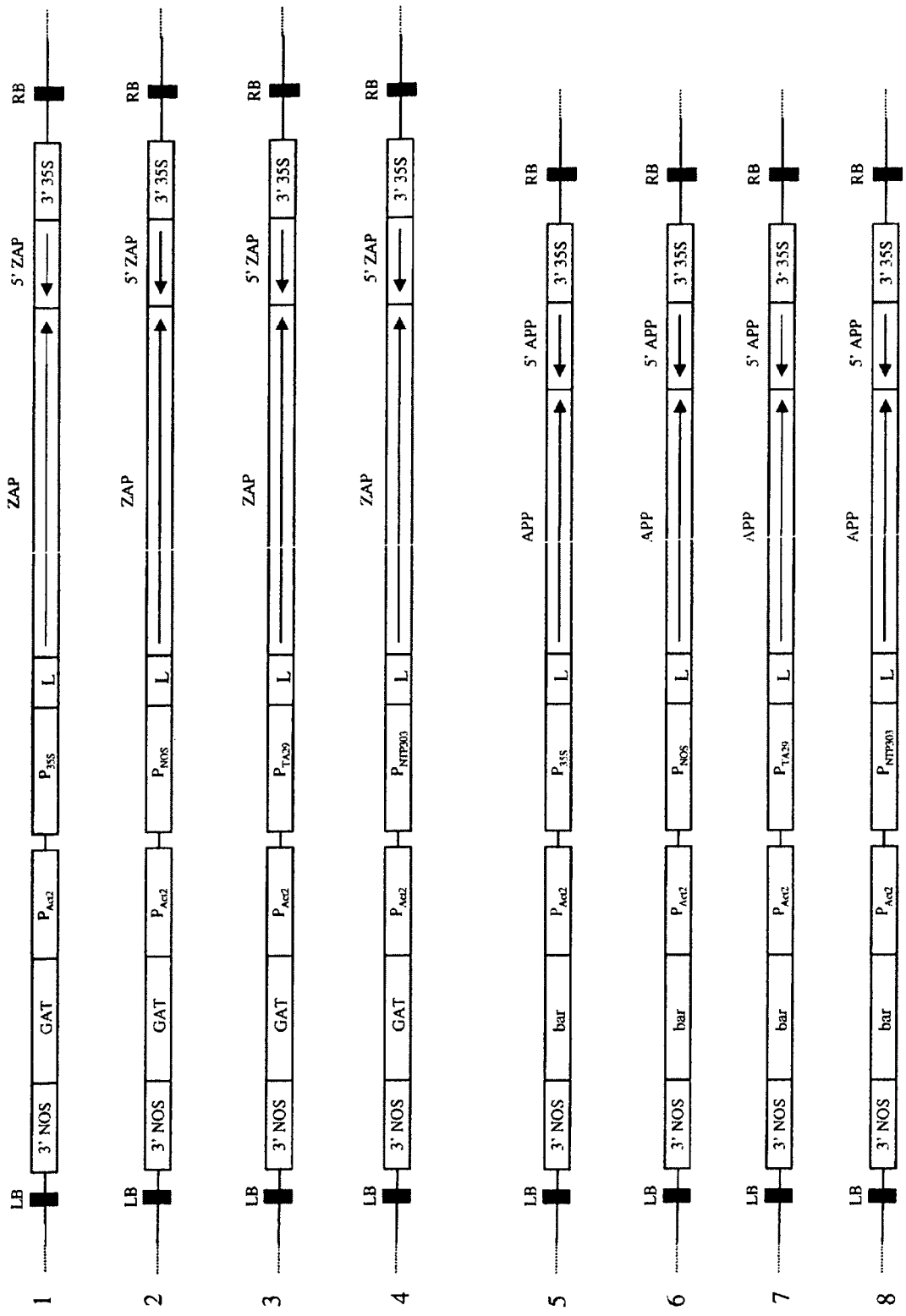

FIG. 6. Schematic representation of the T-DNA vectors comprising the PCD modulating chimeric genes of the invention. P35S: CaMV35S promoter; L: cab22 leader; ZAP; coding region of a PARP gene of the ZAP class; 5'AAP: N-terminal part of the coding regon of a PARP gene of the ZAP class in inverted orientation; 3' 35S: CaMV35S 3' end transcription termination signal and polyadenylation signal; pACT2: promoter region of the actin gene; pNOS; nopaline synthase gene promoter; gat: gentamycin acetyl transferase; bar: phosphinotricin acetyl transferase; 3'NOS: 3' end transcription termination signal and polyadenylation signal of nopaline synthase gene; APP: coding region of a PARP gene of the NAP class; 5'APP: N-terminal part of the coding regon of a PARP gene of the NAP class in inverted orientation; LB: left T-DNA border; RB: right T-DNA border; pTA29: tapetum specific promoter, pNTP303: pollen specific promoter.

DETAILED DESCRIPTION OF PREFERRED EMBODIMENTS

For the purpose of the invention, the term "plant-expressible promoter" means a promoter which is capable of driving transcription in a plant cell. This includes any promoter of plant origin, but also any promoter of non-plant origin which is capable of directing transcription in a plant cell, e.g., certain promoters of viral or bacterial origin such as the CaMV35S or the T-DNA gene promoters.

The term "expression of a gene" refers to the process wherein a DNA region under control of regulatory regions, particularly the promoter, is transcribed into an RNA which is biologically active i.e., which is either capable of interaction with another nucleic acid or protein or which is capable of being translated into a biologically active polypeptide or protein. A gene is said to encode an RNA when the end product of the expression of the gene is biologically active RNA, such as e.g. an antisense RNA or a ribozyme. A gene is said to encode a protein when the end product of the expression of the gene is a biologically active protein or polypeptide.

The term "gene" means any DNA fragment comprising a DNA region (the "transcribed DNA region") that is transcribed into a RNA molecule (e.g., a mRNA) in a cell under control of suitable regulatory regions, e.g., a plant-expressible promoter. A gene may thus comprise several operably linked DNA fragments such as a promoter, a 5' leader sequence, a coding region, and a 3' region comprising a polyadenylation site. An endogenous plant gene is a gene which is naturally found in a plant species. A chimeric gene is any gene which is not normally found in a plant species or, alternatively, any gene in which the promoter is not associated in nature with part or all of the transcribed DNA region or with at least one other regulatory regions of the gene.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

The invention is based on the one hand on the finding that eukaryotic cells, particularly plant cells, quite particularly Zea mays cells contain simultaneously at least two functional major PARP protein isoforms (classes) which differ in size and amino-acid sequence, yet are both capable of binding DNA, particularly DNA with single stranded breaks, and both have poly-ADP ribosylation activity. On the other hand, the inventors have realized that programmed cell death in eukaryotes, particularly in plants, can be modulated by altering the expression level of the PARP genes or by altering the activity of the encoded proteins genetically, and that in order to achieve this goal, the expression of both genes needs to be altered or in the alternative both classes of proteins need to be altered in their activity.

Thus, the invention relates to modulation—i.e. the enhancement or the inhibition—of programmed cell death or apoptosis in eukaryotic cells, preferably plant cells, by altering the level of expression of PARP genes, or by altering the activity or apparent activity of PARP proteins in that eukaryotic cell. Conveniently, the level of expression of PARP genes or the activity of PARP proteins is controlled genetically by introduction of PCD modulating chimeric genes altering the expression of PARP genes and/or by introduction of PCD modulating chimeric genes altering the apparent activity of the PARP proteins and/or by alteration of the endogenous PARP encoding genes.

As used herein, "enhanced PCD" with regard to specified cells, refers to the death of those cells, provoked by the methods of the invention, whereby the killed cells were not destined to undergo PCD when compared to similar cells of a normal plant not modified by the methods of the invention, under similar conditions.

"Inhibited PCD" with regard to specified cells is to be understood as the process whereby a larger fraction of those cells or groups of cells, which would normally (without the intervention by the methods of this invention) undergo programmed cell death under particular conditions, remain alive under those conditions.

The expression of the introduced PCD modulating chimeric genes or of the modified endogenous genes will thus influence the functional level of PARP protein, and indirectly interfere with programmed cell death. A moderate decrease in the functional level of PARP proteins leads to an inhibition of programmed cell death, particularly to prevention of programmed cell death, while a severe decrease in the functional level of the PARP proteins leads to induction of programmed cell death.

In accordance with the invention, it is preferred that in order to inhibit or prevent programmed cell death in a eukaryotic cell, particularly in a plant cell, the combined level of both PARP proteins and/or their activity or apparent activity is decreased significantly, however avoiding that DNA repair (governed directly or indirectly by PARP) is inhibited in such a way that the cells wherein the function of the PARP proteins is inhibited cannot recover from DNA damage or cannot maintain their genome integrity. Preferably, the level and/or activity of the PARP proteins in the target cells, should be decreased about 75%, preferably about 80%, particularly about 90% of the normal level and/or activity in the target cells so that about 25%, preferably about 20%, particularly about 10% of the normal level and/or activity of PARP is retained in the target cells. It is further thought that the decrease in level and/or activity of the PARP proteins should not exceed 95%, preferably not exceed 90% of the normal activity and/or level in the target cells. Methods to determine the content of a specific protein such as the PARP proteins are well known to the person skilled in the art and include, but are not limited to (histochemical) quantification of such proteins using specific antibodies. Methods to quantify PARP activity are also available in the art and include the above-mentioned TUNEL assay (in vivo) or the in vitro assay described Collinge and Althaus (1994) for synthesis of poly (ADP-ribose) (see Examples).

Also in accordance with the invention, it is preferred that in order to trigger programmed cell death in a eukaryotic cell, particularly in a plant cell, the combined level of both PARP proteins and/or their activity or apparent activity is decreased substantially, preferably reduced almost completely such that the DNA repair and maintenance of the genome integrity are no longer possible. Preferably, the combined level and/or activity of the PARP proteins in the target cells, should be decreased at least about 90%, preferably about 95%, more preferably about 99%, of the normal level and/or activity in the target cells, particularly the PARP activity should be inhibited completely. It is particularly preferred that the functional levels of both classes of PARP proteins separately are reduced to the mentioned levels.

For the purpose of the invention, PARP proteins are defined as proteins having poly (ADP-ribose) polymerase activity, preferably comprising the so-called "PARP signature". The PARP signature is an amino acid sequence which is highly conserved between PARP proteins, defined by de Murcia and Menussier de Murcia (1994) as extending from amino acid at position 858 to the amino acid at position 906 from the *Mus musculus* PARP protein. This domain corresponds to the amino acid sequence from position 817 to 865 of the conventional PARP protein of *Zea mays* (ZAP1; SEQ ID No 2) or to the amino-acid sequence from position 827 to 875 of the conventional PARP protein of *Zea mays* (ZAP2; SEQ ID No 11) or to the amino acid sequence from position 500 to 547 of the non-conventional PARP protein of *Zea mays* (SEQ ID No 4) or to the amino acid sequence from position 485 to 532 of the non-conventional PARP protein of. *Arabidopsis thaliana* (SEQ ID No 6). This amino sequence is highly conserved between the different PARP proteins (having about 90% to 100% sequence identity). Particularly conserved is the lysine at position 891 (corresponding to position 850 of SEQ ID No 2, position 861 of SEQ ID No 11, position 532 of SEQ ID No 4, position 517 of SEQ ID No 6) of the PARP protein from *Mus musculus*, which is considered to be involved in the catalytic activity of PARP proteins. Particularly the amino acids at position 865, 866, 893, 898 and 899 of the PARP protein of *Mus musculus* or the corresponding positions for the other sequences are variable. PARP proteins may further comprise an N-terminal DNA binding domain and/or a nuclear localization signal (NLS).

Currently, two classes of PARP proteins have been described. The first class, as defined herein, comprises the so-called classical Zn-finger containing PARP proteins (ZAP). These proteins range in size from 113-120 kDA and are further characterized by the presence of at least one, preferably two Zn-finger domains located in the N-terminal domain of the protein, particularly located within the about 355 to about 375 first amino acids of the protein. The Zn-fingers are defined as peptide sequences having the sequence $CxxCx_nHxxC$ (whereby n may vary from 26 to 30) capable of complexing a Zn atom. Examples of amino acid sequences for PARP proteins from the ZAP class include the sequences which can be found in the PIR protein database with accession number P18493 (*Bos taurus*), P26466 (*Gallus gallus*), P35875 (*Drosophila melanogaster*), P09874 (*Homo sapiens*), P11103 (*Mus musculus*), Q08824 (*Oncorynchus masou*), P27008 (*Rattus norvegicus*), Q11208 (*Sarcophaga peregrina*), P31669 (*Xenopus laevis*) and the currently identified sequences of the ZAP1 and ZAP2 protein from *Zea mays* (SEQ ID No 2/SEQ ID No 11).

The nucleotide sequence of the corresponding cDNAs can be found in the EMBL database under accession numbers D90073 (*Bos taurus*), X52690 (*Gallus gallus*), D13806 (*Drosophila melanogaster*), M32721 (*Homo sapiens*), X14206 (*Mus musculus*), D13809 (Oncorynchus masou), X65496 (*Rattus norvegicus*), D16482 (*Sarcophaga peregrina*), D14667 (*Xenopus laevis*) and in SEQ ID No 1 and 10 (*Zea mays*).

The second class as defined herein, comprises the so-called non-classical PARP proteins (NAP). These proteins are smaller (72-73 kDa) and are further characterized by the absence of a Zn-finger domain at the N-terminus of the protein, and by the presence of an N-terminal domain comprising stretches of amino acids having similarity with DNA binding proteins. Preferably, PARP protein of these class comprise at least one amino acid sequence of about 30 to 32 amino acids which comprise the sequence R G x x x x G x K x x x x x R L (amino acids are represented in the standard one-letter code, whereby x stands for any amino acid; SEQ ID No 7). Even more preferably these PARP proteins comprise at least 1 amino acid sequence of about 32 amino acids having the sequence×L x V x x x R x x L x x R G L x x x V K x x L V x R L x x A I (SEQ ID No 8) (the so-called A1 domain) or at least 1 amino acid sequence of about 32 amino acids having the sequence G M x x x E L x x x A x x R G x x x x G x K K D x x R L x x (SEQ ID No 9)(the so-called A2 domain) or both. Particularly, the A1 and A2 domain are capable of forming a helix-loop-helix structure. These PARP proteins may further comprise a basic "B" domain (K/R rich amino acid sequence of about 35 to about 56 amino acids, involved in targeting the protein to the nucleus) and/or a an acid "C" domain (D/E rich amino acid sequence of about 36 amino acids). Examples of protein sequences from the NAP class include the APP protein from *Arabidopsis thaliana* (accessible from PIR protein database under accession number Q11207; SEQ ID No 6) and the NAP protein from *Zea mays* (SEQ ID No 4). The sequence of the corresponding cDNAs can be found in the EMBL database under accession number Z48243 (SEQ ID No 5) and in SEQ ID No 3. That the second class of PARP proteins are indeed functional PARP proteins, i.e. are capable of catalyzing DNA dependent poly(ADP-ribose) polymerization has been demonstrated by the inventors (see Example 2).

The inventors have further demonstrated that eukaryotic cells, particularly plant cells express simultaneously genes encoding PARP proteins from both classes.

It is clear that for the purpose of the invention, other genes or cDNAs encoding PARP proteins from both classes as defined, or parts thereof, can be isolated from other eukaryotic species or varieties, particularly from other plant species or varieties. These PARP genes or cDNAs can be isolated e.g. by Southern hybridization (either low-stringency or high-stringency hybridization depending on the relation between the species from which one intends to isolate the PARP gene and the species from which the probe was ultimately derived) using as probes DNA fragments with the nucleotide sequence of the above mentioned PARP genes or cDNAs, or parts thereof, preferably parts which are conserved such as a gene fragment comprising the nucleotide sequence encoding the PARP signature mentioned supra. The nucleotide sequences corresponding to the PARP signature from the PARP proteins encoded by plant genes are the nucleotide sequence of SEQ ID No 1 from nucleotide 2558 to 2704 or the nucleotide sequence of SEQ ID No 3 from nucleotide 1595 to 1747 or the nucleotide sequence of SEQ ID No 5 from nucleotide 1575 to 1724. If a discrimination is to be made between the classes of PARP genes, parts of the PARP genes which are specific for the class, such as the N-terminal domains preceding the catalytic domain or parts thereof, should preferably be used.

Alternatively, the genes or cDNAs encoding PARP proteins or parts thereof, can also be isolated by PCR-amplification using appropriate primers such as the degenerated primers with the nucleotide sequence corresponding to the sequences indicated in SEQ ID No 13, SEQ ID No 14, or primers with the nucleotide sequence corresponding to the sequences indicated in SEQ ID No 15 to 20. However, it is clear that the person skilled in the art can design alternative oligonucleotides for use in PCR or can use oligonucleotides comprising a nucleotide sequence of at least 20, preferably at least about 30, particularly at least about 50, consecutive nucleotides of any of the PARP genes to isolate the genes or part there of by PCR amplification.

It is clear that a combination of these techniques, or other techniques (including e.g. RACE-PCR), available to the skilled artisan to isolate genes or cDNAs on the basis of partial fragments and their nucleotide sequence, e.g. obtained by PCR amplification, can be used to isolate PARP genes, or parts thereof, suitable for use in the methods of the invention.

Moreover, PARP genes, encoding PARP proteins wherein some of the amino acids have been exchanged for other, chemically similar, amino acids (so-called conservative substitutions), or synthetic PARP genes (which encode similar proteins as natural PARP genes but with a different nucleotide sequence, based on the degeneracy of the genetic code) and parts thereof are also suited for the methods of the invention.

In one aspect of the invention, PCD in eukaryotic cells, particularly in plant cells, is inhibited by a moderate decrease in the functional level of PARP in those eukaryotic cells.

In one embodiment of this first aspect of the invention, the functional level of PARP in eukaryotic cells, particularly in plant cells is reduced by introduction of at least one PCD modulating chimeric gene in those cells, comprising a promoter capable of directing transcription in these cells, preferably a plant-expressible promoter, and a functional 3' transcription termination and polyadenylation region, operably linked to a DNA region which when transcribed yields a biologically active RNA molecule which is capable of decreasing the functional level of the endogenous PARP activity encoded by both classes of PARP genes.

In a preferred embodiment, at least two such PCD modulating chimeric genes are introduced in the cells, whereby the biologically active RNA encoded by the first PCD modulating chimeric gene decreases the functional level of the endogenous PARP activity encoded by the genes of the NAP class, and whereby the biologically active RNA encoded by the second PCD modulating chimeric gene decreases the functional level of the endogenous PARP activity encoded by the genes of the ZAP class, so that the combined PARP activity is moderately decreased.

In a particularly preferred embodiment, the PCD modulating chimeric genes decrease the functional level of the endogenous PARP activity by reducing the level of expression of the endogenous PARP genes. To this end, the transcribed DNA region encodes a biologically active RNA which decreases the mRNAs encoding NAP and ZAP class PARP proteins, that is available for translation. This can be achieved through techniques such as antisense RNA, co-suppression or ribozyme action.

As used herein, "co-suppression" refers to the process of transcriptional and/or post-transcriptional suppression of RNA accumulation in a sequence specific manner, resulting in the suppression of expression of homologous endogenous genes or transgenes.

Suppressing the expression of the endogenous PARP genes can thus be achieved by introduction of a transgene comprising a strong promoter operably linked to a DNA region whereby the resulting transcribed RNA is a sense RNA or an antisense RNA comprising a nucleotide sequence which has at least 75%, preferably at least 80%, particularly at least 85%, more particularly at least 90%, especially at least 95% sequence identity with or is identical to the coding or transcribed DNA sequence (sense) or to the complement (antisense) of part of the PARP gene whose expression is to be suppressed. Preferably, the transcribed DNA region does not code for a functional protein. Particularly, the transcribed region does not code for a protein. Further, the nucleotide sequence of the sense or antisense region should preferably be at least about 100 nucleotides in length, more preferably at least about 250 nucleotides, particularly at least about 500 nucleotides but may extend to the full length of the coding region of the gene whose expression is to be reduced.

For the purpose of this invention the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of the two sequences is performed by the Wilbur and Lipmann algorithm (Wilbur and Lipmann, 1983) using a window-size of 20 nucleotides or amino acids, a word length of 2 amino acids, and a gap penalty of 4. Computer-assisted analysis and inter relation of sequence data, including sequence alignment as described above, can be conveniently performed using commercially available software packages such as the programs of the Intelligenetics™ Suite (Intelligenetics Inc., CA).

It will be clear to a skilled artisan that one or more sense or antisense PCD modulating chimeric genes can be used to achieve the goals of the first aspect of the invention. When one sense or antisense PCD modulating chimeric gene is used, this gene must be capable of simultaneously reducing the expression of PARP genes of both classes. This can e.g. be achieved by choosing the transcribed region of the chimeric gene in such a way that expression of both classes of genes can be regulated by one sense or antisense RNA, i.e. by choosing target regions corresponding to the highest homology DNA region of the PARP genes of both classes and incorporating a sense or antisense transcribed DNA region corresponding to both target regions, conform to the conditions described above for sense and antisense RNA. Alternatively, different sense or antisense RNA regions, each specific for regulating the expression of one class of PARP genes, can be combined into one RNA molecule, encoded by one transcribed region of one PCD modulating chimeric gene. Obviously, the different sense or antisense RNA regions specific for regulating the expression of one class of PARP genes can be introduced as separate PCD modulating chimeric genes.

Preferred sense and antisense encoding transcribed regions comprise a nucleotide sequence corresponding (with sequence identity constraints as indicated above) to a sequence of at least about 100 consecutive nucleotides selected from the N-terminal domains of the PARP genes, preferably corresponding to a sequence of at least about 100 consecutive nucleotides selected from the sequence of SEQ ID No 1 from nucleotide position 113 to 1189, the sequence of SEQ ID No 3 from nucleotide position 107 to 583, the sequence of SEQ ID No 5 from nucleotide position 131 to 542 or the sequence of SEQ ID No 10 from nucleotide position 81 to 1180. However, it is clear that sense or antisense encoding transcribed regions can be used comprising a sequence corresponding to the complete sequence of the N-terminal domain of the PARP genes, or even to complete sequence of the PARP genes, particularly the protein-encoding region thereof. Further preferred are sense and antisense encoding transcribed regions which comprise a nucleotide sequence corresponding (with sequence identity constraints as indicated above) to a sequence of at least about 100 consecutive nucleotides selected from the C-terminal catalytic domains of the PARP genes, preferably a sequence of at least 100 nucleotides encompassing the PARP-signature encoding nucleotide sequences, particularly the PARP-signature encoding nucleotide sequences indicated supra. Again, it is clear that sense or aritisense encoding transcribed regions can be used comprising a sequence corresponding to the complete sequence of the C-terminal domain of the PARP genes.

In another particularly preferred embodiment, the PCD modulating chimeric genes decrease the functional level of the endogenous PARP activity by reducing the level of apparent activity of the endogenous PARPs of both classes. To this end, the transcribed DNA region encodes a biologically active RNA which is translated into a protein or inhibiting NAP or ZAP class PARP proteins or both, such as inactivating antibodies or dominant negative PARP mutants.

"Inactivating antibodies of PARP proteins" are antibodies or parts thereof which specifically bind at least to some epitopes of PARP proteins, such as the epitope covering part of the ZN finger 11 from position 111-118 in ZAP1 or a corresponding peptide in ZAP2, and which inhibit the activity of the target protein.

"Dominant negative PARP mutants" as used herein, are proteins or peptides comprising at least part of a PARP protein (or a variant thereof), preferably a PARP protein endogenous to the eukaryotic target host cell, which have no PARP activity, and which have an inhibitory effect on the activity of the endogenous PARP proteins when expressed in that host cell. Preferred dominant negative PARP mutants are proteins comprising or consisting of a functional DNA binding domain (or a variant thereof) without a catalytic domain (such as the N-terminal Zn-finger containing domain of about 355 to about 375 amino acids of a PARP: of the ZAP class, particularly a DNA binding protein domain comprising the amino acid sequence of SEQ ID No 2 from amino acid 1 to 370 or a DNA binding protein domain comprising the amino acid sequence of SEQ ID No 11 from amino acid 1 to 98, or a DNA binding protein domain comprising the amino acid sequence of SEQ ID No 2 from amino acid 1 to 370 wherein the amino acid sequence from amino acid 1 to 88 is replaced by the amino acid sequence of SEQ ID No 11 from amino acid at position 1 to the amino acid at position 98, or such as the N-terminal DNA binding protein domain of about 135 to 160 amino acids of a PARP of the NAP class, particularly a DNA binding protein domain comprising the amino acid sequence of SEQ ID No 4 from amino acid 1 to 159 or a DNA binding protein domain comprising the amino acid sequence of SEQ ID No 6 from amino acid 1 to 138) or without a functional catalytic domain (such as inactive PARP mutants, mutated in the so-called PARP signature, particularly mutated at the conserved lysine of position 850 of SEQ ID No 2, position 532 of SEQ ID No 4, position 517 of SEQ ID No 6). Preferably, dominant negative PARP mutants should retain their DNA binding activity. Dominant negative PARP mutants can be fused to a carrier protein, such as a β-glucuronidase (SEQ ID No 12).

Again, one or more PCD modulating genes encoding one or more dominant negative PARP mutants can be used to achieve the goals of the first aspect of the invention. When one PCD modulating chimeric gene is used, this gene must be capable of simultaneously reducing the expression of PARP genes of both classes.

In another embodiment of the first aspect of the invention, the functional level of PARP in eukaryotic cells, particularly in plant cells is reduced by modification of the nucleotide sequence of the endogenous PARP genes in those cells so that the encoded mutant PARP proteins retain about 10% of their activity. Methods to achieve such a modification of endogenous PARP genes include homologous recombination to exchange the endogenous PARP genes for mutant PARP genes e.g. by the methods described in U.S. Pat. No. 5,527, 695. In a preferred embodiment such site-directed modification of the nucleotide sequence of the endogenous PARP genes is achieved by introduction of chimeric DNA/RNA oligonucleotides as described in WO 96/22364 or U.S. Pat. No. 5,565,350.

In another aspect of the invention, programmed death of eukaryotic cells, preferably selected cells, particularly selected plant cells is enhanced by a severe decrease in the functional level of PARP, preferably reduced-almost completely, such that the DNA repair and maintenance of the genome integrity are no longer possible.

In one embodiment of this aspect of the invention, the functional level of PARP in eukaryotic cells, particularly in plant cells is reduced severely, particularly abolished almost completely, by introduction of at least one PCD modulating chimeric gene in those cells, comprising a promoter capable of directing transcription in these cells, preferably a plant-expressible promoter, and a functional 3' transcription termination and polyadenylation region, operably linked to a DNA region which when transcribed yields a biologically active RNA molecule which is capable of decreasing the functional level of the endogenous PARP activity encoded by both classes of PARP genes.

In a preferred embodiment of the second aspect of the invention, at least two such PCD modulating chimeric genes are introduced in the cells, whereby the biologically active RNA encoded by the first PCD modulating chimeric gene decreases the functional level of the endogenous PARP activity encoded by the genes of the NAP class, and whereby the biologically active RNA encoded by the second PCD modulating chimeric gene decreases the functional level of the endogenous PARP activity encoded by the genes of the ZAP class, so that the combined PARP activity is severely decreased, particularly almost completely eliminated.

As mentioned for the first aspect of this invention, the transcribed regions of the PCD modulating chimeric genes encode biologically active RNA, which can interfere with the expression of the endogenous PARP genes (e.g. through antisense action, co-suppression or ribozyme action) or the biologically active RNA can be further translated into a peptide or protein, capable of inhibiting the PARP proteins of the NAP and ZAP class, such as inactivating antibodies or dominant negative PARP mutants.

In a particularly preferred embodiment of the second aspect of the invention, the transcribed region of the PCD modulating chimeric genes (PCD enhancing chimeric genes) codes for a biologically active RNA which comprises at least one RNA region (preferably of at least about 100 nucleotides in length) classifying according to the above mentioned criteria as a sense RNA for at least one of the endogenous PARP genes, and at least one other RNA region (preferably of at least about 100 nucleotides in length), classifying according to the above mentioned criteria as an antisense RNA for at least one of the endogenous PARP genes, whereby the antisense and sense RNA region are capable of combining into a double stranded RNA region (preferably over a distance of at least about 100 nucleotides). In an especially preferred embodiment, two such PCD modulating genes, one targeted to reduce the functional level of a PARP protein of the NAP class, and the other targeted to reduce the functional level of a PARP protein of the ZAP class are introduced into an eukaryotic cell or organism, preferably a plant cell or plant.

It is clear that the different embodiments for the transcribed DNA regions of the chimeric PCD modulating genes of the invention can be used in various combinations to arrive at the goals of the invention. E.g. a first chimeric PCD modulating gene may encode a sense RNA designed to reduce the expression of an endogenous PARP gene of the ZAP class, while the second chimeric PCD modulating gene may encode a dominant negative PARP mutant designed to reduce the expression of an endogenous PARP gene of the NAP class.

Whether the introduction of PCD modulating chimeric genes into eukaryotic cells will ultimately result in a moderately reduced or a severally reduced functional level of combined PARP in those cells—i.e. in inhibited PCD or enhanced PCD—will usually be determined by the expression level (either on transcriptional level or combined transcriptional/translational level) of those PCD modulating genes. A major contributing factor to the expression level of the PCD modulating gene is the choice of the promoter region, although other factors (such as, but not limited to, the choice of the 3' end, the presence of introns, codon usage of the transcribed region, mRNA stability, presence of consensus sequence around translation initiation site, choice of 5' and 3' untranslated RNA regions, presence of PEST sequences, the influence of chromatin structure surrounding the insertion site of a stabile integrated PCD modulating gene, copy number of the introduced PCD modulating genes, etc.) or combinations thereof will also contribute to the ultimate expression level of the PCD modulating gene. In general, it can be assumed that moderate reduction of functional levels of combined PARP can be achieved by PCD modulating genes comprising a relatively weak promoter, while severe reduction of functional levels of combined PARP can be achieved by PCD modulating genes comprising a relatively strong promoter. However, the expression level of a PCD modulating gene comprising a specific promoter and eventually its effect on PCD, can vary as a function of the other contributing factors, as already mentioned.

For the purpose of particular embodiments of the invention, the PCD modulating chimeric genes may comprise a constitutive promoter, or a promoter which is expressed in all or the majority of the cell types throughout the organism, particularly throughout the plant, such as the promoter regions derived from the T-DNA genes, particularly the opine synthase genes of *Agrobacterium* Ti- or Ri-plasmids (e.g. nos, ocs promoters), or the promoter regions of viral genes (such as CaMV35S promoters, or variants thereof).

It may be further be advantageous to control the expression of the PCD modulating gene at will or in response to environmental cues, e.g. by inclusion of an inducible promoter which can be activated by an external stimuli, such as, but not limited to application of chemical compounds (e.g. safeners, herbicides, glucocorticoids), light conditions, exposure to abiotic stress (e.g. wounding, heavy metals, extreme temperatures, salinity or drought) or biotic stress (e.g. pathogen or pest infection including infection by fungi, viruses, bacteria, insects, nematodes, mycoplasms and mycoplasma like organisms etc.). Examples of plant-expressible inducible promoters suitable for the invention are: nematode inducible promoters (such as disclosed in WO 92/21757), fungus inducible promoters (WO 93/19188, WO 96/28561), promoters inducible after application of glucocorticoids such as dexamethasone ( ), or promoters repressed or activated after application of tetracyclin (Gatz et al. 1988; Weimann et al 1994)

In several embodiments of the invention, particularly for the second aspect of the invention (i.e. enhanced PCD), it may be convenient or required to restrict the effect on programmed cell death to a particular subset of the cells of the organism, particularly of the plant, hence the PCD modulating genes may include tissue-specific or cell type-specific promoters. Examples of suitable plant-expressible promoters selectively expressed in particular tissues or cell types are well known in the art and include but are not limited to seed-specific promoters (e.g. WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), meristem specific promoters (such as the promoter of the SHOOT- MERISTEMLESS (STM) gene, Long et al., 1996), primordia specific promoter (such as the promoter of the *Antirrhinum* CycD3a gene, Doonan et al., 1998), anther specific promoters (WO 89/10396, WO9213956, WO9213957) stigma-specific promoters (WO 91/02068), dehiscence-zone specific promoters (WO 97/13865), seed-specific promoters (WO 89/03887) etc.

Preferably the chimeric PCD modulating genes of the invention are accompanied by a marker gene, preferably a chimeric marker gene comprising a marker DNA that is operably linked at its 5' end to a plant-expressible promoter, preferably a constitutive promoter, such as the CaMV $^{35}$S promoter, or a light inducible promoter such as the promoter of the gene encoding the small subunit of Rubisco; and operably linked at its 3' end to suitable plant transcription 3' end formation and polyadenylation signals. It is expected that the choice of the marker DNA is not critical, and any suitable marker DNA can be used. For example, a marker DNA can encode a protein that provides a distinguishable "color" to the transformed plant cell, such as the A1 gene (Meyer et al., 1987) or Green Fluorescent Protein (Sheen et al., 1995), can provide herbicide resistance to the transformed plant cell, such as the bar gene, encoding resistance to phosphinothricin (EP 0,242,246), or can provided antibiotic resistance to the transformed cells, such as the aac(6') gene, encoding resistance to gentamycin (WO94/01560).

Methods to introduce PCD modulating chimeric genes into eukaryotic cells, particularly methods to transform plant cells are well known in the art, and are believed not to be critical for the methods of the invention. Transformation results in either transient or stably transformed cells (whereby the PCD modulating chimeric genes are stably inserted in the genome of the cell, particularly in the nuclear genome of the cell).

It is clear that the methods and means described in this invention to alter the programmed cell death in eukaryotic cells and organisms, particularly in plant cells and plants, has several important application possibilities. Inhibition of PCD by the methods and means of the invention, can be used to relieve the stress imposed upon the cells, particularly the plant cells, during transformation and thus to increase transformation efficiency, as described in WO 97/06267. Inhibition of PCD can also be used to improve cell culture of eukaryotic cells, particularly of plant cells. Triggering of PCD in particular cell types using the means and methods of the invention, can be used for methods which call upon the use of a cytotoxin. Since PCD is the "natural" way for cells to die, the use of PCD enhancing chimeric genes of the invention constitutes an improvement over the use of other cytotoxic genes such as RNAse or diptheria toxin genes which lead to cell lysis. Moreover, low-level expression of PCD enhancing genes in cells different than the targeted cells, will lead to a moderate reduction instead of a severe reduction of PARP activity in those cells, thus actually inhibiting PCD in non-target cells.

For plants, preferred applications of PCD enhancing chimeric genes include, but are not limited to:
1. the generation of plants protected against fungus infection, whereby the PCD enhancing chimeric gene or genes comprise a fungus-responsive promoter as described in WO 93/19188 or WO 96/28561.
2. the generation of nematode resistant plants, whereby the PCD enhancing chimeric gene or genes comprise a nematode inducible promoters such as disclosed in WO 92/21757
3. the generation of male or female sterile plants, whereby the PCD enhancing chimeric gene or genes comprise anther-specific promoters (such as disclosed in WO 89/10396, WO9213956, WO9213957) or stigma-specific promoters (such as disclosed in WO 91/02068)
4. the generation of plants with improved seed shatter characteristics whereby the PCD enhancing chimeric gene or genes comprise dehiscence zone-specific promoters (such as disclosed in WO 97/13865).

Although it is clear that the invention can be applied essentially to all plant species and varieties, the invention will be especially suited to alter programmed cell death in plants with a commercial value. Particularly preferred plants to which the invention can be applied are corn, oil seed rape, linseed, wheat, grasses, alfalfa, legumes, a brassica vegetable, tomato, lettuce, cotton, rice, barley, potato, tobacco, sugar beet, sunflower, and ornamental plants such as carnation, chrysanthemum, roses, tulips and the like.

The obtained transformed plant can be used in a conventional breeding scheme to produce more transformed plants with the same characteristics or to introduce the chimeric cell-division controlling gene of the invention in other varieties of the same or related plant species. Seeds obtained from the transformed plants contain the PCD modulating gene of the invention as a stable genomic insert.

The following non-limiting Examples describe the construction of chimeric apoptosis controlling genes and the use of such genes for the modulation of the programmed cell death in eukaryotic cells and organisms. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) Current Protocols in Molecular Biology, *Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences:
SEQ ID No 1: DNA sequence of the ZAP gene of *Zea mays* (zap1)
SEQ ID No 2: protein sequence of the ZAP protein of *Zea mays* (ZAP1)
SEQ ID No 3: DNA sequence of the NAP gene of *Zea mays* (nap)
SEQ ID No 4: protein sequence of the NAP protein of *Zea mays* (NAP)
SEQ ID No 5: DNA sequence of the NAP gene of *Arabidopsis thaliana* (app)
SEQ ID No 6: protein sequence of the NAP protein of *Arabidopsis thaliana* (APP)
SEQ ID No 7: consensus sequence for the A domain of non-conventional PARP proteins
SEQ ID No 8: consensus sequence for the A1 domain of non-conventional PARP proteins
SEQ ID No 9: consensus sequence for the A2 domain of non-conventional PARP proteins
SEQ ID No 10: DNA sequence of the second ZAP gene of *Zea mays* (Zap2)
SEQ ID No 11: protein sequence of the ZAP protein of *Zea mays* (ZAP2)
SEQ ID No 12: amino acid sequence of a fusion protein between the DNA binding domain of APP and the GUS protein
SEQ ID No 13: degenerated PCR primer
SEQ ID No 14: degenerated PCR primer
SEQ ID No 15: PCR primer SEQ ID No 16: PCR primer
SEQ ID No 17: PCR primer
SEQ ID No 18: PCR primer
SEQ ID No 19: PCR primer
SEQ ID No 20: PCR primer
SEQ ID No 21: app promoter-gus translational fusion
Sequence Listing Free Text
The following free text has been used in the Sequence Listing part of this application
<223> Description of Artificial Sequence: A domain of non-conventional PARP proteins
<223> Description of Artificial Sequence: A1 domain on non conventional PARP protein
<223> Description of Artificial Sequence: A2 domain of non-conventional PARP protein
<223> Description of Artificial Sequence: fusion protein between APP N-terminal domain and GUS protein
<223> Description of Artificial Sequence: degenerated PCR primer
<223> Description of Artificial Sequence: oligonucleotide for use as PCR primer
<223> Description of Artificial Sequence: APP promoter fusion with beta-glucuronidase gene
<223> translation initiation codon

EXAMPLES

Experimental Procedures

Yeast and Bacterial Strains

*Saccharomyces cerevisiae* strain DY (MATa his3 canl-10 ade2 leu2 trp1 ura3::(3xSV40 AP1-lacZ) (Kuge and Jones, 1994) was used for the expression of the APP protein. Yeast transformation was carried out according to Dohmen et al (1991). Strains were grown on a minimal SDC medium (0.67% yeast nitrogen base, 0.37% casamino acids, 2% glucose, 50 mgl$^{-1}$ of adenine and 40 mgl$^{-1}$ of tryptophan). For the induction of the APP expression, glucose in SDC was substituted with 2% galactose.

*Escherichia coli* strain XL-I (Stratagene, La Jolla, Calif.) was used for the plasmid manipulations and library screenings, which were carried out according to standard procedures (Ausubel et al., 1987; Sambrook et al., 1989). *E. coli* BL21 (Studier and Moffat, 1986) was used for the APP protein expression and *Agrobacterium tumefaciens* C58C1 Rif$^R$ (pGV2260) (Deblaere et al., 1985) for the stable transformation of plants.

Poly(ADP-ribose)Polymerase Activity Assay

Enzymatic activity of the APP was assayed in total protein extracts of yeast strains prepared as follows. DY(pV8SPA) or DY(pYeDP1/8-2) were grown in 50 ml of SDC medium overnight at 30° C. on a gyratory shaker at 150 rpm. Yeast cells were harvested by centrifugation at 1,000×g, washed three times with 150 ml of 0.1 M potassium phosphate buffer (pH 6.5), and resuspended in 5 ml of sorbitol buffer (1.2 M sorbitol, 0.12 M K$_2$HPO$_4$, 0.033 M citric acid, pH 5.9). Lyticase (Boehringer, Mannheim, Germany) was added to the cell suspension to a final concentration of 30 U ml$^{-1}$ and cells were incubated at 30° C. for 1 h. Yeast spheroplasts were then washed three times with sorbitol buffer and resuspended in 2 ml of ice-cold lysis buffer (100 mM Tris-HCl, pH 7.5, 400 mM NaCl, 1 mM EDTA, 10% glycerol, 1 mM DTT). After sonication, the lysate was centrifuged at 20,000×g for 20 min at 4° C. and the supernatant was desalted on a Econo-Pack™ 10 DG column (Bio-Rad, Richmond, Calif.) equilibrated with reaction buffer (100 mM Tris-HCl, pH 8.0, 10 mM MgCl$_2$, 1 mM DTT). To reduce proteolytic degradation of proteins, the lysis and reaction buffers were supplemented with a protease inhibitor cocktail (Boehringer), one tablet per 50 ml. Nucleic acids were removed from the total extracts by adding NaCl and protamine sulfate to a final concentration of 600 mM and 10 mg ml$^1$, respectively. After incubation at room temperature for 10 min, the precipitate was removed by centrifugation at 20,000×g for 15 min at 4° C. The buffer of the supernatant was exchanged for the reaction buffer by gel filtration on an Econo-Pack™ 10 DG column.

The assay for the synthesis of poly(ADP-ribose) was adapted from Collinge and Althaus (1994). Approximately 500 µg of total yeast protein were incubated in a reaction buffer supplemented with 30 µCi of $^{32}$P-NAD$^+$ (500 Ci mmol$^{-1}$), unlabeled NAD$^+$ to a final concentration of 60 µM, and 10 µg ml$^{-1}$ sonicated salmon sperm DNA. After incubation for 40 min at room temperature, 500 µl of the stop buffer (200 mM Tris-HCl, pH 7.6, 0.1 M NaCl, 5 mM EDTA, 1% Na$^+$-N-lauroyl-sarcosine, and 20 µg ml$^{-1}$ proteinase K) were added and reactions incubated at 37° C. overnight. After phenol and phenol/chloroform extractions, polymers were precipitated with 2.5 volumes of ethanol with 0.1 M NaAc (pH 5.2). The pellet was washed with 70% ethanol, dried, and dissolved in 70% formamide, 10 mM EDTA, 0.01% bromophenol blue, and 0.01% xylene cyanol. Samples were heated at 80° C. for 10 min and then loaded onto a 12% polyacrylamide/6 M urea sequencing gel. Gels were dried on 3 MM paper (Whatman International, Maidstone, UK) and exposed either to Kodak X-Omat X-ray film (Eastman Kodak, Richmond, N.Y.) or scanned using a PhosphorImager™445SI (Molecular Dynamics, Sunnyvale, Calif.).

Immunological Techniques

A truncated app cDNA encoding an APP polypeptide from amino acids Met$^{310}$ to His$^{637}$ was expressed as a translation fusion with six histidine residues at the N terminus after induction of a 500-ml culture of the *E. coli* BL21 (pETΔNdeSPA) with 1 mM isopropyl-β-D-thiogalactopyranoside. The APP polypeptide was purified to near homogeneity by affinity chromatography under denaturing conditions (in the presence of 6 M guanidinium hydrochloride) on a Ni$^{2+}$-NTA-agarose column, according to the manufacturers protocol (Qiagen, Chatsworth, Calif.). After dialysis against PBS, a mixture of the soluble and insoluble APP polypeptides was used to immunize two New Zealand White rabbits following a standard immunization protocol (Harlow and Lane, 1988). For the Western blot analysis, proteins were resolved by denaturing SDS-PAGE (Sambrook et al., 1989; Harlow and Lane, 1988) and transferred onto nitrocellulose membranes (Hybond-C; Amersham), using a Semi-Dry Blotter II (Kem-En-Tec, Copenhagen, Denmark).

In situ antigen localization in yeast cells was carried out as described (Harlow and Lane, 1988). For the localization of the APP protein in yeast spheroplasts, anti-APP serum was diluted 1:3,000 to 1:5,000 in Tris-buffered saline-BSA buffer. 10H monoclonal antibody, which specifically recognizes poly(ADP-ribose) polymer (Ikajima et al., 1990) was used in a 1:100 dilution in PBS buffer. The mouse antibody were detected with the sheep anti-mouse IgG F(ab')$_2$ fragment conjugated to fluorescein isothiocyanate (FITC) (Sigma) at a dilution of 1:200. Rabbit IgG was detected with CY-3 conjugated sheep anti-rabbit IgG sheep F(ab)$_2$ fragment (Sigma), at a dilution of 1:200. For the visualization of DNA, slides were incubated for 1 min in PBS with 10 µg ml$^{-1}$ of 4',6-diamidino-2-phenylindole (DAPI; Sigma). Fluorescence imaging was performed on an Axioskop epifluorescence microscope (Zeiss, Jena, Germany). For observation of FITC and CY-3 fluorochromes, 23 and 15 filter cubes were used, respectively. Cells were photographed with Fuji Color-100 super plus film.

Plant Material and Histochemical Analysis

*Nicotiana tabacum* SR1 (Maliga et al., 1975) was used for the generation of stable transformants following the procedure of leaf disc cocultivation (De Block et al., 1987) with *A. tumefaciens* C58C1 Rif$^R$ (pGV2260; PGCNSPAGUS). *N. tabacum* SR1 line transformed with authentic GUS under the control of the 35S CaMV was used as a control. *Arabidopsis thaliana* ecotype Columbia was used for the transformation of the app-promoter-GUS fusion following the in situ infiltration procedure.

For in situ histochemical staining of the GUS activity, plant samples were fixed in ice-cold 90% acetone for 30 min, washed in 0.1 M $K_2HPO_4$ (pH 7.8), and then incubated in staining buffer (0.1 M $K_2HPO_4$, pH 7.8, 2 mM X-Gluc, 20 mM $Fe^{3+}$-EDTA) at 37° C. Stained plant tissues were stored in 70% ethanol at 4° C. When necessary, browning of tissues due to phenolic oxidation was reduced by incubation with lactophenol (Beeckman and Engler, 1994). The GUS staining was examined under a Jenalumar light microscope (Zeiss). Plant tissues were photographed with Fuji Color-100 super plus film.

Miscellaneous Methods

The plasmid construction steps were routinely verified by DNA sequencing carried out according to protocols provided by USB Biochemicals (Cleveland, Ohio). $^{32}$P-labeled DNA probes for nucleic acid hybridization were synthesized by the Ready-Prime DNA labelling kit (Amersham). For DNA and RNA hybridization experiments, the buffer system of Church and Gilbert (1984) was used (0.25 M sodium phosphate, pH 7.2, 7% SDS, 1% BSA, 1 mM EDTA). For Western blot analysis, yeast total proteins were extracted with phenol essentially as described for plant tissues (Hurkman and Tanaka, 1986). For Northern blot analysis, total yeast RNA was extracted with hot phenol as described (Ausubel et al., 1987). RNA was resolved on 1.5% agarose gels after denaturation with glyoxal (Sambrook et al., 1989). Hybond-N nylon filters (Amersham) were used for the nucleic acid blotting.

Example 1

Isolation of Genes Encoding PARP Homologues from *Zea Mays*

With the purpose of isolating maize cDNA encoding PARP homologue(s) two approaches were followed. First, a maize cDNA library was screened under low-stringency DNA—DNA hybridization conditions using a DNA probe prepared from the *Arabidopsis* app cDNA. Secondly, PCR amplification of part of the maize PARP was performed, using the first-strand cDNA as a template and two degenerate primers, designed on the basis of the sequence of the "PARP signature" the most conserved amino acid sequence between all known PARP proteins.

A λZAP (Stratagene) cDNA library from leaves of maize (*Zea mays* L.), inbred line B734. Plaques (500,000) were screened according to standard procedures (Sambrook et al., 1989). After screening with the *Arabidopsis* app probe, one non-full-length cDNA of 1.4 kbp was purified. After the initial cDNA library screening with the app probe and a subsequent 5' rapid amplification of cDNA ends (RACE) PCR analysis, the nap gene, a maize homologue of the *Arabidopsis* app, was identified. For the 5'RACE PCR, the template was prepared with the Marathon kit (Clontech, Palo Alto, Calif.) and 0.5 µg of maize poly(A)$^+$ RNA isolated from inner sheath, outer sheath, and leaves of 1-week-old maize seedlings. The gene-specific, nested primers for PCR amplification were 5'-GGGACCATGTAGTTTATCTTGACCT-3' (SEQ ID No 15) and 5'-GACCTCGTACCCCAACTCTTCCCCAT-3' (SEQ ID No 16) for nap primers. The amplified PCR products were subcloned and sequenced. A fragment of 800 bp was amplified with nap specific primers which allowed to reconstruct the 2295-bp-long sequence of nap cDNA (SEQ ID No 3).

The NAP protein was 653 amino acids long (molecular mass ~73 kDa; SEQ ID No 4) and highly similar (61% sequence identity and 69% similarity) to the APP. Most importantly, NAP had an organization of the N-terminus congruent to APP (FIG. 1A), suggesting a rather strict selection pressure on the structure of APP-like proteins in plants. The nap gene was unique in the maize genome (FIG. 2A) and encoded a transcript of 2.4 kb (FIG. 2C).

Using degenerate primers based on very highly conserved regions in the "PARP signature" and first-strand cDNA from *Zea mays* as a template, a 310-bp fragment was amplified. For the PCR with degenerate primers 5'-CCGAATTCGGN-TAYATGTTYGGNAA-3' (SEQ ID No 13) and 5'-CCGAAT-TCACNATRTAYTCRTTRTA-3' (SEQ. ID No 14) with Y=C/T; R=A/G; N=A/G/C/T), the first strand cDNA was used as a template and was synthesized using 5 µg of poly(A)$^+$ RNA from young maize leaves and MuMLV reverse transcriptase. PCR amplifications were performed with Taq DNA polymerase in 100 µl volume using the following conditions: 1 min at 95° C., 2 min at 45° C., 3 min at 72° C., followed by 38 cycles of 1 min at 95° C., 2 min at 45° C., 3 min at 72° C., with a final incubation for 10 min at 72° C.

The sequence of the 310 bp fragment showed 55% sequence identity and 64% sequence similarity with human PARP over the same region, but was, however, different from the sequence of the nap cDNA. Three zap cDNAs were identified after screening with the 310-bp fragment, which was obtained by PCR with degenerate primers. These three purified cDNA were all derived from the same transcript because they had identical 3' non-coding regions; the longest clone (#9) was sequenced on both strands (SEQ ID No 1). This cDNA encoded a PARP-homologous polypeptide of 689 amino acids (SEQ ID No 2; molecular mass ~109 kDa), which we designated as ZAP1 (FIG. 1B). The first Zn-finger of ZAP1 was probably nonfunctional because it had the sequence CKSCxxxHASV, which included no third cysteine residue.

5'RACE PCR analysis of zap transcripts from the maize line LG2080 (the screened cDNA library was made from the inbred line B734) was performed as described above using the following zap specific primers 5'-AAGTCGACGCGGC-CGCCACACCTAGTGCCAGGTCAG-3' (SEQ ID No 17) and 5'-ATCTCAATTGTACATTTCTCAGGA-3' (SEQ ID No 18). A 450-bp PCR product was obtained after PCR with zap-specific primers. Eight independent, because of their slight differences in lengths at their 5' ends, 5'RACE PCR fragments generated with zap-specific primers were sequenced. In all the transcripts from the LG2080 maize plants, there was an insertion of additional sequence in the coding region, which made the ZAP protein longer by 11 amino acids (980 amino acids, molecular mass ~110.4 kDa). The Zn-finger I of ZAP2 was standard and read CKSCxxx-HARC (FIG. 1B; SEQ ID No 11). The sequence difference may be due either to differences between maize varieties, to the expression of two homologous genes, or to alternative splicing. In fact, maize may have at least two zap genes (FIG. 2B), which encode a transcript of 3.4-3.5 kb (FIG. 2D). The DNA gel blot experiment with a probe prepared from the zap cDNA showed that homologous genes were present in *Arabidopsis*.

Structurally ZAP was very similar to PARP from animals. It had a well conserved DNA-binding domain composed of two Zn-fingers (36% identity and 45% similarity to the DNA-binding domain of mouse PARP). Even higher homology was shown by comparing only the sequences of the Zn-fingers, Ala$^1$-Phe$^{162}$ in the mouse enzyme (44% identity and 54% similarity), or a subdomain downstream from the nuclear localization signal (NLS), Leu$^{237}$-Ser$^{360}$ in mouse PARP (40% identity and 50% similarity). Whereas the bipartite nuclear localization signal characteristic of mammalian PARP could not be identified in ZAP, the sequence KRKK fitted a monopartite NLS (FIG. 1B). The putative automodification domain was poorly conserved and was shorter in ZAP than in mouse PARP. The compilation of the homology of the catalytic domains between ZAP, NAP, APP and mouse PARP is shown in FIG. 2. It should be noted that the NAD$^+$-binding domain of ZAP was more similar to the mammalian enzyme (48% identity) than to that of APP and NAP (40% and 42% sequence identity, respectively), whereas APP and NAP were 68% identical and 76% similar in their catalytic domain.

Example 2

Demonstration that Non-Conventional PARP Protein has a DNA-Dependent Poly(ADP-Ribose) Polymerase Activity APP is a DNA-Dependent Poly(ADP-ribose) Polymerase A more detailed study of the APP protein (expressed in yeast) was performed to understand the activity of PARP-like proteins from the NAP class. The choice of yeast as the organism for the expression and enzymatic analysis of the *Arabidopsis* APP protein was made for a number of reasons. As an eukaryote, *Saccharomyces cerevisiae* is better suited for the expression of native proteins from other eukaryotic organisms, and unlike most other eukaryotic cells, it does not possess endogenous PARP activity (Lindahl et al., 1995).

The full-length app cDNA was placed in pYeDP1/8-2 under the control of a galactose-inducible yeast promoter in the following way the full-length app cDNA was excised from pC3 (Lepiniec et al., 1995) as an XhoI-EcoRI fragment. The ends were filled in with the Klenow fragment of DNA polymerase 1, and the fragment was subcloned into the SmaI site of the yeast expression vector pYeDP1/8-2 (Cullin and Pompon, 1988). The resulting expression vector pV8SPA (FIG. 4A) was transformed into *S. cerevisiae* strain DY.

For APP expression in *E. coli*, the complete coding region of the app cDNA was PCR amplified with Pfu DNA polymerase (Stratagene), using the primers 5'-AGGATCCCATG-GCGAACAAGCTCAAAGTGAC-3' (SEQ ID No 19) and 5'-AGGATCCTTAGTGCTTGTAGTTGAAT-3' (SEQ ID No 20), and subcloned as a BamHI fragment into pET19b (Novagene, Madison, Wis.), resulting in pETSPA. The expression of the full-length APP in *E. coli* BL21 from pETSPA was very poor. To obtain better expression, pETSPA was digested with NcoI and NdeI or with SmaI, the ends were filled in by the Klenow fragment of DNA polymerase 1, and the plasmids were then self-ligated. Of the resulting plasmids pETΔNdeSPA and pETΔSmaSPA, only pETΔNdeSPA gave satisfactory expression of the truncated APP polypeptide (Met$^{310}$ to His$^{637}$) in *E. coli* BL21.

The expression of the APP in yeast was verified by Northern and Western blot analysis. (FIG. 4) As the promoter in pV8SPA is inactive when cells are grown on glucose and derepressed on galactose-containing media, the expression was expected to be tightly regulated by the carbon source. However, Northern blot analysis of RNA and immunoblot analysis of proteins in DY(pV8SPA) as compared to the control DY strain containing the empty vector, showed that app mRNA and APP protein were expressed in yeast even when grown on glucose-containing media (FIG. 4B, lane 2). The peculiarity of the expression observed on glucose-containing medium was that both app mRNA and APP protein were shorter than the ones detected after induction with galactose (compare lanes 2 and 4 in FIG. 4B). The APP polypeptide with the higher molecular weight, (apparently a full-length protein) was only detected on galactose-containing medium, although such cells also expressed the truncated mRNA and protein. The most probable explanation for this finding is that when the DY(pV8SPA) strain is grown on glucose, there is a leaky expression from the expression cassette, with transcription beginning 200-300 bp downstream from the transcription start observed after galactose induction. This shorter mRNA probably does not code for the first methionine (Met$^1$) of APP and, therefore, translation is initiated at Met$^{72}$. This would explain the observed difference of ~5 kDa (calculated difference being 7.5 kDa) in the molecular masses of the APP polypeptides from strains grown on glucose or on galactose. The possibility that the differences in molecular masses may be attributed to self-modification through poly(ADP-ribos)ylation was ruled out by growing strains in the presence of PARP inhibitors, such as 3ABA and nicotinamide (FIG. 4B, compare lanes 6 and 8 to lane 4).

To detect the synthesis of poly(ADP-ribose), total proteins were extracted from yeast strains grown under different conditions and incubated in the presence of radioactively labeled NAD$^+$. To prevent synthesis of poly(ADP-ribose) and possible automodification of the APP in vivo, strains were also grown in the presence of 3ABA, a reversible inhibitor of PARP, which was subsequently removed from the protein extracts during desalting. FIG. 5 shows that poly(ADP-ribose) is synthesized by protein extracts of DY(pV8SPA) grown on galactose (FIG. 5A, lanes 1 and 2), but not by a strain containing the empty vector (FIG. 5A, lane 4). It can also be seen that *Arabidopsis* APP could synthesize polymers up to 40 residues in length (FIG. 5A, lane 1) with the majority of the radioactivity being incorporated into 10-15-mer. This observation is consistent with the polymer sizes detected by other authors (Chen et al., 1994). More radioactivity was incorporated into polymer when the yeast strain was grown with 3ABA than without (FIG. 5A, lane 1 compared to lane 2); the reason might be that either the APP extracted from inhibited cultures was less automodified (it is believed that automodification inhibits the activity of PARP) or the labeled NAD$^+$ was used by the enzyme from the uninhibited culture for the extension of existing polymer, resulting in a lower specific activity overall. Under the same reaction conditions poly(ADP-ribose) synthesized by human PARP, either in reaction buffer alone or in the presence of a yeast total protein extract from DY(pYeDP1/8-2) (FIG. 5A, lanes 5 and 6, respectively), showed much longer chains, possibly up to 400-mer (de Murcia and Ménissier de Murcia, 1994).

The stimulation of enzymatic activity by nicked DNA is a well known property of PARP from animals (Alvarez-Gonzalez and Althaus, 1989). We therefore tested whether the activity of the APP protein was DNA dependent. After removal of yeast nucleic acids (DNA, RNA) and some basic proteins from the galactose-grown DY(pV8SPA) protein extract the synthesis of poly(ADP-ribose) was analyzed in the presence of increasing concentrations of sonicated salmon sperm DNA. As can be seen in FIG. 5B, there was a direct correlation between the amount of DNA present in the reaction and the incorporation of $^{32}$P-NAD$^+$. Scanning of the phosphor-images indicated that ~6-fold more radioactivity was incorporated into poly(ADP-ribose) in the reaction mixture containing 40 μg ml$^-$ of DNA than into that with 2 μg ml$^{-1}$ of DNA (FIG. 5B, lanes 4 and 2, respectively). The synthesis of the polymer was sensitive to 3ABA in the reaction mix (FIG. 5B, lane 5).

APP is a Nuclear Protein

In animal cells PARP activity is localized in the nucleus (Schreiber et al., 1992). The intracellular localization, if nuclear, of APP could provide an important additional indication that APP is a bona fide plant PARP. To this end, the localization of the APP polypeptides in yeast cells was analyzed using anti-APP antisera. The APP polypeptide synthesized in yeast grown on galactose was found mainly in the nucleus. This localization was unaffected by the presence in the media of the PARP inhibitors.

In addition, we tested whether APP was constitutively active in yeast cells, as has been reported for the human PARP (Collinge and Althaus, 1994). Here, fixed yeast spheroplasts were incubated with monoclonal 10H antibody, which specifically recognizes poly(ADP-ribose) polymers (Kawamitsu et al., 1984). A positive yellowish-green fluorescence signal with 10H antibody was localized in the nucleus and was observed only in DY(pV8SPA) cells grown on galactose. Positive staining was greatly reduced in cells grown in the presence of the PARP inhibitors, 3ABA and nicotinamide.

To identify the intracellular localization of APP in plant cells, a widely adopted approach in plant studies was used, i.e., the examination of the subcellular location of a fusion protein formed between the protein in question and a reporter gene, once the protein fusion was produced in transgenic plants or transfected cells (Citovsky et al., 1994; Sakamoto and Nagatani, 1996; Terzaghi et al, 1997; von Arnim and Deng, 1994). An N-terminal translational fusion of GUS with the part of the APP polypeptide extending from the Met$^1$ to Pro$^{407}$ was made. The translational fusion of APP with bacterial GUS was constructed as follows. Plasmid pETSPA was cut with SmaI, treated with alkaline phosphatase, and ligated to a blunted NcoI-XbaI fragment from pGUS1 (Plant Genetic Systems N.V., Gent, Belgium). The ligation mix was transformed into E. coli XL-1 and cells were plated onto LB medium supplemented with 0.1 mM isopropyl-β-D-thiogalactopyranoside, 40 μg ml$^{-1}$ 5-bromo-4-chloro-3-indolyl-β-D-glucuronide, and 100 μg ml$^-$ of ampicillin. In this way, pETSPAGUS was selected as blue colonies. The expression in E. coli of the ~110-kDa fusion protein was confirmed by in situ GUS activity gels (Lee et al., 1995). The APP-GUS fusion was placed under the control of the 35S promoter of the CaMV (the Klenow-blunted BamHI fragment from pETSPA-GUS was subcloned into SmaI-digested pJD330; Gallie and Walbot, 1992) and the resulting expression cassette was subcloned as an XbaI fragment into the XbaI site of the pCGN1547 binary vector (McBride and Summerfelt, 1990) to give pGCNSPAGUS. The pGCNSPAGUS was finally introduced into A. tumefaciens C58C1 Rif$^R$(pGV2260) by the freezing-thawing transformation procedure.

Expression of the fusion protein was verified in E. coli. The chimeric cDNA under the control of the 35S CaMV promoter was stably integrated into the tobacco genome. Progeny from four independent transgenic tobacco plants were analyzed for the subcellular distribution of the GUS activity after in situ histochemical staining (Jefferson et al., 1987). In 2-day-old seedlings GUS activity could be detected in cotyledons and in roots, but not in hypocotyls or root tips. Because of the transparency of root tissues, GUS staining was clearly localized in the nuclei of root hairs and epidermal cells. Additionally, some diffuse, non-localized staining of other root cells was seen, in particular along the vascular cylinders. This non-nuclear GUS staining was more pronounced in leaf tissues. Whereas young true leaves or cotyledons displayed intense blue staining of the nuclei, there was also some diffuse staining of the cytoplasm. In fully expanded leaves, however, GUS staining became homogenous and similar to the staining of control plants transformed with GUS under the control of the CaMV 35S promoter, in which GUS was expressed in the cytoplasm. Eventually, older leaves or cotyledons exhibited practically no histochemically detectable GUS activity, with the exception of the vascular bundles, where the GUS staining could not be confined to any particular cell compartment.

Deficiency in DNA Ligase I Induces Expression of the App Gene

PARP in animal cells is one of the most abundant nuclear proteins and its activity is regulated by allosteric changes in the protein upon binding to damaged DNA. We found that the app gene in Arabidopsis had a rather low level of expression, suggesting that transcriptional activation of this gene might be essential for APP function in vivo. To test this hypothesis, the expression of the app gene was studied during in vivo genome destabilization caused by a DNA ligase I deficiency. A T-DNA insertion mutation, line SK1B2, in the Arabidopsis DNA ligase I gene was isolated previously (Babiychuk et al., 1997). The mutation is lethal in the homozygous state, but the mutant allele shows normal transmission through the gametes. We therefore expected that cells homozygous for the mutation would die due to incomplete DNA synthesis during the S phase of the cell cycle, soon after the fertilization of the mutant embryo sac with mutant pollen.

An app promoter-GUS translational fusion, in which the coding region of GUS was fused in-frame with the first five amino acids of APP and 2 kb of app 5' flanking sequences was constructed (SEQ ID No 21). The gene encoding the fusion protein was transformed into Arabidopsis. After two backcrosses to a wild type, heterozygous plants transformed with app promoter-GUS were crossed with Arabidopsis line SK1B2. The inflorescence of the control plants and plants heterozygous for the ligase mutation were stained for the activity of GUS. The GUS staining pattern mostly detected in aging tissues probably reflects the expression of the app gene, although we have no firm evidence that all of the regulatory sequences were present in the constructs used. This pattern was the same both in the inflorescences of control plants, not carrying the mutant ligase gene and plants heterozygous for a mutation. Approximately one-fourth of the ovules in the mutant plants with the fusion protein are GUS positive. Closer microscopical examination showed that in the GUS-positive ovules only the gametophyte was stained. The only difference between the control plants and the mutant plant was a mutation in a DNA ligase gene. We therefore conclude that the app gene is induced because of either the accumulation of DNA breaks, or the death of the mutant embryo sacs fertilized with mutant pollen. GUS staining of embryo sacs was found to appear within 24 h after pollination, or therefore very soon after fertilization.

Example 3

Construction of PCD Modulating Chimeric Genes and Introduction of the T-DNA Vectors Comprising such PCD Modulating Genes in an *Agrobacterium* Strain 3.1. Construction of the p35S:(dsRNA-APP) and p35S:(dsRNA-ZAP) Genes Using standard recombinant DNA procedures, the following DNA regions are operably linked, as schematically outlined in FIG. 6 (constructs 1 and 5):

For the p35S:(dsRNA-ZAP) chimeric gene
a CaMV 35S promoter region (Odell et al., 1985)
a Cab22 leader region (Harpster et al., 1988)
a ZAP encoding DNA region (about complete) (the *Arabidopsis thaliana* homologue to SEQ ID No 10, isolated by hybridization)
about 500 bp of the 5' end of the ZAP2 encoding DNA region in inverse orientation
a CaMV35S 3' end region (Mogen et al., 1990)

For the p35S:(dsRNA-APP) chimeric gene
a CaMV 35S promoter region (Odell et al., 1985)
a Cab22 leader region (Harpster et al., 1988)
an APP encoding DNA region (about complete) (SEQ ID No 5)
about 500 bp of the 5' end of the APP encoding DNA region in inverse orientation
a CaMV35S 3' end region (Mogen et al., 1990)

3.2. Construction of the pNOS:(dsRNA-APP) and PNOS:(dsRNA-ZAP) Genes

Using standard recombinant DNA procedures, the following DNA regions are operably linked, as schematically outlined in FIG. 6 (constructs 2 and 6):

For the pNOS:(dsRNA-ZAP) chimeric gene
a NOS promoter region (Herrera-Estrella et al., 1983)
a Cab22 leader region (Harpster et al., 1988)
a ZAP encoding DNA region (about complete) (the *Arabidopsis thaliana* homologue to SEQ ID No 10, isolated by hybridization)
about 500 bp of the 5' end of the ZAP2 encoding DNA region in inverse orientation
a CaMV35S 3' end region (Mogen et al., 1990)

For the pNOS:(dsRNA-APP) chimeric gene
a NOS promoter region (Herrera-Estrella et al., 1983)
a Cab22 leader region (Harpster et al., 1988)
an APP encoding DNA region (about complete) (SEQ ID No 5)
about 500 bp of the 5' end of the APP encoding DNA region in inverse orientation
a CaMV35S 3' end region (Mogen et al., 1990)

3.3. Construction of the pTA29:(dsRNA-APP) and PTA29:(dsRNA-ZAP) Genes

Using standard recombinant DNA procedures, the following DNA regions are operably linked, as schematically outlined in FIG. 6 (constructs 3 and 7):

For the pTA29:(dsRNA-ZAP) chimeric gene
a TA29 promoter region (WO 89/10396)
a Cab22 leader region (Harpster et al., 1988)
a ZAP encoding DNA region (about complete) (the *Arabidopsis thaliana* homologue to SEQ ID No 10, isolated by hybridization)
about 500 bp of the 5' end of the ZAP2 encoding DNA region in inverse orientation
a CaMV35S 3' end region (Mogen et al., 1990)

For the pTA29:(dsRNA-APP) chimeric gene
a TA29 promoter region (WO 89/10396)
a Cab22 leader region (Harpster et al., 1988)
an APP encoding DNA region (about complete) (SEQ ID No 5)
about 500 bp of the 5' end of the APP encoding DNA region in inverse orientation
a CaMV35S 3' end region (Mogen et al., 1990)

3.4. Construction of the DNTP303:(dsRNA-APP) and DNTP303:(dsRNA-ZAP) Genes

Using standard recombinant DNA procedures, the following DNA regions are operably linked, as schematically outlined in FIG. 6 (constructs 4 and 8):

For the pNTP303:(dsRNA-ZAP) chimeric gene
a NTP303 promoter region (Wetering 1994)
a Cab22 leader region (Harpster et al., 1988)
a ZAP encoding DNA region (about complete) (the *Arabidopsis thaliana* homologue to SEQ ID No 10, isolated by hybridization)
about 500 bp of the 5' end of the ZAP2 encoding DNA region in inverse orientation
a CaMV35S 3' end region (Mogen et al., 1990)

For the pNTP303:(dsRNA-APP) chimeric gene
a NTP303 promoter region (Wetering, 1994)
a Cab22 leader region (Harpster et al., 1988)
an APP encoding DNA region (about complete) (SEQ ID No 5)
about 500 bp of the 5' end of the APP encoding DNA region in inverse orientation
a CaMV35S 3' end region (Mogen et al., 1990)

3.5 Construction of the Chimeric Marker Genes

Using standard recombinant DNA procedures, the following DNA regions are operably linked, as schematically outlined in FIG. 6:

For the gat marker gene
an Act2 promoter region (An et al., 1996)
a aminoglycoside 6'-acetyltransferase encoding DNA (WO 94/26913)
a 3' end region of a nopaline synthase gene (Depicker et al., 1982)

For the bar marker gene
an Act2 promoter region (An et al., 1996)
a phosphinotricin acetyltransferase encoding DNA (U.S. Pat. No. 5,646,024)
a 3' end region of a nopaline synthase gene (Depicker et al., 1982)

3.6. Construction of the T-DNA Vectors Comprising the PCD Modulating Chimeric Genes Using appropriate restriction enzymes, the chimeric PCD modulating genes described under 3.1 to 3.5 are excised and introduced in the polylinker between the T-DNA borders of a T-DNA vector derived from pGSV5 (WO 97/13865) together with either the gat marker gene or the bar marker gene. The resulting T-DNA vectors are schematically represented in FIG. 6.

3.7. Introduction of the T-DNA Vectors in *Agrobacterium*

The T-DNA vectors are introduced in *Agrobacterium tumefaciens* C58C1Rif(pGV4000) by electroporation as described by Walkerpeach and Velten (1995) and transformants are selected using spectinomycin and streptomycin.

Example 4

*Agrobacterium*-Mediated Transformation of *Arabidopsis thaliana* with the T-DNA Vectors of Example 3

The *Agrobacterium* strains are used to transform *Arabidopsis thaliana* var. C24 applying the root transformation method as described by Valvekens et al. (1992). The explants are coinfected with the *Agrobacteria* strains containing the dsRNA-APP respectively the dsRNA-ZAP constructs. The dsRNA-APP constructs are used in combination with the pact:bargene. The dsRNA-ZAP constructs are used in combination with the pact-gat gene. Transformants are selected for phosphinothricin resistance. The regenerated rooted transgenic lines are tested for the presence of the other T-DNA by screening for kanamycin resistance. Transgenic lines containing both T-DNA's are transferred to the greenhouse. The phenotype of the T0-transgenic lines is scored and the T1-generations are studied further in more detail.

Example 5

*Agrobacterium*-Mediated Transformation of *Brassica napus* with the T-DNA Vectors of Example 3

The *Agrobacterium* strains are used to transform the *Brassica napus* var. N90-740 applying the hypocotyl transformation method essentially as described by De Block et al. (1989), except for the following modifications:

hypocotyl explants are precultured for 1 day on A2 medium [MS, 0.5 g/l Mes (pH5.7), 1.2% glucose, 0.5% agarose, 1 mg/l 2,4-D, 0.25 mg/l naphthalene acetic acid (NAA) and 1 mg/l 6-benzylaminopurine (BAP)].

infection medium A3 is MS, 0.5 g/l Mes (pH5.7), 1.2% glucose, 0.1 mg/l NM, 0.75 mg/l BAP and 0.01 mg/l gibberellinic acid (GA3).

selection medium A5G is MS, 0.5 g/l Mes (pH5.7), 1.2% glucose, 40 mg/l adenine. $SO_4$, 0.5 g/l polyvinylpyrrolidone (PVP), 0.5% agarose, 0.1 mg/l NM, 0.75 mg/l BAP, 0.01 mg/l GA3, 250 mg/l carbenicillin, 250 mg/l triacillin, 5 mg/l $AgNO_3$ for three weeks. After this period selection is continued on A5J medium (similar a A5G but with 3% sucrose)

regeneration medium A6 is MS, 0.5 g/l Mes (pH5.7), 2% sucrose, 40 mg/l adenine. $SO_4$, 0.5 g/l PVP, 0.5% agarose, 0.0025 mg/l BAP and 250 mg/l triacillin.

healthy shoots are transferred to rooting medium which was A9: half concentrated MS, 1.5% sucrose (pH5.8), 100 mg/l triacillin, 0.6% agar in 1 liter vessels.

MS stands for Murashige and Skoog medium (Murashige and Skoog, 1962)

For introducing both the dsRNA-APP and the dsRNA-ZAP T-DNA constructs into a same plant cell the co-transformation method is applied, essentially as described by De Block and Debrouwer (1991). Transformed plant lines are selected on phosphinothricin containing medium after which the presence of the second T-DNA is screened by testing the regenerated rooted shoots for kanamycin resistance. In the co-transformation experiments, the dsRNA-APP constructs are used in combination with the pact:bar gene. The dsRNA-ZAP constructs are used in combination with the pact:gat gene. Transgenic lines containing both T-DNA's are transferred to the greenhouse. The phenotype of the T0-transgenic lines is scored and the T1-generations are studied further in more detail.

Example 6

In Vitro Assay to Test Vigor of Plant Lines 6.1. Fitness Assay for *Brassica napus*
Media and Reaction Buffers
  Sowing medium:
    Half concentrated Murashige and Skoog salts
    2% sucrose
    pH 5.8
    0.6% agar
  Callus inducing medium: A2S
    MS medium, 0.5 g/l Mes (pH 5.8), 3% sucrose, 40 mg/l adenine-$SO_4$, 0.5% agarose, 1 mg/l 2,4-D, 0.25 mg/l NM, 1 mg/l BAP
  Incubation medium:
    25 mM K-phosphate buffer pH5.8
    2% sucrose
    1 drop Tween20 for 25 ml medium
  Reaction buffer:
    50 mM K-phosphate buffer pH7.4
    10 mM 2,3,5-triphenyltetrazoliumchloride (TTC) (=3.35 mg/ml)
    1 drop Tween20 for 25 ml buffer
Sterilization of Seeds and Growing of the Seedlings
  Seeds are soaked in 70% ethanol for 2 min, then surface-sterilized for 15 min in a sodium hypochlorite solution (with about 6% active chlorine) containing 0.1% Tween20. Finally, the seeds are rinsed with 1 l of sterile distilled water. Put 7 seeds/1 l vessel (Weck) containing about 75 ml of sowing medium. The seeds are germinated at 23° C. and 30 µEinstein/$s^{-1}m^{-2}$ with a daylength of 16 h.
  The line N90-740 is always included for standardization between experiments.
Preculture of the Hypocotyl Explants
  12-14 days after sowing, the hypocotyls are cut in about 7 mm segments. 25 hypocotyls/Optilux Petridisch (Falcon S1005)
  The hypocotyl explants are cultured for 4 days on medium A2S at 23-25° C. (at 30 µEinstein/$s^{-1}m^{-2}$).
    □P.S.: about 150-300 hypocotyl explants/line are needed to carry out the assay
  Transfer the hypocotyl explants to Optilux Petridishes (Falcon S1005) containing 30 ml of incubation medium.
  Incubate for about 20 hours at 24° C. in the dark.
TTC-Assay
  Transfer 150 hypocotyl explants to a 50 ml Falcon tube.
  Wash with reaction buffer (without TTC).
  Add 25 ml-30 ml of reaction buffer/tube.
    tube 1□ no TTC added
      for measuring background absorption
      one line/experiment is sufficient
    tube 2□+10 mM TTC
    (explants have to be submerged, but do not vacuum infiltrate!)
  turn tubes upside down
  Incubate for about 1 hour in the dark at 26° C. (no end reaction!)
  Wash hypocotyls with deionized water
  Remove water
  Freeze at −70° C. for 30 min.
  Thaw at room°t (in the dark)
  Add 50 ml ethanol (technical)
  Extract reduced TTC-H by shaking for 1 hour
  Measure absorptions of extracts at 485 nm P.S.: reduced UTC-His not stable □ keep in the dark and measure O.D.$_{485}$ as soon as possible $$O.D._{485(TTC\text{-}H)}=(O.D._{485}+TTC)-(O.D._{485}-TTC)$$

Comparison of the TTC-reducing capacities between samples of different independent experiments can be done by setting the TTC-reducing capacity of N90-740 in the different experiment at 100%.

Lines with a high TTC-reducing capacity are vigorous, while lines with a low TTC-reducing capacity are weak.

6.2. Fitness Assay *Arabidopsis*

Media and Reaction Buffers
Plant medium: Half concentrated Murashige and Skoog salts
1.5% sucrose
pH 5.8
0.6% agar
→autoclave 15 min.
add filter sterilized—100 mg/l myo-inositol
0.5 mg/l pyridoxine
0.5 mg/l nicotinic acid
1 mg/l thiamine
Incubation medium: 10 mM K-phosphate buffer pH5.8
2% sucrose
1 drop Tween20 for 25 ml medium
Reaction buffer: 50 mM K-phosphate buffer pH7.4
10 mM 2,3,5-triphenyltetrazoliumchloride (TTC) (=3.35 mg/ml)
1 drop Tween20 for 25 ml buffer

*Arabidopsis* Plants
Sterilization of *Arabidopsis* Seeds
2 min. 70% ethanol
10 min. bleach (6% active chlorine)+1 drop Tween 20 for 20 ml solution
wash 5 times with sterile water
P.S.: sterilization is done in 2 ml eppendorf tubes *Arabidopsis* seeds sink to the bottom of the tube, allowing removal of the liquids by means of a 1 ml pipetman Growing of *Arabidopsis* Plants
Seeds are sown in 'Intergrid Tissue Culture disks of Falcon' (nr. 3025) containing ±100 ml of plant medium: 1 seed/grid.
Plants are grown at 23° C.
40 µEinstein s$^{-1}$m$^{-2}$
16 hours light-8 hours dark
for about 3 weeks (plants start to form flower buds)
→P.S.: *about 90-110 plants/line are needed to carry out the assay
include control line (C24; Columbia; . . . ) for calibration Pre-Incubation
Harvest *Arabidopsis* shoots by cutting of roots (by means of scissors)
Put each shoot immediately in incubation medium (shoots have to be submerged, but do not vacuum infiltrate)
Incubation medium: 1150 ml in 'Intergrid Tissue Culture disks of Falcon' (nr. 3025)
a) incubation medium: for quantification of background absorption (see TTC-assay)
b) incubation medium
c) incubation medium+2 mM niacinamide
30-35 shoots/petridish (but same amount of shoots for all lines and for each condition)
Incubate at 24° C. in the dark for ±20 hours TTC-Assay
Transfer shoots to 50 ml Falcon tubes
Wash with reaction buffer (without TTC)
Add 30-35 ml of reaction buffer/tube
a) no TTC added (for measuring background absorption)
b and c)+10 mM TTC
(Shoots have to be submerged, but do not vacuum infiltrate!)
Incubate for about 2 hours in the dark at 26° C. (no end reaction!)
Wash shoots with deionized water
Remove water
Freeze at −70° C. for 30 min.
Thaw at room°t (in the dark)
Add 50 ml ethanol (technical)
Extract reduced TTC-H by shaking for 1 hour
Measure absorptions of extracts at 485 nm
P.S.: reduced TTC-His not stable e keep in the dark and measure O.D.$_{485}$ as soon as possible
Compare reducing profiles of tested lines versus control line (for population of 30 to 35 plants)

$$O.D._{485(TTC\text{-}H)}=(O.D._{485}+TTC)-(O.D._{485}-TTC)$$

Comparison of the TTC-reducing capacities between samples of different independent experiments can be done by setting the TTC-reducing capacity of control line (C24; Columbia; . . . ) in the different experiments at 100%.

Lines with a high TTC-reducing capacity are vigorous, while lines with a low TTC-reducing capacity are weak.

If the addition of niacinamide to the incubation medium results in a higher TTC-reducing capacity indicates to a lower fitness (as shown for C24 and Columbia).

Example 7

Phenotypic Analyses of the Transgenic Lines Containing Both dsRNA-APP and dsRNA-ZAP Constructs The flower phenotype and pollen viability (Alexander staining (Alexander, 1969) and germination assay) of the T0-lines containing dsRNA-APP and dsRNA-ZAP under the control of tapetum or pollen specific promoters were scored. For *Arabidopsis*, the T1-generation is obtained by selving or if the plants are male sterile by backcrossing using pollen of non-transformed wild type plants. For *Brassica napus*, the T1-generation is always obtained by backcrossing using pollen of non-transformed plants.

T1-seed is germinated on kanamycin containing medium after which the resistant plants are scored by means of the ammonium-multiwell assay for phosphinothricine resistance (De Block et al., 1995). One half of the plants that contains both T-DNA's is transferred to the greenhouse to score the male fertility of the plants, while the other half is used to quantify the vigor of the plants by means of the fitness assay. For plants comprising combinations (APP/ZAP) of PCD modulating genes under control of 35S or NOS promoter, a high vigor is observed in a number of the transgenic lines.

For plants comprising combinations (APP/ZAP) of PCD modulating genes under control of TA29 male sterility is observed in a number of the transgenic lines.

For plants comprising combinations (APP/ZAP) of PCD modulating genes under control of NTP303 sterile pollen is observed in a number the transgenic lines.

REFERENCES

Alexander (1969) Stain Technology 44, 117
Alvarez-Gonzalez and Althaus (1989) *Mut. Res.* 218, 67-74
An et al. (1996) *The Plant Cell* 8, 15-30
An et al. (1996b) *Plant Journal* 10, 107-121
Ausubel et al. (1994) *Current Protocols in Molecular Biology, Current Protocols*, USA.
Ausubel et al. (1987) *Current Protocols in Molecular Biology* 1987-1988. New York: Greene Publishing Associates & Wiley-Interscience
Babiychuk et al (1997) *Proc. Natl. Acad. Sci. USA*, 94, 12722-12727
Beeckman and Engler (1994) *Plant Mol. Biol. Rep.* 12, 37-42.
Chen et al. (1994) *Eur. J. Biochem* 224, 135-142
Citovsky et al. (1994) *Proc. Natl. Acad. Sci. USA*, 91, 3210-3214.
Cohen (1993) *Immunol. Today* 14, 126-130
Collinge and Althaus (1994) *Mol. Gen. Genet.* 245, 686-693
Croy (1993) *Plant Molecular Biology Labfax* jointly published by BIOS Scientific Publications Ltd (UK) and Blackwell Scientific Publications, UK.
Cullin and Pompon (1988) *Gene*, 65, 203-217
De Block et al. (1987) *EMBO J.* 6, 2513-2518
De Block et al. (1989) *Plant Physiol.* 91: 694
De Block and Debrouwer (1991) *Theor. Appl. Genet.* 82, 257-263
De Block et al. (1995) *Planta* 197, 619-626
de Murcia and Ménissier de Murcia (1994) *Trends Biochem. Sci.* 19, 172-176.
Deblaere et al. (1985) *Nucleic Acids Res.* 13, 4777-4788
Depicker et al. (1982) *J. Mol. App. Gen.* 1, 561-573
Ding et al. (1992) *J. Biol. Chem.* 267, 12804-12812
Dohmen et al. (1991) *Yeast*, 7, 691-692
Doonan et al. (1998) in "*Plant Cell Division*" (Francis, Duditz and Inzé, Eds.) Portland Press, London
Ellis et al. (1991) *Annu. Rev. Cell. Biol.* 7, 663-698
Gallie and Walbot (1992) *Nucleic Acids Res.* 20, 4631-4638
Gatz et al. (1988) *Proc. Natl. Acad. Sci. USA* 85, 1394-1397
Gavrieli et al. (1992) *J. Cell. Biol.* 119, 493-501
Harlow and Lane (1988) *Antibodies: A Laboratory Manual.* Cold Spring Harbor: Cold Spring Harbor Laboratory Press
Harpster et al. (1988) *Mol. Gen. Genet.* 212, 182-190.
Hawkins and Phillips (1983) *Plant Sci. Lett.* 32, 221-224
Heller et al. (1995) *J. Biol. Chem.* 270, 11176-11180
Herrera-Estrella et al. (1983) *EMBO J.* 2, 987
Hudspeth et al. (1989) *Plant Mol Biol* 12, 579-589
Hurkman and Tanaka (1986) *Plant Physiol.* 81, 802-806
Ikajima et al. (1990) *J. Biol. Chem.* 265, 21907-21913
Jefferson et al. (1987) *EMBO J.* 6, 3901-3907
Kameshita et al. (1984) *J. Biol. Chem.* 259, 4770-4776
Kawamitsu et al. (1984) *Biochemistry*, 23, 3771-3777
Keil et al. (1989) *EMBO J.* 8, 1323-1330
Keller et al. (1988) *EMBO J.* 7, 3625-3633
Keller et al. (1989) *Genes Devel.* 3, 1639-1646
Kuepper et al. (1990) *J. Biol. Chem.* 265, 18721-18724
Kuge and Jones (1994) *EMBO J.* 13, 655-664
Lazebnik et al. (1994) *Nature* 371, 346-347
Lee et al. (1995) *Plant J.* 8, 603-612
Lepiniec et al. (1995) *FEBS Letters* 364, 103-108
Lindahl et al. (1995) *Trends Biochem. Sci.* 20, 405-411
Long et al. (1996) *Nature*, 379, 66-69
Maliga et al. (1975) *Nature*, 255, 401-402
McBride and Summerfelt (1990) *Plant Mol. Biol.* 14, 269-276
Ménissier de Murcia et al. (1997) *Proc. Natl. Acad. Sci. USA*, 94, 7303-7307
Mogen et al. (1990) *The Plant Cell* 2, 1261
Molinette et al. (1993) *EMBO J.* 12, 2109-2117
Odell et al. (1985) *Nature* 313, 810
O'Farrel (1995) *Biochimie* 77, 486-491
Payne et al. (1976) *Exp. Cell Res.* 99, 428-432
Peleman et al. (1989) *Gene* 84, 359-369
Pennell and Lamb (1997) *The Plant Cell* 9, 1157-1168
Phillips and Hawkins (1985) *J. Exp. Bot.* 36, 119-128
Puchta et al. (1995) *Plant J.* 7, 203-210
Sakamoto and Nagatani (1996) *Plant J.* 10, 859-868
Sambrook et al. (1989) *Molecular Cloning: A Laboratory Manual*, Second Edition, Cold Spring Harbor Laboratory Press, NY
Schreiber et al. (1992) *EMBO J.* 11, 3263-3269
Sheen et al. (1995) *The Plant Journal* 8, 777-784
Shoji et al. (1997) *Plant Cell Physiol.* 38, 36-43
Smulson et al. (1995) *J. Biol. Chem.* 270, 119-127
Studier and Moffat (1986) *J. Mol. Biol.* 189, 113-130
Sugiyama et al. (1995) *J. Plant Res.* 108, 351-361
Terzaghi et al. (1997) *Plant J.* 11, 967-982
Valvekens et al. (1988) PNAS 85, 5536
von Arnim and Deng (1994) *Cell*, 79, 1035-1045
Wang et al. (1995) *Genes Dev.* 9, 509-520
Wang et al. (1996) *Plant Cell* 8, 375-391
Wang et al. (1997) *Genes Dev.* 11, 2347-2358
Weimann et al. (1994) *Plant J.* 5, 559-569
Wetering (1994) PhD thesis, Katholieke Universiteis Nijmegen
Walkerpeach and Velten (1995) In: Gelvin S B, Schilperoort R A, Verma D P S (eds) Plant Molecular Biology Manual pp B1/1-B1/19. Kluwer Academic Publishers, Dordrecht
Wilbur and Lipmann (1983) *Proc. Natl. Acad. Sci. USA* 80, 706
Willmitzer and Wagner (1982) In *ADP-Ribosylation Reactions* (Hayashi, O. and Ueda, K., eds). New York: Academic Press, pp. 241-252
Zhang et al. (1994) *Science*, 263, 687-689

We claim:

1. A method for obtaining a cell of a plant with high vigor, when compared to a control plant cell, comprising the steps of:
   i) identifying an endogenous PARP encoding gene or cDNA from said plant comprising:
      a. performing PCR on genomic or cDNA from said plant at an annealing temperature of at least 45° C. using a primer pair selected from the nucleotide sequences comprising at least 20 consecutive nucleotides of the nucleotide sequence of SEQ ID No.: 1, SEQ ID No.: 3, SEQ ID NO.: 5 or SEQ ID No.: 10;
      b. performing PCR on genomic or cDNA from said plant at an annealing temperature of at least 45° C. using a primer pair selected from the nucleotide sequences comprising at least 20 consecutive nucleotides of the nucleotide sequence of SEQ ID NO: 1 from nucleotide position 2558 to 2704, the sequence of SEQ ID NO: 3 from nucleotide position 1595 to 1747, the sequence of SEQ ID NO: 5 from nucleotide position 1575 to 1724, or the sequence of SEQ ID NO: 10 from nucleotide position 2559 to 2705; or
      c. performing PCR on genomic or cDNA from said plant at an annealing temperature of at least 45° C. using a primer pair selected from the following nucleotide sequences: SEQ ID No.: 13 and SEQ ID No.: 14; SEQ ID No.: 15 and SEQ ID No.: 16; SEQ ID No.: 17 and SEQ ID No.: 18; SEQ ID No.: 19 and SEQ ID No.: 20; and
   ii) introducing a chimeric gene to said cell to yield a transgenic cell, wherein said chimeric gene comprises the following operably linked DNA regions:
      a) a plant-expressible promoter;
      b) a DNA region, which when transcribed yields an RNA molecule, capable of reducing the expression of said endogenous PARP encoding gene or cDNA; and
      c) a DNA region involved in transcription termination and polyadenylation wherein said RNA molecule for introduction into said cell of said plant comprises
         i) a sense nucleotide sequence comprising at least 100 consecutive nucleotides from said endogenous PARP encoding gene or cDNA of said plant; and
         ii) an antisense nucleotide sequence comprising at least 100 consecutive nucleotides from the complement of said sense nucleotide sequence;
      said sense and said antisense nucleotide sequence being capable of combining into a double stranded RNA region; and
      wherein said vigor of said cell of said plant can be measured by measuring the capacity of explants of said plant to reduce 2,3,5-triphenyltetrazoliumchloride.

2. The method of claim 1, wherein said PARP encoding gene or cDNA is of the ZAP class.

3. The method of claim 1, wherein said PARP encoding gene or cDNA is of the NAP class.

4. The method of claim 1, wherein said plant expressible promoter is a constitutive promoter.

5. The method of claim 1, further comprising the step of regenerating a transgenic plant from said transgenic plant cell.

6. The method of claim 5, further comprising the step of producing more plants comprising said chimeric gene by a conventional breeding scheme.

7. The method of claim 1, wherein said sense nucleotide sequence comprises at least 100 consecutive nucleotides selected from the sequence of SEQ ID NO: 1 from nucleotide position 113 to 1189, the sequence of SEQ ID NO: 3 from nucleotide position 107 to 583, the sequence of SEQ ID NO: 5 from nucleotide position 131 to 542, or the sequence of SEQ ID NO: 10 from nucleotide position 81 to 1180.

8. The method of claim 1, wherein said sense nucleotide sequence comprises at least 100 consecutive nucleotides from the sequence of SEQ ID NO: 1 from nucleotide position 2558 to 2704, the sequence of SEQ ID NO: 3 from nucleotide position 1595 to 1747, the sequence of SEQ ID NO: 5 from nucleotide position 1575 to 1724, or the sequence of SEQ ID NO: 10 from nucleotide position 2559 to 2705.

9. The method of claim 1, wherein said RNA molecule comprises a sense nucleotide sequence comprising at least 250 consecutive nucleotides from SEQ ID NO: 1, 3, 5, or 10.

10. The method of claim 1, wherein said RNA molecule comprises a sense nucleotide sequence comprising at least 500 consecutive nucleotides from SEQ ID NO: 1, 3, 5, or 10.

11. A *Zea mays, Brassica napus*, or *Arabidopsis thaliana* plant exhibiting high vigor when compared to a control plant obtained by the method of claim 5, said plant comprising a chimeric gene comprising the following operably linked DNA regions:
   a) a plant-expressible promoter;
   b) a DNA region, which when transcribed yields an RNA molecule capable of reducing the expression of said endogenous PARP encoding gene or cDNA; and
   c) a DNA region involved in transcription termination and polyadenylation; wherein said RNA molecule transcribed from said chimeric gene in said plant comprises
      i) a sense nucleotide sequence comprising at least 100 consecutive nucleotides from said endogenous PARP encoding gene or cDNA of said plant; and
      ii) an antisense nucleotide sequence comprising at least 100 consecutive nucleotides from the complement of said sense nucleotide sequence;
   said sense and antisense nucleotide sequence being capable of combining into a double stranded RNA region; and
   wherein said vigor of said cell of said plant can be measured by measuring the capacity of explants of said plant to reduce 2,3,5-triphenyltetrazoliumchloride.

12. The transgenic plant of claim 11, wherein said PARP encoding gene or cDNA is of the ZAP class.

13. The transgenic plant of claim 11, wherein said PARP encoding gene or cDNA is of the NAP class.

14. The transgenic plant of claim 11, wherein said plant expressible promoter is a constitutive promoter.

15. The transgenic plant of claim 11, wherein said sense nucleotide sequence comprises at least 100 consecutive nucleotides from the sequence of SEQ ID NO: 1 from nucleotide position 113 to 1189, the sequence of SEQ ID NO: 3 from nucleotide position 107 to 583, the sequence of SEQ ID NO: 5 from nucleotide position 131 to 542, or the sequence of SEQ ID NO: 10 from nucleotide position 81 to 1180.

16. The transgenic plant of claim 11, wherein said sense nucleotide sequence comprises at least 100 consecutive nucleotides from the sequence of SEQ ID NO: 1 from nucleotide position 2558 to 2704, the sequence of SEQ ID NO: 3 from nucleotide position 1595 to 1747, the sequence of SEQ ID NO: 5 from nucleotide position 1575 to 1724, or the sequence of SEQ ID NO: 10 from nucleotide position 2559 to 2705.

17. The transgenic plant of claim 11, wherein said RNA molecule comprises a sense nucleotide sequence comprising of at least 250 consecutive nucleotides from SEQ ID NO: 1, 3, 5, or 10.

18. The transgenic plant of claim 11, wherein said RNA molecule comprises a sense nucleotide sequence comprising at least 500 consecutive nucleotides from SEQ ID NO: 1, 3, 5, or 10.

19. A seed of the plant of claim 11, comprising said chimeric gene.

20. The chimeric gene described in claim 1.

21. The chimeric gene of claim 20, wherein said PARP encoding gene or cDNA is of the ZAP class.

22. The chimeric gene of claim 20, wherein said PARP encoding gene or cDNA is of the NAP class.

23. The chimeric gene of claim 20, wherein said plant expressible promoter is a constitutive promoter.

24. The chimeric gene of claim 20, wherein said sense nucleotide sequence comprises at least 100 consecutive nucleotides from the sequence of SEQ ID NO: 1 from nucleotide position 113 to 1189, the sequence of SEQ ID NO: 3 from nucleotide position 107 to 583, the sequence of SEQ ID NO: 5 from nucleotide position 131 to 542, or the sequence of SEQ ID NO: 10 from nucleotide position 81 to 1180.

25. The chimeric gene of claim 20, wherein said sense nucleotide sequence comprises at least 100 consecutive nucleotides selected from the sequence of SEQ ID NO: 1 from nucleotide position 2558 to 2704, the sequence of SEQ ID NO: 3 from nucleotide position 1595 to 1747, the sequence of SEQ ID NO: 5 from nucleotide position 1575 to 1724, or the sequence of SEQ ID NO: 10 from nucleotide position 2559 to 2705.

26. The chimeric gene of claim 20, wherein said RNA molecule comprises a sense nucleotide sequence comprising at least 250 consecutive nucleotides from SEQ ID NO: 1, 3, 5, or 10.

27. The chimeric gene of claim 20, wherein said RNA molecule comprises a sense nucleotide sequence comprising at least 500 consecutive nucleotides from SEQ ID NO: 1, 3, 5, or 10.

28. A method for obtaining a cell of a plant with high vigor, when compared to a control plant cell, comprising the steps of:
   i) identifying an endogenous PARP encoding gene or cDNA from said plant comprising:
      a. performing a hybridization reaction on genomic or cDNA from said plant using a probe comprising the nucleotide sequence of SEQ ID No.: 1, SEQ ID No.: 3, SEQ ID No.: 5, or SEQ ID No.: 10;
      b. performing a hybridization reaction on genomic or cDNA from said plant using a probe comprising at least 20 consecutive nucleotides of a nucleotide sequence of SEQ ID No.: 1, SEQ ID No.: 3, SEQ ID No.: 5, or SEQ ID No.: 10;
      c. performing a hybridization reaction on genomic or cDNA from said plant using a probe comprising the nucleotide sequence of SEQ ID NO.: 1 from nucleotide position 113 to 1189, the sequence of SEQ ID NO.: 3 from nucleotide position 107 to 583, the sequence of SEQ ID NO.: 5 from nucleotide position 131 to 542, or the sequence of SEQ ID NO.: 10 from nucleotide position 81 to 1180; or d. performing a hybridization reaction on genomic or cDNA from said plant using a probe comprising the nucleotide sequence of SEQ ID NO: 1 from nucleotide position 2558 to 2704, the sequence of SEQ ID NO: 3 from nucleotide position 1595 to 1747, the sequence of SEQ ID NO: 5 from nucleotide position 1575 to 1724, or the sequence of SEQ ID NO: 10 from nucleotide position 2559 to 2705; and ii) introducing a chimeric gene to said cell to yield a transgenic cell, wherein said chimeric gene comprises the following operably linked DNA regions:

a) a plant-expressible promoter;

b) a DNA region, which when transcribed yields an RNA molecule, capable of reducing the expression of said endogenous PARP encoding gene or cDNA; and c) a DNA region involved in transcription termination and polyadenylation wherein said RNA molecule for introduction into said cell of said plant comprises i) a sense nucleotide sequence comprising at least 100 consecutive nucleotides from said endogenous PARP encoding gene or cDNA of said plant; and ii) an antisense nucleotide sequence comprising at least 100 consecutive nucleotides from the complement of said sense nucleotide sequence;

said sense and said antisense nucleotide sequence being capable of combining into a double stranded RNA region; and wherein said vigor of said cell of said plant can be measured by measuring the capacity of explants of said plant to reduce 2,3,5-triphenyltetrazoliumchloride.

29. The method of claim 28, wherein the step of identifying an endogenous PARP encoding gene or cDNA from said plant comprises hybridizing said gene or cDNA to a probe comprising the nucleotide sequence of SEQ ID No.: 1, SEQ ID No.: 3, SEQ ID No.: 5, or SEQ ID No.: 10.

30. The method of claim 28, wherein the step of identifying an endogenous PARP encoding gene or cDNA from said plant comprises hybridizing said gene or cDNA to a probe comprising at least 20 consecutive nucleotides of a nucleotide sequence of SEQ ID No.: 1, SEQ ID No.: 3, SEQ ID No.: 5, or SEQ ID No.: 10.

31. The method of claim 28, wherein the step of identifying an endogenous PARP encoding gene or cDNA from said plant comprises hybridizing said gene or cDNA to a probe comprising the nucleotide sequence of SEQ ID No.: 1 from nucleotide position 113 to 1189, the sequence of SEQ ID No.: 3 from nucleotide position 107 to 583, the sequence of SEQ ID No.: 5 from nucleotide sequence position 131 to 542, or the sequence of SEQ ID No.: 10 from nucleotide position 81 to 1180.

32. The method of claim 1, wherein the step of identifying an endogenous PARP encoding gene or cDNA from said plant comprises performing PCR at an annealing temperature of at least 45° C. using a primer pair selected from the nucleotide sequences comprising at least 20 consecutive nucleotides of the nucleotide sequence of SEQ ID No.: 1, SEQ ID No.: 3, SEQ ID No.: 5, or SEQ ID No.: 10.

33. The method of claim 1, wherein the step of identifying an endogenous PARP encoding gene or cDNA from said plant comprises performing PCR at an annealing temperature of at least 45° C. using a primer pair selected from the following nucleotide sequences: SEQ ID No.: 13 and SEQ ID No.: 14; SEQ ID No.: 15 and SEQ ID No.: 16; SEQ ID No.: 17 and SEQ ID No.: 18; SEQ ID No.: 19 or and SEQ ID No.: 20.

34. The method of claim 1, wherein the step of identifying an endogenous PARP encoding gene or cDNA from said plant comprises performing PCR at an annealing temperature of at least 45° C. using a primer pair selected from the nucleotide sequences comprising at least 20 consecutive nucleotides of the nucleotide sequence of SEQ ID NO: 1 from nucleotide position 2558 to 2704, the sequence of SEQ ID NO: 3 from nucleotide position 1595 to 1747, the sequence of SEQ ID NO: 5 from nucleotide position 1575 to 1724, or the sequence of SEQ ID NO: 10 from nucleotide position 2559 to 2705.

35. The method of claim 28, wherein the step of identifying an endogenous PARP encoding gene or cDNA from said plant comprises hybridizing said gene or cDNA to a probe comprising the nucleotide sequence of SEQ ID NO: 1 from nucleotide position 2558 to 2704, the sequence of SEQ ID NO: 3 from nucleotide position 1595 to 1747, the sequence of SEQ ID NO: 5 from nucleotide position 1575 to 1724, or the sequence of SEQ ID NO: 10 from nucleotide position 2559 to 2705.

\* \* \* \* \*

SEQUENCE LISTING

```
<160> NUMBER OF SEQ ID NOS: 21

<210> SEQ ID NO 1
<211> LENGTH: 3211
<212> TYPE: DNA
<213> ORGANISM: Zea mays
<220> FEATURE:
<221> NAME/KEY: CDS
<222> LOCATION: (113)..(3022)
<223> OTHER INFORMATION:
```

```
<400> SEQUENCE: 1
acctacctga atacgtcatc cctaagtgtt ccgcttcctc tgtcgtccgg cctccaactc      60
catcgaaggg gctagggaga ggagggaacc cgaaccacag caggccggcg ca atg gcg     118
                                                          Met Ala
                                                            1 gcg ccg cca aag gcg tgg aag gcg gag tat gcc aag tct ggg cgg gcc      166
Ala Pro Pro Lys Ala Trp Lys Ala Glu Tyr Ala Lys Ser Gly Arg Ala
         5                  10                  15 tcg tgc aag tca tgc cgg tcc cct atc gcc aag gac cag ctc cgt ctt      214
Ser Cys Lys Ser Cys Arg Ser Pro Ile Ala Lys Asp Gln Leu Arg Leu
 20                  25                  30 ggc aag atg gtt cag gcg tca cag ttc gac ggc ttc atg ccg atg tgg      262
Gly Lys Met Val Gln Ala Ser Gln Phe Asp Gly Phe Met Pro Met Trp
 35                  40                  45                  50 aac cat gcc agc gtt gac gat gtt gaa ggg ata gat gca ctt aga tgg      310
Asn His Ala Ser Val Asp Asp Val Glu Gly Ile Asp Ala Leu Arg Trp
                 55                  60                  65 gat gat caa gag aag ata cga aac tac gtt ggg agt gcc tca gct ggt      358
Asp Asp Gln Glu Lys Ile Arg Asn Tyr Val Gly Ser Ala Ser Ala Gly
             70                  75                  80 aca agt tct aca gct gct cct cct gag aaa tgt aca att gag att gct      406
Thr Ser Ser Thr Ala Ala Pro Pro Glu Lys Cys Thr Ile Glu Ile Ala
             85                  90                  95 cca tct gcc cgt act tca tgt aga cga tgc agt gaa aag att aca aaa      454
Pro Ser Ala Arg Thr Ser Cys Arg Arg Cys Ser Glu Lys Ile Thr Lys
100                 105                 110 gga tcg gtc cgt ctt tca gct aag ctt gag agt gaa ggt ccc aag ggt      502
Gly Ser Val Arg Leu Ser Ala Lys Leu Glu Ser Glu Gly Pro Lys Gly
115                 120                 125                 130 ata cca tgg tat cat gcc aac tgt ttc ttt gag gta tcc ccg tct gca      550
Ile Pro Trp Tyr His Ala Asn Cys Phe Phe Glu Val Ser Pro Ser Ala
                135                 140                 145 act gtt gag aag ttc tca ggc tgg gat act ttg tcc gat gag gat aag      598
Thr Val Glu Lys Phe Ser Gly Trp Asp Thr Leu Ser Asp Glu Asp Lys
            150                 155                 160 aga acc atg ctc gat ctt gtt aaa aaa gat gtt ggc aac aat gaa caa      646
Arg Thr Met Leu Asp Leu Val Lys Lys Asp Val Gly Asn Asn Glu Gln
            165                 170                 175 aat aag ggt tcc aag cgc aag aaa agt gaa aat gat att gat agc tac      694
Asn Lys Gly Ser Lys Arg Lys Lys Ser Glu Asn Asp Ile Asp Ser Tyr
        180                 185                 190 aaa tcc gcc agg tta gat gaa agt aca tct gaa ggt aca gtg cga aac      742
Lys Ser Ala Arg Leu Asp Glu Ser Thr Ser Glu Gly Thr Val Arg Asn
195                 200                 205                 210 aaa ggg caa ctt gta gac cca cgt ggt tcc aat act agt tca gct gat      790
Lys Gly Gln Leu Val Asp Pro Arg Gly Ser Asn Thr Ser Ser Ala Asp
                215                 220                 225 atc caa cta aag ctt aag gag caa agt gac aca ctt tgg aag tta aag      838
Ile Gln Leu Lys Leu Lys Glu Gln Ser Asp Thr Leu Trp Lys Leu Lys
            230                 235                 240 gat gga ctt aag act cat gta tcg gct gct gaa tta agg gat atg ctt      886
Asp Gly Leu Lys Thr His Val Ser Ala Ala Glu Leu Arg Asp Met Leu
            245                 250                 255 gag gct aat ggg cag gat aca tca gga cca gaa agg cac cta ttg gat      934
Glu Ala Asn Gly Gln Asp Thr Ser Gly Pro Glu Arg His Leu Leu Asp
        260                 265                 270 cgc tgt gcg gat gga atg ata ttt gga gcg ctg ggt cct tgc cca gtc      982
Arg Cys Ala Asp Gly Met Ile Phe Gly Ala Leu Gly Pro Cys Pro Val
275                 280                 285                 290
```

```
tgt gct aat ggc atg tac tat tat aat ggt cag tac caa tgc agt ggt    1030
Cys Ala Asn Gly Met Tyr Tyr Tyr Asn Gly Gln Tyr Gln Cys Ser Gly
            295                 300                 305 aat gtg tca gag tgg tcc aag tgt aca tac tct gcc aca gaa cct gtc    1078
Asn Val Ser Glu Trp Ser Lys Cys Thr Tyr Ser Ala Thr Glu Pro Val
        310                 315                 320 cgc gtt aag aag aag tgg caa att cca cat gga aca aag aat gat tac    1126
Arg Val Lys Lys Lys Trp Gln Ile Pro His Gly Thr Lys Asn Asp Tyr
    325                 330                 335 ctt atg aag tgg ttc aaa tct caa aag gtt aag aaa cca gag agg gtt    1174
Leu Met Lys Trp Phe Lys Ser Gln Lys Val Lys Lys Pro Glu Arg Val
340                 345                 350 ctt cca cca atg tca cct gag aaa tct gga agt aaa gca act cag aga    1222
Leu Pro Pro Met Ser Pro Glu Lys Ser Gly Ser Lys Ala Thr Gln Arg
355                 360                 365                 370 aca tca ttg ctg tct tct aaa ggg ttg gat aaa tta agg ttt tct gtt    1270
Thr Ser Leu Leu Ser Ser Lys Gly Leu Asp Lys Leu Arg Phe Ser Val
            375                 380                 385 gta gga caa tca aaa gaa gca gca aat gag tgg att gag aag ctc aaa    1318
Val Gly Gln Ser Lys Glu Ala Ala Asn Glu Trp Ile Glu Lys Leu Lys
        390                 395                 400 ctt gct ggt gcc aac ttc tat gcc agg gtt gtc aaa gat att gat tgt    1366
Leu Ala Gly Ala Asn Phe Tyr Ala Arg Val Val Lys Asp Ile Asp Cys
    405                 410                 415 tta att gca tgt ggt gag ctc gac aat gaa aat gct gaa gtc agg aaa    1414
Leu Ile Ala Cys Gly Glu Leu Asp Asn Glu Asn Ala Glu Val Arg Lys
420                 425                 430 gca agg agg ctg aag ata cca att gta agg gag ggt tac att gga gaa    1462
Ala Arg Arg Leu Lys Ile Pro Ile Val Arg Glu Gly Tyr Ile Gly Glu
435                 440                 445                 450 tgt gtt aaa aag aac aaa atg ctg cca ttt gat ttg tat aaa cta gag    1510
Cys Val Lys Lys Asn Lys Met Leu Pro Phe Asp Leu Tyr Lys Leu Glu
            455                 460                 465 aat gcc tta gag tcc tca aaa ggc agt act gtc act gtt aaa gtt aag    1558
Asn Ala Leu Glu Ser Ser Lys Gly Ser Thr Val Thr Val Lys Val Lys
        470                 475                 480 ggc cga agt gct gtt cat gag tcc tct ggt ttg caa gat act gct cac    1606
Gly Arg Ser Ala Val His Glu Ser Ser Gly Leu Gln Asp Thr Ala His
    485                 490                 495 att ctt gaa gat ggg aaa agc ata tac aat gca acc tta aac atg tct    1654
Ile Leu Glu Asp Gly Lys Ser Ile Tyr Asn Ala Thr Leu Asn Met Ser
500                 505                 510 gac ctg gca cta ggt gtg aac agc tac tat gta ctc cag atc att gaa    1702
Asp Leu Ala Leu Gly Val Asn Ser Tyr Tyr Val Leu Gln Ile Ile Glu
515                 520                 525                 530 cag gat gat ggg tct gag tgc tac gta ttt cgt aag tgg gga cgg gtt    1750
Gln Asp Asp Gly Ser Glu Cys Tyr Val Phe Arg Lys Trp Gly Arg Val
            535                 540                 545 ggg agt gag aaa att gga ggg caa aaa ctg gag gag atg tca aaa act    1798
Gly Ser Glu Lys Ile Gly Gly Gln Lys Leu Glu Glu Met Ser Lys Thr
        550                 555                 560 gag gca atc aag gaa ttc aaa aga tta ttt ctt gag aag act gga aac    1846
Glu Ala Ile Lys Glu Phe Lys Arg Leu Phe Leu Glu Lys Thr Gly Asn
    565                 570                 575 tca tgg gaa gct tgg gaa tgt aaa acc aat ttt cgg aag cag cct ggg    1894
Ser Trp Glu Ala Trp Glu Cys Lys Thr Asn Phe Arg Lys Gln Pro Gly
580                 585                 590 aga ttt tac cca ctt gat gtt gat tat ggt gtt aag aaa gca cca aaa    1942
Arg Phe Tyr Pro Leu Asp Val Asp Tyr Gly Val Lys Lys Ala Pro Lys
595                 600                 605                 610
```

```
cgg aaa gat atc agt gaa atg aaa agt tct ctt gct cct caa ttg cta      1990
Arg Lys Asp Ile Ser Glu Met Lys Ser Ser Leu Ala Pro Gln Leu Leu
            615                 620                 625 gaa ctc atg aag atg ctt ttc aat gtg gag aca tat aga gct gct atg      2038
Glu Leu Met Lys Met Leu Phe Asn Val Glu Thr Tyr Arg Ala Ala Met
        630                 635                 640 atg gaa ttt gaa att aat atg tca gaa atg cct ctt ggg aag cta agc      2086
Met Glu Phe Glu Ile Asn Met Ser Glu Met Pro Leu Gly Lys Leu Ser
    645                 650                 655 aag gaa aat att gag aaa gga ttt gaa gca tta act gag ata cag aat      2134
Lys Glu Asn Ile Glu Lys Gly Phe Glu Ala Leu Thr Glu Ile Gln Asn
660                 665                 670 tta ttg aag gac acc gct gat caa gca ctg gct gtt aga gaa agc tta      2182
Leu Leu Lys Asp Thr Ala Asp Gln Ala Leu Ala Val Arg Glu Ser Leu
675                 680                 685                 690 att gtt gct gcg agc aat cgc ttt ttc act ctt atc cct tct att cat      2230
Ile Val Ala Ala Ser Asn Arg Phe Phe Thr Leu Ile Pro Ser Ile His
                695                 700                 705 cct cat att ata cgg gat gag gat gat ttg atg atc aaa gcg aaa atg      2278
Pro His Ile Ile Arg Asp Glu Asp Asp Leu Met Ile Lys Ala Lys Met
            710                 715                 720 ctt gaa gct ctg cag gat att gaa att gct tca aag ata gtt ggc ttc      2326
Leu Glu Ala Leu Gln Asp Ile Glu Ile Ala Ser Lys Ile Val Gly Phe
        725                 730                 735 gat agc gac agt gat gaa tct ctt gat gat aaa tat atg aaa ctt cac      2374
Asp Ser Asp Ser Asp Glu Ser Leu Asp Asp Lys Tyr Met Lys Leu His
    740                 745                 750 tgt gac atc acc ccg ctg gct cac gat agt gaa gat tac aag tta att      2422
Cys Asp Ile Thr Pro Leu Ala His Asp Ser Glu Asp Tyr Lys Leu Ile
755                 760                 765                 770 gag cag tat ctc ctc aac aca cat gct cct act cac aag gac tgg tcg      2470
Glu Gln Tyr Leu Leu Asn Thr His Ala Pro Thr His Lys Asp Trp Ser
                775                 780                 785 ctg gaa ctg gag gaa gtt ttt tca ctt gat cga gat gga gaa ctt aat      2518
Leu Glu Leu Glu Glu Val Phe Ser Leu Asp Arg Asp Gly Glu Leu Asn
            790                 795                 800 aag tac tca aga tat aaa aat aat ctg cat aac aag atg cta tta tgg      2566
Lys Tyr Ser Arg Tyr Lys Asn Asn Leu His Asn Lys Met Leu Leu Trp
        805                 810                 815 cac ggt tca agg ttg acg aat ttt gtg gga att ctt agt caa ggg cta      2614
His Gly Ser Arg Leu Thr Asn Phe Val Gly Ile Leu Ser Gln Gly Leu
    820                 825                 830 aga att gca cct cct gag gca cct gtt act ggc tat atg ttc ggc aaa      2662
Arg Ile Ala Pro Pro Glu Ala Pro Val Thr Gly Tyr Met Phe Gly Lys
835                 840                 845                 850 ggc ctc tac ttt gca gat cta gta agc aag agc gca caa tac tgt tat      2710
Gly Leu Tyr Phe Ala Asp Leu Val Ser Lys Ser Ala Gln Tyr Cys Tyr
                855                 860                 865 gtg gat agg aat aat cct gta ggt ttg atg ctt ctt tct gag gtt gct      2758
Val Asp Arg Asn Asn Pro Val Gly Leu Met Leu Leu Ser Glu Val Ala
            870                 875                 880 tta gga gac atg tat gaa cta aag aaa gcc acg tcc atg gac aaa cct      2806
Leu Gly Asp Met Tyr Glu Leu Lys Lys Ala Thr Ser Met Asp Lys Pro
        885                 890                 895 cca aga ggg aag cat tcg acc aag gga tta ggc aaa acc gtg cca ctg      2854
Pro Arg Gly Lys His Ser Thr Lys Gly Leu Gly Lys Thr Val Pro Leu
    900                 905                 910 gag tca gag ttt gtg aag tgg agg gat gat gtc gta gtt ccc tgc ggc      2902
Glu Ser Glu Phe Val Lys Trp Arg Asp Asp Val Val Val Pro Cys Gly
915                 920                 925                 930
```

-continued

```
aag ccg gtg cca tca tca att agg agc tct gaa ctc atg tac aat gag    2950
Lys Pro Val Pro Ser Ser Ile Arg Ser Ser Glu Leu Met Tyr Asn Glu
            935                 940                 945 tac atc gtc tac aac aca tcc cag gtg aag atg cag ttc ttg ctg aag    2998
Tyr Ile Val Tyr Asn Thr Ser Gln Val Lys Met Gln Phe Leu Leu Lys
        950                 955                 960 gtg cgt ttc cat cac aag agg tag ctgggagact aggcaagtag agttggaagg   3052
Val Arg Phe His His Lys Arg
                965 tagagaagca gagttaggcg atgcctcttt tggtattatt agtaagcctg gcatgtattt   3112 atgggtgctc gcgcttgatc cattttggta agtgttgctt gggcatcagc gcgaatagca   3172 ccaatcacac acttttacct aatgacgttt tactgtata                          3211

<210> SEQ ID NO 2
<211> LENGTH: 969
<212> TYPE: PRT
<213> ORGANISM: Zea mays

<400> SEQUENCE: 2

Met Ala Ala Pro Pro Lys Ala Trp Lys Ala Glu Tyr Ala Lys Ser Gly
1               5                   10                  15

Arg Ala Ser Cys Lys Ser Cys Arg Ser Pro Ile Ala Lys Asp Gln Leu
            20                  25                  30

Arg Leu Gly Lys Met Val Gln Ala Ser Gln Phe Asp Gly Phe Met Pro
        35                  40                  45

Met Trp Asn His Ala Ser Val Asp Asp Val Glu Gly Ile Asp Ala Leu
    50                  55                  60

Arg Trp Asp Asp Gln Glu Lys Ile Arg Asn Tyr Val Gly Ser Ala Ser
65                  70                  75                  80

Ala Gly Thr Ser Ser Thr Ala Ala Pro Pro Glu Lys Cys Thr Ile Glu
                85                  90                  95

Ile Ala Pro Ser Ala Arg Thr Ser Cys Arg Arg Cys Ser Glu Lys Ile
            100                 105                 110

Thr Lys Gly Ser Val Arg Leu Ser Ala Lys Leu Glu Ser Glu Gly Pro
        115                 120                 125

Lys Gly Ile Pro Trp Tyr His Ala Asn Cys Phe Phe Glu Val Ser Pro
    130                 135                 140

Ser Ala Thr Val Glu Lys Phe Ser Gly Trp Asp Thr Leu Ser Asp Glu
145                 150                 155                 160

Asp Lys Arg Thr Met Leu Asp Leu Val Lys Lys Asp Val Gly Asn Asn
                165                 170                 175

Glu Gln Asn Lys Gly Ser Lys Arg Lys Lys Ser Glu Asn Asp Ile Asp
            180                 185                 190

Ser Tyr Lys Ser Ala Arg Leu Asp Glu Ser Thr Ser Glu Gly Thr Val
        195                 200                 205

Arg Asn Lys Gly Gln Leu Val Asp Pro Arg Gly Ser Asn Thr Ser Ser
    210                 215                 220

Ala Asp Ile Gln Leu Lys Leu Lys Glu Gln Ser Asp Thr Leu Trp Lys
225                 230                 235                 240

Leu Lys Asp Gly Leu Lys Thr His Val Ser Ala Ala Glu Leu Arg Asp
                245                 250                 255

Met Leu Glu Ala Asn Gly Gln Asp Thr Ser Gly Pro Glu Arg His Leu
            260                 265                 270

Leu Asp Arg Cys Ala Asp Gly Met Ile Phe Gly Ala Leu Gly Pro Cys
        275                 280                 285
```

-continued

```
Pro Val Cys Ala Asn Gly Met Tyr Tyr Tyr Asn Gly Gln Tyr Gln Cys
    290                 295                 300

Ser Gly Asn Val Ser Glu Trp Ser Lys Cys Thr Tyr Ser Ala Thr Glu
305                 310                 315                 320

Pro Val Arg Val Lys Lys Trp Gln Ile Pro His Gly Thr Lys Asn
                325                 330                 335

Asp Tyr Leu Met Lys Trp Phe Lys Ser Gln Lys Val Lys Lys Pro Glu
            340                 345                 350

Arg Val Leu Pro Pro Met Ser Pro Glu Lys Ser Gly Ser Lys Ala Thr
        355                 360                 365

Gln Arg Thr Ser Leu Leu Ser Ser Lys Gly Leu Asp Lys Leu Arg Phe
    370                 375                 380

Ser Val Val Gly Gln Ser Lys Glu Ala Ala Asn Glu Trp Ile Glu Lys
385                 390                 395                 400

Leu Lys Leu Ala Gly Ala Asn Phe Tyr Ala Arg Val Val Lys Asp Ile
                405                 410                 415

Asp Cys Leu Ile Ala Cys Gly Glu Leu Asp Asn Glu Asn Ala Glu Val
            420                 425                 430

Arg Lys Ala Arg Arg Leu Lys Ile Pro Ile Val Arg Glu Gly Tyr Ile
        435                 440                 445

Gly Glu Cys Val Lys Lys Asn Lys Met Leu Pro Phe Asp Leu Tyr Lys
    450                 455                 460

Leu Glu Asn Ala Leu Glu Ser Ser Lys Gly Ser Thr Val Thr Val Lys
465                 470                 475                 480

Val Lys Gly Arg Ser Ala Val His Glu Ser Ser Gly Leu Gln Asp Thr
                485                 490                 495

Ala His Ile Leu Glu Asp Gly Lys Ser Ile Tyr Asn Ala Thr Leu Asn
            500                 505                 510

Met Ser Asp Leu Ala Leu Gly Val Asn Ser Tyr Tyr Val Leu Gln Ile
        515                 520                 525

Ile Glu Gln Asp Asp Gly Ser Glu Cys Tyr Val Phe Arg Lys Trp Gly
    530                 535                 540

Arg Val Gly Ser Glu Lys Ile Gly Gly Gln Lys Leu Glu Glu Met Ser
545                 550                 555                 560

Lys Thr Glu Ala Ile Lys Glu Phe Lys Arg Leu Phe Leu Glu Lys Thr
                565                 570                 575

Gly Asn Ser Trp Glu Ala Trp Glu Cys Lys Thr Asn Phe Arg Lys Gln
            580                 585                 590

Pro Gly Arg Phe Tyr Pro Leu Asp Val Asp Tyr Gly Val Lys Lys Ala
        595                 600                 605

Pro Lys Arg Lys Asp Ile Ser Glu Met Lys Ser Ser Leu Ala Pro Gln
    610                 615                 620

Leu Leu Glu Leu Met Lys Met Leu Phe Asn Val Glu Thr Tyr Arg Ala
625                 630                 635                 640

Ala Met Met Glu Phe Glu Ile Asn Met Ser Glu Met Pro Leu Gly Lys
                645                 650                 655

Leu Ser Lys Glu Asn Ile Glu Lys Gly Phe Glu Ala Leu Thr Glu Ile
            660                 665                 670

Gln Asn Leu Leu Lys Asp Thr Ala Asp Gln Ala Leu Ala Val Arg Glu
        675                 680                 685

Ser Leu Ile Val Ala Ala Ser Asn Arg Phe Phe Thr Leu Ile Pro Ser
    690                 695                 700

Ile His Pro His Ile Ile Arg Asp Glu Asp Leu Met Ile Lys Ala
705                 710                 715                 720
```

```
Lys Met Leu Glu Ala Leu Gln Asp Ile Glu Ile Ala Ser Lys Ile Val
            725                 730                 735

Gly Phe Asp Ser Asp Ser Asp Glu Ser Leu Asp Asp Lys Tyr Met Lys
            740                 745                 750

Leu His Cys Asp Ile Thr Pro Leu Ala His Asp Ser Glu Asp Tyr Lys
            755                 760                 765

Leu Ile Glu Gln Tyr Leu Leu Asn Thr His Ala Pro Thr His Lys Asp
        770                 775                 780

Trp Ser Leu Glu Leu Glu Glu Val Phe Ser Leu Asp Arg Asp Gly Glu
785                 790                 795                 800

Leu Asn Lys Tyr Ser Arg Tyr Lys Asn Asn Leu His Asn Lys Met Leu
                805                 810                 815

Leu Trp His Gly Ser Arg Leu Thr Asn Phe Val Gly Ile Leu Ser Gln
            820                 825                 830

Gly Leu Arg Ile Ala Pro Pro Glu Ala Pro Val Thr Gly Tyr Met Phe
        835                 840                 845

Gly Lys Gly Leu Tyr Phe Ala Asp Leu Val Ser Lys Ser Ala Gln Tyr
    850                 855                 860

Cys Tyr Val Asp Arg Asn Asn Pro Val Gly Leu Met Leu Leu Ser Glu
865                 870                 875                 880

Val Ala Leu Gly Asp Met Tyr Glu Leu Lys Lys Ala Thr Ser Met Asp
                885                 890                 895

Lys Pro Pro Arg Gly Lys His Ser Thr Lys Gly Leu Gly Lys Thr Val
            900                 905                 910

Pro Leu Glu Ser Glu Phe Val Lys Trp Arg Asp Asp Val Val Val Pro
        915                 920                 925

Cys Gly Lys Pro Val Pro Ser Ser Ile Arg Ser Ser Glu Leu Met Tyr
    930                 935                 940

Asn Glu Tyr Ile Val Tyr Asn Thr Ser Gln Val Lys Met Gln Phe Leu
945                 950                 955                 960

Leu Lys Val Arg Phe His His Lys Arg
                965

<210> SEQ ID NO 3
<211> LENGTH: 2295
<212> TYPE: DNA
<213> ORGANISM: Zea mays
<220> FEATURE:
<221> NAME/KEY: CDS
<222> LOCATION: (107)..(2068)
<223> OTHER INFORMATION:

<400> SEQUENCE: 3
tgacctgttc catcccgcca gcccttccgc tcccacgacc caaccccact gcccggagcc      60
cccgagcctt ctcgaatctt gcgagaaccc caggggcgag gagcag atg tcg gcg         115
                                                  Met Ser Ala
                                                   1 agg cta cgg gtg gcg gac gtc cgc gcg gag ctt cag cgc cgc ggc ctc       163
Arg Leu Arg Val Ala Asp Val Arg Ala Glu Leu Gln Arg Arg Gly Leu
  5                  10                  15 gat gta tcc ggc acc aag cct gct ctc gtg cgg agg ctg gac gcc gca       211
Asp Val Ser Gly Thr Lys Pro Ala Leu Val Arg Arg Leu Asp Ala Ala
 20                  25                  30                  35 att tgc gag gcg gag aag gcc gtg gtg gct gct gcg cca acc agt gtg       259
Ile Cys Glu Ala Glu Lys Ala Val Val Ala Ala Ala Pro Thr Ser Val
                 40                  45                  50 gca aat ggg tat gac gta gcc gta gat ggc aaa agg aac tgc ggg aat       307
```

-continued

```
        Ala Asn Gly Tyr Asp Val Ala Val Asp Gly Lys Arg Asn Cys Gly Asn
                     55                  60                  65 aat aag agg aaa agg tcc ggg gat ggg ggt gaa gag gga aac ggc gat          355
Asn Lys Arg Lys Arg Ser Gly Asp Gly Gly Glu Glu Gly Asn Gly Asp
         70                  75                  80 acg tgt aca gat gtg aca aaa cta gag ggc atg agc tat cgt gag ctg          403
Thr Cys Thr Asp Val Thr Lys Leu Glu Gly Met Ser Tyr Arg Glu Leu
 85                  90                  95 cag gga ttg gcc aag gca cgt gga gtt gcg gca aat ggg ggc aag aaa          451
Gln Gly Leu Ala Lys Ala Arg Gly Val Ala Ala Asn Gly Gly Lys Lys
100                 105                 110                 115 gat gtt atc cag agg ttg ctc tcg gcg act gct ggt cct gct gca gtt          499
Asp Val Ile Gln Arg Leu Leu Ser Ala Thr Ala Gly Pro Ala Ala Val
                120                 125                 130 gca gat ggt ggt cct ctg ggc gcc aag gaa gtc ata aaa ggt ggt gat          547
Ala Asp Gly Gly Pro Leu Gly Ala Lys Glu Val Ile Lys Gly Gly Asp
            135                 140                 145 gag gag gtt gag gtg aaa aag gag aag atg gtt act gcc acg aag aag          595
Glu Glu Val Glu Val Lys Lys Glu Lys Met Val Thr Ala Thr Lys Lys
        150                 155                 160 gga gct gca gtg ctg gat cag cac att ccc gat cac ata aaa gtg aac          643
Gly Ala Ala Val Leu Asp Gln His Ile Pro Asp His Ile Lys Val Asn
165                 170                 175 tat cat gtc ttg caa gtg ggc gat gaa atc tat gat gcc acc ttg aac          691
Tyr His Val Leu Gln Val Gly Asp Glu Ile Tyr Asp Ala Thr Leu Asn
180                 185                 190                 195 cag act aat gtt gga gac aac aac aat aag ttc tat atc att caa gtt          739
Gln Thr Asn Val Gly Asp Asn Asn Asn Lys Phe Tyr Ile Ile Gln Val
                200                 205                 210 tta gaa tct gat gct ggt gga agc ttt atg gtt tac aat aga tgg gga          787
Leu Glu Ser Asp Ala Gly Gly Ser Phe Met Val Tyr Asn Arg Trp Gly
            215                 220                 225 aga gtt ggg gta cga ggt caa gat aaa cta cat ggt ccc tcc cca aca          835
Arg Val Gly Val Arg Gly Gln Asp Lys Leu His Gly Pro Ser Pro Thr
        230                 235                 240 cga gac caa gca ata tat gaa ttt gag ggg aag ttc cac aac aaa acc          883
Arg Asp Gln Ala Ile Tyr Glu Phe Glu Gly Lys Phe His Asn Lys Thr
245                 250                 255 aat aat cat tgg tct gat cgc aag aac ttc aaa tgt tat gca aag aaa          931
Asn Asn His Trp Ser Asp Arg Lys Asn Phe Lys Cys Tyr Ala Lys Lys
260                 265                 270                 275 tac act tgg ctt gaa atg gat tat ggt gaa act gag aaa gaa ata gag          979
Tyr Thr Trp Leu Glu Met Asp Tyr Gly Glu Thr Glu Lys Glu Ile Glu
                280                 285                 290 aaa ggt tcc att act gat cag ata aaa gag aca aaa ctt gaa act aga         1027
Lys Gly Ser Ile Thr Asp Gln Ile Lys Glu Thr Lys Leu Glu Thr Arg
            295                 300                 305 att gcg cag ttc ata tcc ctg atc tgc aat att agc atg atg aag caa         1075
Ile Ala Gln Phe Ile Ser Leu Ile Cys Asn Ile Ser Met Met Lys Gln
        310                 315                 320 aga atg gtg gaa ata ggt tat aat gct gaa aag ctt ccc ctt gga aag         1123
Arg Met Val Glu Ile Gly Tyr Asn Ala Glu Lys Leu Pro Leu Gly Lys
325                 330                 335 cta agg aaa gct aca ata ctt aag ggt tat cat gtt ttg aaa agg ata         1171
Leu Arg Lys Ala Thr Ile Leu Lys Gly Tyr His Val Leu Lys Arg Ile
340                 345                 350                 355 tcc gat gtt att tca aag gcg gac agg aga cat ctt gag caa ttg act         1219
Ser Asp Val Ile Ser Lys Ala Asp Arg Arg His Leu Glu Gln Leu Thr
                360                 365                 370 ggg gaa ttc tac acc gtg att cct cat gac ttt ggt ttc aga aag atg         1267
```

```
                Gly Glu Phe Tyr Thr Val Ile Pro His Asp Phe Gly Phe Arg Lys Met
                            375                 380                 385 cgt gaa ttt att atc gat act cct cag aaa cta aaa gct aag ctg gag           1315
Arg Glu Phe Ile Ile Asp Thr Pro Gln Lys Leu Lys Ala Lys Leu Glu
            390                 395                 400 atg gtt gaa gcc ctt ggt gag att gaa att gca act aaa ctt ttg gag           1363
Met Val Glu Ala Leu Gly Glu Ile Glu Ile Ala Thr Lys Leu Leu Glu
405                 410                 415 gat gat tca agt gac cag gat gat ccg ttg tat gct cga tac aag caa           1411
Asp Asp Ser Ser Asp Gln Asp Asp Pro Leu Tyr Ala Arg Tyr Lys Gln
420                 425                 430                 435 ctt cat tgt gat ttc aca cct ctt gaa gct gat tca gat gag tac tct           1459
Leu His Cys Asp Phe Thr Pro Leu Glu Ala Asp Ser Asp Glu Tyr Ser
            440                 445                 450 atg ata aaa tca tat ttg aga aat aca cat gga aaa aca cac tct ggt           1507
Met Ile Lys Ser Tyr Leu Arg Asn Thr His Gly Lys Thr His Ser Gly
                455                 460                 465 tat acg gtg gac ata gtg caa ata ttt aag gtt tca agg cat ggt gaa           1555
Tyr Thr Val Asp Ile Val Gln Ile Phe Lys Val Ser Arg His Gly Glu
            470                 475                 480 aca gag cga ttt caa aaa ttt gct agt aca aga aat agg atg ctt ttg           1603
Thr Glu Arg Phe Gln Lys Phe Ala Ser Thr Arg Asn Arg Met Leu Leu
485                 490                 495 tgg cat ggt tct cgg ttg agc aac tgg gct ggg atc ctt tct cag ggt           1651
Trp His Gly Ser Arg Leu Ser Asn Trp Ala Gly Ile Leu Ser Gln Gly
500                 505                 510                 515 ctg cga atc gct cct cct gaa gca cct gtt act ggt tac atg ttt ggc           1699
Leu Arg Ile Ala Pro Pro Glu Ala Pro Val Thr Gly Tyr Met Phe Gly
            520                 525                 530 aag ggt gtt tac ttt gct gac atg ttt tca aag agt gca aac tat tgc           1747
Lys Gly Val Tyr Phe Ala Asp Met Phe Ser Lys Ser Ala Asn Tyr Cys
                535                 540                 545 tac gcc tct gaa gca tgt aga tct gga gta ctg ctt tta tgt gag gtt           1795
Tyr Ala Ser Glu Ala Cys Arg Ser Gly Val Leu Leu Leu Cys Glu Val
            550                 555                 560 gca ttg ggc gat atg aat gag cta ctg aat gca gat tac gat gct aat           1843
Ala Leu Gly Asp Met Asn Glu Leu Leu Asn Ala Asp Tyr Asp Ala Asn
565                 570                 575 aac ctg ccc aaa gga aaa tta aga tcc aag gga gtt ggt caa aca gca           1891
Asn Leu Pro Lys Gly Lys Leu Arg Ser Lys Gly Val Gly Gln Thr Ala
580                 585                 590                 595 cct aac atg gtc gag tct aag gtc gct gac gat ggt gtt gtt gtt ccc           1939
Pro Asn Met Val Glu Ser Lys Val Ala Asp Asp Gly Val Val Val Pro
                600                 605                 610 ctt ggc gaa ccc aaa cag gaa cct tcc aaa agg ggt ggc ttg ctt tat           1987
Leu Gly Glu Pro Lys Gln Glu Pro Ser Lys Arg Gly Gly Leu Leu Tyr
            615                 620                 625 aat gag tac ata gtg tac aac gta gac cag ata aga atg cgg tat gtc           2035
Asn Glu Tyr Ile Val Tyr Asn Val Asp Gln Ile Arg Met Arg Tyr Val
                630                 635                 640 tta cat gtt aac ttc aat ttc aag aga cgg tag atgttgcaaa gagctgaaac        2088
Leu His Val Asn Phe Asn Phe Lys Arg Arg
            645                 650 tgttgctgag atcttagcag aacatatgtg gacttatagc accaggtgcc ctcagcctca         2148
ttttctgagc aaatttggta gcctttgcat ttcgattttg gttcagctt ctagcccat           2208 tgatgattga tactgagtgt atatatgaac cattgatatc caccttccat gtacttaagt         2268 tttttttaaca tgtcccatgc ataataa                                             2295
```

```
<210> SEQ ID NO 4
<211> LENGTH: 653
<212> TYPE: PRT
<213> ORGANISM: Zea mays

<400> SEQUENCE: 4

Met Ser Ala Arg Leu Arg Val Ala Asp Val Arg Ala Glu Leu Gln Arg
1               5                   10                  15

Arg Gly Leu Asp Val Ser Gly Thr Lys Pro Ala Leu Val Arg Arg Leu
            20                  25                  30

Asp Ala Ala Ile Cys Glu Ala Glu Lys Ala Val Val Ala Ala Ala Pro
        35                  40                  45

Thr Ser Val Ala Asn Gly Tyr Asp Val Ala Val Asp Gly Lys Arg Asn
    50                  55                  60

Cys Gly Asn Asn Lys Arg Lys Ser Gly Asp Gly Gly Glu Glu Gly
65                  70                  75                  80

Asn Gly Asp Thr Cys Thr Asp Val Thr Lys Leu Glu Gly Met Ser Tyr
                85                  90                  95

Arg Glu Leu Gln Gly Leu Ala Lys Ala Arg Gly Val Ala Ala Asn Gly
            100                 105                 110

Gly Lys Lys Asp Val Ile Gln Arg Leu Leu Ser Ala Thr Ala Gly Pro
        115                 120                 125

Ala Ala Val Ala Asp Gly Gly Pro Leu Gly Ala Lys Glu Val Ile Lys
    130                 135                 140

Gly Gly Asp Glu Glu Val Glu Val Lys Lys Glu Lys Met Val Thr Ala
145                 150                 155                 160

Thr Lys Lys Gly Ala Ala Val Leu Asp Gln His Ile Pro Asp His Ile
                165                 170                 175

Lys Val Asn Tyr His Val Leu Gln Val Gly Asp Glu Ile Tyr Asp Ala
            180                 185                 190

Thr Leu Asn Gln Thr Asn Val Gly Asp Asn Asn Lys Phe Tyr Ile
        195                 200                 205

Ile Gln Val Leu Glu Ser Asp Ala Gly Gly Ser Phe Met Val Tyr Asn
    210                 215                 220

Arg Trp Gly Arg Val Gly Val Arg Gly Gln Asp Lys Leu His Gly Pro
225                 230                 235                 240

Ser Pro Thr Arg Asp Gln Ala Ile Tyr Glu Phe Glu Gly Lys Phe His
                245                 250                 255

Asn Lys Thr Asn Asn His Trp Ser Asp Arg Lys Asn Phe Lys Cys Tyr
            260                 265                 270

Ala Lys Lys Tyr Thr Trp Leu Glu Met Asp Tyr Gly Glu Thr Glu Lys
        275                 280                 285

Glu Ile Glu Lys Gly Ser Ile Thr Asp Gln Ile Lys Thr Lys Leu
    290                 295                 300

Glu Thr Arg Ile Ala Gln Phe Ile Ser Leu Ile Cys Asn Ile Ser Met
305                 310                 315                 320

Met Lys Gln Arg Met Val Glu Ile Gly Tyr Asn Ala Glu Lys Leu Pro
                325                 330                 335

Leu Gly Lys Leu Arg Lys Ala Thr Ile Leu Lys Gly Tyr His Val Leu
            340                 345                 350

Lys Arg Ile Ser Asp Val Ile Ser Lys Ala Asp Arg Arg His Leu Glu
        355                 360                 365

Gln Leu Thr Gly Glu Phe Tyr Thr Val Ile Pro His Asp Phe Gly Phe
    370                 375                 380

Arg Lys Met Arg Glu Phe Ile Ile Asp Thr Pro Gln Lys Leu Lys Ala
```

```
                                385                 390                 395                 400

Lys Leu Glu Met Val Glu Ala Leu Gly Glu Ile Glu Ile Ala Thr Lys
                    405                 410                 415

Leu Leu Glu Asp Ser Ser Asp Gln Asp Pro Leu Tyr Ala Arg
                420                 425                 430

Tyr Lys Gln Leu His Cys Asp Phe Thr Pro Leu Glu Ala Asp Ser Asp
            435                 440                 445

Glu Tyr Ser Met Ile Lys Ser Tyr Leu Arg Asn Thr His Gly Lys Thr
        450                 455                 460

His Ser Gly Tyr Thr Val Asp Ile Val Gln Ile Phe Lys Val Ser Arg
465                 470                 475                 480

His Gly Glu Thr Glu Arg Phe Gln Lys Phe Ala Ser Thr Arg Asn Arg
                485                 490                 495

Met Leu Leu Trp His Gly Ser Arg Leu Ser Asn Trp Ala Gly Ile Leu
                500                 505                 510

Ser Gln Gly Leu Arg Ile Ala Pro Pro Glu Ala Pro Val Thr Gly Tyr
            515                 520                 525

Met Phe Gly Lys Gly Val Tyr Phe Ala Asp Met Phe Ser Lys Ser Ala
        530                 535                 540

Asn Tyr Cys Tyr Ala Ser Glu Ala Cys Arg Ser Gly Val Leu Leu Leu
545                 550                 555                 560

Cys Glu Val Ala Leu Gly Asp Met Asn Glu Leu Leu Asn Ala Asp Tyr
                565                 570                 575

Asp Ala Asn Asn Leu Pro Lys Gly Lys Leu Arg Ser Lys Gly Val Gly
            580                 585                 590

Gln Thr Ala Pro Asn Met Val Glu Ser Lys Val Ala Asp Asp Gly Val
        595                 600                 605

Val Val Pro Leu Gly Glu Pro Lys Gln Glu Pro Ser Lys Arg Gly Gly
610                 615                 620

Leu Leu Tyr Asn Glu Tyr Ile Val Tyr Asn Val Asp Gln Ile Arg Met
625                 630                 635                 640

Arg Tyr Val Leu His Val Asn Phe Asn Phe Lys Arg Arg
                645                 650

<210> SEQ ID NO 5
<211> LENGTH: 2147
<212> TYPE: DNA
<213> ORGANISM: Arabidopsis thaliana
<220> FEATURE:
<221> NAME/KEY: CDS
<222> LOCATION: (129)..(2042)
<223> OTHER INFORMATION:

<400> SEQUENCE: 5
attgatgaag aagaaaacga agaagaagac tcttcaaatg ctcgcgcgaa ctcacttctg      60
acgaaaacca tacttcctca gtctcattcc ctttccgacg aactattctc ctgaagaaga     120 agacgaaa atg gcg aac aag ctc aaa gtc gac gaa ctc cgt tta aaa ctc      170
         Met Ala Asn Lys Leu Lys Val Asp Glu Leu Arg Leu Lys Leu
           1               5                   10 gcc gag cgt gga ctc agt act act gga gtc aaa gcc gtt ctg gtg gag       218
Ala Glu Arg Gly Leu Ser Thr Thr Gly Val Lys Ala Val Leu Val Glu
 15              20                  25                  30 agg ctt gaa gag gct atc gca gaa gac act aag aag gaa gaa tca aag       266
Arg Leu Glu Glu Ala Ile Ala Glu Asp Thr Lys Lys Glu Glu Ser Lys
             35                  40                  45 agc aag agg aaa aga aat tct tct aat gat act tat gaa tcg aac aaa       314
Ser Lys Arg Lys Arg Asn Ser Ser Asn Asp Thr Tyr Glu Ser Asn Lys
```

-continued

```
                 50                  55                  60
ttg att gca att ggc gaa ttt cgt ggg atg att gtg aag gaa ttg cgt     362
Leu Ile Ala Ile Gly Glu Phe Arg Gly Met Ile Val Lys Glu Leu Arg
         65                  70                  75 gag gaa gct att aag aga ggc tta gat aca aca gga acc aaa aag gat     410
Glu Glu Ala Ile Lys Arg Gly Leu Asp Thr Thr Gly Thr Lys Lys Asp
 80                  85                  90 ctt ctt gag agg ctt tgc aat gat gct aat aac gtt tcc aat gca cca     458
Leu Leu Glu Arg Leu Cys Asn Asp Ala Asn Asn Val Ser Asn Ala Pro
 95                 100                 105                 110 gtc aaa tcc agt aat ggg aca gat gaa gct gaa gat gac aac aat ggc     506
Val Lys Ser Ser Asn Gly Thr Asp Glu Ala Glu Asp Asp Asn Asn Gly
             115                 120                 125 ttt gaa gaa gaa aag aaa gaa gag aaa atc gta acc gcg aca aag aag     554
Phe Glu Glu Glu Lys Lys Glu Glu Lys Ile Val Thr Ala Thr Lys Lys
                 130                 135                 140 ggt gca gcg gtg cta gat cag tgg att cct gat gag ata aag agt cag     602
Gly Ala Ala Val Leu Asp Gln Trp Ile Pro Asp Glu Ile Lys Ser Gln
                     145                 150                 155 tac cat gtt cta caa agg ggt gat gat gtt tat gat gct atc tta aat     650
Tyr His Val Leu Gln Arg Gly Asp Asp Val Tyr Asp Ala Ile Leu Asn
         160                 165                 170 cag aca aat gtc agg gat aat aat aac aag ttc ttt gtc cta caa gtc     698
Gln Thr Asn Val Arg Asp Asn Asn Asn Lys Phe Phe Val Leu Gln Val
175                 180                 185                 190 cta gag tcg gat agt aaa aag aca tac atg gtt tac act aga tgg gga     746
Leu Glu Ser Asp Ser Lys Lys Thr Tyr Met Val Tyr Thr Arg Trp Gly
             195                 200                 205 aga gtt ggt gtg aaa gga caa agt aag cta gat ggg cct tat gac tca     794
Arg Val Gly Val Lys Gly Gln Ser Lys Leu Asp Gly Pro Tyr Asp Ser
                 210                 215                 220 tgg gat cgt gcg ata gag ata ttt acc aat aag ttc aat gac aag aca     842
Trp Asp Arg Ala Ile Glu Ile Phe Thr Asn Lys Phe Asn Asp Lys Thr
                     225                 230                 235 aag aat tat tgg tct gac aga aag gag ttt atc cca cat ccc aag tcc     890
Lys Asn Tyr Trp Ser Asp Arg Lys Glu Phe Ile Pro His Pro Lys Ser
         240                 245                 250 tat aca tgg ctc gaa atg gat tac gga aaa gag gaa aat gat tca ccg     938
Tyr Thr Trp Leu Glu Met Asp Tyr Gly Lys Glu Glu Asn Asp Ser Pro
255                 260                 265                 270 gtc aat aat gat att ccg agt tca tct tcc gaa gtt aaa cct gaa caa     986
Val Asn Asn Asp Ile Pro Ser Ser Ser Ser Glu Val Lys Pro Glu Gln
             275                 280                 285 tca aaa cta gat act cgg gtt gcc aag ttc atc tct ctt ata tgt aat    1034
Ser Lys Leu Asp Thr Arg Val Ala Lys Phe Ile Ser Leu Ile Cys Asn
                 290                 295                 300 gtc agc atg atg gca cag cat atg atg gaa ata gga tat aac gct aac    1082
Val Ser Met Met Ala Gln His Met Met Glu Ile Gly Tyr Asn Ala Asn
                     305                 310                 315 aaa ttg cca ctc ggc aag ata agc aag tcc aca att tca aag ggt tat    1130
Lys Leu Pro Leu Gly Lys Ile Ser Lys Ser Thr Ile Ser Lys Gly Tyr
         320                 325                 330 gaa gtg ctg aag aga ata tcg gag gtg att gac cgg tat gat aga acg    1178
Glu Val Leu Lys Arg Ile Ser Glu Val Ile Asp Arg Tyr Asp Arg Thr
335                 340                 345                 350 agg ctt gag gaa ctg agt gga gag ttc tac aca gtg ata cct cat gat    1226
Arg Leu Glu Glu Leu Ser Gly Glu Phe Tyr Thr Val Ile Pro His Asp
             355                 360                 365 ttt ggt ttt aag aaa atg agt cag ttt gtt ata gac act cct caa aag    1274
Phe Gly Phe Lys Lys Met Ser Gln Phe Val Ile Asp Thr Pro Gln Lys
```

```
                    370             375             380
ttg aaa cag aaa att gaa atg gtt gaa gca tta ggt gaa att gaa ctc    1322
Leu Lys Gln Lys Ile Glu Met Val Glu Ala Leu Gly Glu Ile Glu Leu
        385                 390                 395 gca aca aag ttg ttg tcc gtc gac ccg gga ttg cag gat gat cct tta    1370
Ala Thr Lys Leu Leu Ser Val Asp Pro Gly Leu Gln Asp Asp Pro Leu
400                 405                 410 tat tat cac tac cag caa ctt aat tgt ggt ttg acg cca gta gga aat    1418
Tyr Tyr His Tyr Gln Gln Leu Asn Cys Gly Leu Thr Pro Val Gly Asn
415                 420                 425                 430 gat tca gag gag ttc tct atg gtt gct aat tac atg gag aac act cat    1466
Asp Ser Glu Glu Phe Ser Met Val Ala Asn Tyr Met Glu Asn Thr His
                435                 440                 445 gca aag acg cat tcg gga tat acg gtt gag att gcc caa cta ttt aga    1514
Ala Lys Thr His Ser Gly Tyr Thr Val Glu Ile Ala Gln Leu Phe Arg
        450                 455                 460 gct tcg aga gct gtt gaa gct gat cga ttc caa cag ttt tca agt tcg    1562
Ala Ser Arg Ala Val Glu Ala Asp Arg Phe Gln Gln Phe Ser Ser Ser
    465                 470                 475 aag aac agg atg cta ctc tgg cac ggt tca cgt ctc act aac tgg gct    1610
Lys Asn Arg Met Leu Leu Trp His Gly Ser Arg Leu Thr Asn Trp Ala
480                 485                 490 ggt att tta tct caa ggt ctg cga ata gct cct cct gaa gcg cct gta    1658
Gly Ile Leu Ser Gln Gly Leu Arg Ile Ala Pro Pro Glu Ala Pro Val
495                 500                 505                 510 act ggt tac atg ttt gga aaa ggg gtt tac ttt gcg gat atg ttc tcc    1706
Thr Gly Tyr Met Phe Gly Lys Gly Val Tyr Phe Ala Asp Met Phe Ser
                515                 520                 525 aag agt gcg aac tat tgc tat gcc aac act ggc gct aat gat ggc gtt    1754
Lys Ser Ala Asn Tyr Cys Tyr Ala Asn Thr Gly Ala Asn Asp Gly Val
        530                 535                 540 ctg ctc ctc tgc gag gtt gct ttg gga gac atg aat gaa ctt ctg tat    1802
Leu Leu Leu Cys Glu Val Ala Leu Gly Asp Met Asn Glu Leu Leu Tyr
    545                 550                 555 tca gat tat aac gcg gat aat cta ccc ccg gga aag cta agc aca aaa    1850
Ser Asp Tyr Asn Ala Asp Asn Leu Pro Pro Gly Lys Leu Ser Thr Lys
560                 565                 570 ggt gtg ggg aaa aca gca cca aac cca tca gag gct caa aca cta gaa    1898
Gly Val Gly Lys Thr Ala Pro Asn Pro Ser Glu Ala Gln Thr Leu Glu
575                 580                 585                 590 gac ggt gtt gtt gtt cca ctt ggc aaa cca gtg gaa cgt tca tgc tcc    1946
Asp Gly Val Val Val Pro Leu Gly Lys Pro Val Glu Arg Ser Cys Ser
                595                 600                 605 aag ggg atg ttg ttg tac aac gaa tat ata gtc tac aat gtg gaa caa    1994
Lys Gly Met Leu Leu Tyr Asn Glu Tyr Ile Val Tyr Asn Val Glu Gln
        610                 615                 620 atc aag atg cgt tat gtg atc caa gtc aaa ttc aac tac aag cac taa    2042
Ile Lys Met Arg Tyr Val Ile Gln Val Lys Phe Asn Tyr Lys His
    625                 630                 635 aacttatgta tattagcttt tgaacatcaa ctaattatcc aaaaatcagc gttttattgt    2102
atttctttca aactccttca tctctgattt tgcacggttc actcg                   2147

<210> SEQ ID NO 6
<211> LENGTH: 637
<212> TYPE: PRT
<213> ORGANISM: Arabidopsis thaliana

<400> SEQUENCE: 6

Met Ala Asn Lys Leu Lys Val Asp Glu Leu Arg Leu Lys Leu Ala Glu
1               5                   10                  15
```

```
Arg Gly Leu Ser Thr Thr Gly Val Lys Ala Val Leu Val Glu Arg Leu
            20                  25                  30

Glu Glu Ala Ile Ala Glu Asp Thr Lys Lys Glu Ser Lys Ser Lys
        35                  40                  45

Arg Lys Arg Asn Ser Ser Asn Asp Thr Tyr Glu Ser Asn Lys Leu Ile
50                  55                  60

Ala Ile Gly Glu Phe Arg Gly Met Ile Val Lys Glu Leu Arg Glu Glu
65                  70                  75                  80

Ala Ile Lys Arg Gly Leu Asp Thr Thr Gly Thr Lys Lys Asp Leu Leu
                85                  90                  95

Glu Arg Leu Cys Asn Asp Ala Asn Asn Val Ser Asn Ala Pro Val Lys
            100                 105                 110

Ser Ser Asn Gly Thr Asp Glu Ala Glu Asp Asn Asn Gly Phe Glu
            115                 120                 125

Glu Glu Lys Lys Glu Glu Lys Ile Val Thr Ala Thr Lys Lys Gly Ala
        130                 135                 140

Ala Val Leu Asp Gln Trp Ile Pro Asp Glu Ile Lys Ser Gln Tyr His
145                 150                 155                 160

Val Leu Gln Arg Gly Asp Asp Val Tyr Asp Ala Ile Leu Asn Gln Thr
                165                 170                 175

Asn Val Arg Asp Asn Asn Asn Lys Phe Phe Val Leu Gln Val Leu Glu
            180                 185                 190

Ser Asp Ser Lys Lys Thr Tyr Met Val Tyr Thr Arg Trp Gly Arg Val
        195                 200                 205

Gly Val Lys Gly Gln Ser Lys Leu Asp Gly Pro Tyr Asp Ser Trp Asp
210                 215                 220

Arg Ala Ile Glu Ile Phe Thr Asn Lys Phe Asn Asp Lys Thr Lys Asn
225                 230                 235                 240

Tyr Trp Ser Asp Arg Lys Glu Phe Ile Pro His Pro Lys Ser Tyr Thr
                245                 250                 255

Trp Leu Glu Met Asp Tyr Gly Lys Glu Glu Asn Asp Ser Pro Val Asn
            260                 265                 270

Asn Asp Ile Pro Ser Ser Ser Glu Val Lys Pro Glu Gln Ser Lys
        275                 280                 285

Leu Asp Thr Arg Val Ala Lys Phe Ile Ser Leu Ile Cys Asn Val Ser
        290                 295                 300

Met Met Ala Gln His Met Met Glu Ile Gly Tyr Asn Ala Asn Lys Leu
305                 310                 315                 320

Pro Leu Gly Lys Ile Ser Lys Ser Thr Ile Ser Lys Gly Tyr Glu Val
                325                 330                 335

Leu Lys Arg Ile Ser Glu Val Ile Asp Arg Tyr Asp Arg Thr Arg Leu
            340                 345                 350

Glu Glu Leu Ser Gly Glu Phe Tyr Thr Val Ile Pro His Asp Phe Gly
        355                 360                 365

Phe Lys Lys Met Ser Gln Phe Val Ile Asp Thr Pro Gln Lys Leu Lys
370                 375                 380

Gln Lys Ile Glu Met Val Glu Ala Leu Gly Glu Ile Glu Leu Ala Thr
385                 390                 395                 400

Lys Leu Leu Ser Val Asp Pro Gly Leu Gln Asp Asp Pro Leu Tyr Tyr
                405                 410                 415

His Tyr Gln Gln Leu Asn Cys Gly Leu Thr Pro Val Gly Asn Asp Ser
            420                 425                 430

Glu Glu Phe Ser Met Val Ala Asn Tyr Met Glu Asn Thr His Ala Lys
```

```
                435                 440                 445
Thr His Ser Gly Tyr Thr Val Glu Ile Ala Gln Leu Phe Arg Ala Ser
450                 455                 460

Arg Ala Val Glu Ala Asp Arg Phe Gln Gln Phe Ser Ser Ser Lys Asn
465                 470                 475                 480

Arg Met Leu Leu Trp His Gly Ser Arg Leu Thr Asn Trp Ala Gly Ile
                485                 490                 495

Leu Ser Gln Gly Leu Arg Ile Ala Pro Pro Glu Ala Pro Val Thr Gly
                500                 505                 510

Tyr Met Phe Gly Lys Gly Val Tyr Phe Ala Asp Met Phe Ser Lys Ser
                515                 520                 525

Ala Asn Tyr Cys Tyr Ala Asn Thr Gly Ala Asn Asp Gly Val Leu Leu
530                 535                 540

Leu Cys Glu Val Ala Leu Gly Asp Met Asn Glu Leu Leu Tyr Ser Asp
545                 550                 555                 560

Tyr Asn Ala Asp Asn Leu Pro Pro Gly Lys Leu Ser Thr Lys Gly Val
                565                 570                 575

Gly Lys Thr Ala Pro Asn Pro Ser Glu Ala Gln Thr Leu Glu Asp Gly
                580                 585                 590

Val Val Val Pro Leu Gly Lys Pro Val Glu Arg Ser Cys Ser Lys Gly
                595                 600                 605

Met Leu Leu Tyr Asn Glu Tyr Ile Val Tyr Asn Val Glu Gln Ile Lys
610                 615                 620

Met Arg Tyr Val Ile Gln Val Lys Phe Asn Tyr Lys His
625                 630                 635

<210> SEQ ID NO 7
<211> LENGTH: 16
<212> TYPE: PRT
<213> ORGANISM: Artificial sequence
<220> FEATURE:
<223> OTHER INFORMATION: A domain of non-conventional PARP proteins
<220> FEATURE:
<221> NAME/KEY: MISC_FEATURE
<222> LOCATION: (3)..(3)
<223> OTHER INFORMATION: Xaa represents any amino acid
<220> FEATURE:
<221> NAME/KEY: MISC_FEATURE
<222> LOCATION: (4)..(4)
<223> OTHER INFORMATION: Xaa represents any amino acid
<220> FEATURE:
<221> NAME/KEY: MISC_FEATURE
<222> LOCATION: (5)..(5)
<223> OTHER INFORMATION: Xaa represents any amino acid
<220> FEATURE:
<221> NAME/KEY: MISC_FEATURE
<222> LOCATION: (6)..(6)
<223> OTHER INFORMATION: Xaa represents any amino acid
<220> FEATURE:
<221> NAME/KEY: MISC_FEATURE
<222> LOCATION: (8)..(8)
<223> OTHER INFORMATION: Xaa represents any amino acid
<220> FEATURE:
<221> NAME/KEY: MISC_FEATURE
<222> LOCATION: (10)..(10)
<223> OTHER INFORMATION: Xaa represents any amino acid
<220> FEATURE:
<221> NAME/KEY: MISC_FEATURE
<222> LOCATION: (11)..(11)
<223> OTHER INFORMATION: Xaa represents any amino acid
<220> FEATURE:
<221> NAME/KEY: MISC_FEATURE
<222> LOCATION: (12)..(12)
<223> OTHER INFORMATION: Xaa represents any amino acid
<220> FEATURE:
<221> NAME/KEY: MISC_FEATURE
<222> LOCATION: (13)..(13)
```

```
<223> OTHER INFORMATION: Xaa represents any amino acid
<220> FEATURE:
<221> NAME/KEY: MISC_FEATURE
<222> LOCATION: (14)..(14)
<223> OTHER INFORMATION: Xaa represents any amino acid

<400> SEQUENCE: 7

Arg Gly Xaa Xaa Xaa Xaa Gly Xaa Lys Xaa Xaa Xaa Xaa Xaa Arg Leu
1               5                   10                  15

<210> SEQ ID NO 8
<211> LENGTH: 33
<212> TYPE: PRT
<213> ORGANISM: Artificial sequence
<220> FEATURE:
<223> OTHER INFORMATION: A1 domain of non-conventional PARP proteins
<220> FEATURE:
<221> NAME/KEY: MISC_FEATURE
<222> LOCATION: (1)..(1)
<223> OTHER INFORMATION: Xaa represents any amino acid
<220> FEATURE:
<221> NAME/KEY: MISC_FEATURE
<222> LOCATION: (3)..(3)
<223> OTHER INFORMATION: Xaa represents any amino acid
<220> FEATURE:
<221> NAME/KEY: MISC_FEATURE
<222> LOCATION: (5)..(5)
<223> OTHER INFORMATION: Xaa represents any amino acid
<220> FEATURE:
<221> NAME/KEY: MISC_FEATURE
<222> LOCATION: (6)..(6)
<223> OTHER INFORMATION: Xaa represents any amino acid
<220> FEATURE:
<221> NAME/KEY: MISC_FEATURE
<222> LOCATION: (7)..(7)
<223> OTHER INFORMATION: Xaa represents any amino acid
<220> FEATURE:
<221> NAME/KEY: MISC_FEATURE
<222> LOCATION: (9)..(9)
<223> OTHER INFORMATION: Xaa represents any amino acid
<220> FEATURE:
<221> NAME/KEY: MISC_FEATURE
<222> LOCATION: (10)..(10)
<223> OTHER INFORMATION: Xaa represents any amino acid
<220> FEATURE:
<221> NAME/KEY: MISC_FEATURE
<222> LOCATION: (12)..(12)
<223> OTHER INFORMATION: Xaa represents any amino acid
<220> FEATURE:
<221> NAME/KEY: MISC_FEATURE
<222> LOCATION: (13)..(13)
<223> OTHER INFORMATION: Xaa represents any amino acid
<220> FEATURE:
<221> NAME/KEY: MISC_FEATURE
<222> LOCATION: (17)..(17)
<223> OTHER INFORMATION: Xaa represents any amino acid
<220> FEATURE:
<221> NAME/KEY: MISC_FEATURE
<222> LOCATION: (18)..(18)
<223> OTHER INFORMATION: Xaa represents any amino acid
<220> FEATURE:
<221> NAME/KEY: MISC_FEATURE
<222> LOCATION: (19)..(19)
<223> OTHER INFORMATION: Xaa represents any amino acid
<220> FEATURE:
<221> NAME/KEY: MISC_FEATURE
<222> LOCATION: (23)..(23)
<223> OTHER INFORMATION: Xaa represents any amino acid
<220> FEATURE:
<221> NAME/KEY: MISC_FEATURE
<222> LOCATION: (24)..(24)
<223> OTHER INFORMATION: Xaa represents any amino acid
<220> FEATURE:
<221> NAME/KEY: MISC_FEATURE
<222> LOCATION: (27)..(27)
<223> OTHER INFORMATION: Xaa represents any amino acid
<220> FEATURE:
<221> NAME/KEY: MISC_FEATURE
```

-continued

```
<222> LOCATION: (30)..(30)
<223> OTHER INFORMATION: Xaa represents any amino acid
<220> FEATURE:
<221> NAME/KEY: MISC_FEATURE
<222> LOCATION: (31)..(31)
<223> OTHER INFORMATION: Xaa represents any amino acid

<400> SEQUENCE: 8

Xaa Leu Xaa Val Xaa Xaa Xaa Arg Xaa Xaa Leu Xaa Xaa Arg Gly Leu
1               5                   10                  15

Xaa Xaa Xaa Gly Val Lys Xaa Xaa Leu Val Xaa Arg Leu Xaa Xaa Ala
            20                  25                  30

Ile

<210> SEQ ID NO 9
<211> LENGTH: 30
<212> TYPE: PRT
<213> ORGANISM: Artificial sequence
<220> FEATURE:
<223> OTHER INFORMATION: A2 domain of non-conventional PARP protein
<220> FEATURE:
<221> NAME/KEY: MISC_FEATURE
<222> LOCATION: (3)..(3)
<223> OTHER INFORMATION: Xaa represents any amino acid
<220> FEATURE:
<221> NAME/KEY: MISC_FEATURE
<222> LOCATION: (4)..(4)
<223> OTHER INFORMATION: Xaa represents any amino acid
<220> FEATURE:
<221> NAME/KEY: MISC_FEATURE
<222> LOCATION: (5)..(5)
<223> OTHER INFORMATION: Xaa represents any amino acid
<220> FEATURE:
<221> NAME/KEY: MISC_FEATURE
<222> LOCATION: (8)..(8)
<223> OTHER INFORMATION: Xaa represents any amino acid
<220> FEATURE:
<221> NAME/KEY: MISC_FEATURE
<222> LOCATION: (9)..(9)
<223> OTHER INFORMATION: Xaa represents any amino acid
<220> FEATURE:
<221> NAME/KEY: MISC_FEATURE
<222> LOCATION: (10)..(10)
<223> OTHER INFORMATION: Xaa represents any amino acid
<220> FEATURE:
<221> NAME/KEY: MISC_FEATURE
<222> LOCATION: (12)..(12)
<223> OTHER INFORMATION: Xaa represents any amino acid
<220> FEATURE:
<221> NAME/KEY: MISC_FEATURE
<222> LOCATION: (13)..(13)
<223> OTHER INFORMATION: Xaa represents any amino acid
<220> FEATURE:
<221> NAME/KEY: MISC_FEATURE
<222> LOCATION: (16)..(16)
<223> OTHER INFORMATION: Xaa represents any amino acid
<220> FEATURE:
<221> NAME/KEY: MISC_FEATURE
<222> LOCATION: (17)..(17)
<223> OTHER INFORMATION: Xaa represents any amino acid
<220> FEATURE:
<221> NAME/KEY: MISC_FEATURE
<222> LOCATION: (18)..(18)
<223> OTHER INFORMATION: Xaa represents any amino acid
<220> FEATURE:
<221> NAME/KEY: MISC_FEATURE
<222> LOCATION: (19)..(19)
<223> OTHER INFORMATION: Xaa represents any amino acid
<220> FEATURE:
<221> NAME/KEY: MISC_FEATURE
<222> LOCATION: (21)..(21)
<223> OTHER INFORMATION: Xaa represents any amino acid
<220> FEATURE:
<221> NAME/KEY: MISC_FEATURE
<222> LOCATION: (25)..(25)
<223> OTHER INFORMATION: Xaa represents any amino acid
```

```
<220> FEATURE:
<221> NAME/KEY: MISC_FEATURE
<222> LOCATION: (26)..(26)
<223> OTHER INFORMATION: Xaa represents any amino acid
<220> FEATURE:
<221> NAME/KEY: MISC_FEATURE
<222> LOCATION: (29)..(29)
<223> OTHER INFORMATION: Xaa represents any amino acid
<220> FEATURE:
<221> NAME/KEY: MISC_FEATURE
<222> LOCATION: (30)..(30)
<223> OTHER INFORMATION: Xaa represents any amino acid

<400> SEQUENCE: 9

Gly Met Xaa Xaa Xaa Glu Leu Xaa Xaa Xaa Ala Xaa Xaa Arg Gly Xaa
 1               5                  10                  15

Xaa Xaa Xaa Gly Xaa Lys Lys Asp Xaa Xaa Arg Leu Xaa Xaa
            20                  25                  30

<210> SEQ ID NO 10
<211> LENGTH: 3212
<212> TYPE: DNA
<213> ORGANISM: Zea mays
<220> FEATURE:
<221> NAME/KEY: CDS
<222> LOCATION: (81)..(3020)
<223> OTHER INFORMATION:

<400> SEQUENCE: 10
gcttcctctg tcgtccggcc tccaactcca tcgaaggggc tagggagagg agggaacccg      60
aaccacagca ggccggcgca atg gcg gcg ccg cca aag gcg tgg aag gcg gag     113
                        Met Ala Ala Pro Pro Lys Ala Trp Lys Ala Glu
                          1               5                  10 tat gcc aag tct ggg cgg gcc tcg tgc aag tca tgc cgg tcc cct atc      161
Tyr Ala Lys Ser Gly Arg Ala Ser Cys Lys Ser Cys Arg Ser Pro Ile
         15                  20                  25 gcc aag gac cag ctc cgt ctt ggc aag atg gtt cag gcg tca cag ttc      209
Ala Lys Asp Gln Leu Arg Leu Gly Lys Met Val Gln Ala Ser Gln Phe
     30                  35                  40 gac ggc ttc atg ccg atg tgg aac cat gcc agg tgc atc ttc agc aag      257
Asp Gly Phe Met Pro Met Trp Asn His Ala Arg Cys Ile Phe Ser Lys
 45                  50                  55 aag aac cag ata aaa tcc gtt gac gat gtt gaa ggg ata gat gca ctt      305
Lys Asn Gln Ile Lys Ser Val Asp Asp Val Glu Gly Ile Asp Ala Leu
60                  65                  70                  75 aga tgg gat gat caa gag aag ata cga aac tac gtt ggg agt gcc tca      353
Arg Trp Asp Asp Gln Glu Lys Ile Arg Asn Tyr Val Gly Ser Ala Ser
                 80                  85                  90 gct ggt aca agt tct aca gct gct cct cct gag aaa tgt aca att gag      401
Ala Gly Thr Ser Ser Thr Ala Ala Pro Pro Glu Lys Cys Thr Ile Glu
             95                 100                 105 att gct cca tct gcc cgt act tca tgt aga cga tgc agt gaa aag att      449
Ile Ala Pro Ser Ala Arg Thr Ser Cys Arg Arg Cys Ser Glu Lys Ile
        110                 115                 120 aca aaa gga tcg gtc cgt ctt tca gct aag ctt gag agt gaa ggt ccc      497
Thr Lys Gly Ser Val Arg Leu Ser Ala Lys Leu Glu Ser Glu Gly Pro
    125                 130                 135 aag ggt ata cca tgg tat cat gcc aac tgt ttc ttt gag gta tcc ccg      545
Lys Gly Ile Pro Trp Tyr His Ala Asn Cys Phe Phe Glu Val Ser Pro
140                 145                 150                 155 tct gca act gtt gag aag ttc tca ggc tgg gat act ttg tcc gat gag      593
Ser Ala Thr Val Glu Lys Phe Ser Gly Trp Asp Thr Leu Ser Asp Glu
                160                 165                 170 gat aag aga acc atg ctc gat ctt gtt aaa aaa gat gtt ggc aac aat      641
```

```
                Asp Lys Arg Thr Met Leu Asp Leu Val Lys Lys Asp Val Gly Asn Asn
                            175                 180                 185 gaa caa aat aag ggt tcc aag cgc aag aaa agt gaa aat gat att gat        689
Glu Gln Asn Lys Gly Ser Lys Arg Lys Lys Ser Glu Asn Asp Ile Asp
            190                 195                 200 agc tac aaa tcc gcc agg tta gat gaa agt aca tct gaa ggt aca gtg        737
Ser Tyr Lys Ser Ala Arg Leu Asp Glu Ser Thr Ser Glu Gly Thr Val
        205                 210                 215 cga aac aaa ggg caa ctt gta gac cca cgt ggt tcc aat act agt tca        785
Arg Asn Lys Gly Gln Leu Val Asp Pro Arg Gly Ser Asn Thr Ser Ser
220                 225                 230                 235 gct gat atc caa cta aag ctt aag gag caa agt gac aca ctt tgg aag        833
Ala Asp Ile Gln Leu Lys Leu Lys Glu Gln Ser Asp Thr Leu Trp Lys
                240                 245                 250 tta aag gat gga ctt aag act cat gta tcg gct gct gaa tta agg gat        881
Leu Lys Asp Gly Leu Lys Thr His Val Ser Ala Ala Glu Leu Arg Asp
            255                 260                 265 atg ctt gag gct aat ggg cag gat aca tca gga cca gaa agg cac cta        929
Met Leu Glu Ala Asn Gly Gln Asp Thr Ser Gly Pro Glu Arg His Leu
        270                 275                 280 ttg gat cgc tgt gcg gat gga atg ata ttt gga gcg ctg ggt cct tgc        977
Leu Asp Arg Cys Ala Asp Gly Met Ile Phe Gly Ala Leu Gly Pro Cys
    285                 290                 295 cca gtc tgt gct aat ggc atg tac tat tat aat ggt cag tac caa tgc       1025
Pro Val Cys Ala Asn Gly Met Tyr Tyr Tyr Asn Gly Gln Tyr Gln Cys
300                 305                 310                 315 agt ggt aat gtg tca gag tgg tcc aag tgt aca tac tct gcc aca gaa       1073
Ser Gly Asn Val Ser Glu Trp Ser Lys Cys Thr Tyr Ser Ala Thr Glu
                320                 325                 330 cct gtc cgc gtt aag aag aag tgg caa att cca cat gga aca aag aat       1121
Pro Val Arg Val Lys Lys Lys Trp Gln Ile Pro His Gly Thr Lys Asn
            335                 340                 345 gat tac ctt atg aag tgg ttc aaa tct caa aag gtt aag aaa cca gag       1169
Asp Tyr Leu Met Lys Trp Phe Lys Ser Gln Lys Val Lys Lys Pro Glu
        350                 355                 360 agg gtt ctt cca cca atg tca cct gag aaa tct gga agt aaa gca act       1217
Arg Val Leu Pro Pro Met Ser Pro Glu Lys Ser Gly Ser Lys Ala Thr
    365                 370                 375 cag aga aca tca ttg ctg tct tct aaa ggg ttg gat aaa tta agg ttt       1265
Gln Arg Thr Ser Leu Leu Ser Ser Lys Gly Leu Asp Lys Leu Arg Phe
380                 385                 390                 395 tct gtt gta gga caa tca aaa gaa gca gca aat gag tgg att gag aag       1313
Ser Val Val Gly Gln Ser Lys Glu Ala Ala Asn Glu Trp Ile Glu Lys
                400                 405                 410 ctc aaa ctt gct ggt gcc aac ttc tat gcc agg gtt gtc aaa gat att       1361
Leu Lys Leu Ala Gly Ala Asn Phe Tyr Ala Arg Val Val Lys Asp Ile
            415                 420                 425 gat tgt tta att gca tgt ggt gag ctc gac aat gaa aat gct gaa gtc       1409
Asp Cys Leu Ile Ala Cys Gly Glu Leu Asp Asn Glu Asn Ala Glu Val
        430                 435                 440 agg aaa gca agg agg ctg aag ata cca att gta agg gag ggt tac att       1457
Arg Lys Ala Arg Arg Leu Lys Ile Pro Ile Val Arg Glu Gly Tyr Ile
    445                 450                 455 gga gaa tgt gtt aaa aag aac aaa atg ctg cca ttt gat ttg tat aaa       1505
Gly Glu Cys Val Lys Lys Asn Lys Met Leu Pro Phe Asp Leu Tyr Lys
460                 465                 470                 475 cta gag aat gcc tta gag tcc tca aaa ggc agt act gtc act gtt aaa       1553
Leu Glu Asn Ala Leu Glu Ser Ser Lys Gly Ser Thr Val Thr Val Lys
                480                 485                 490 gtt aag ggc cga agt gct gtt cat gag tcc tct ggt ttg caa gat act       1601
```

```
                Val Lys Gly Arg Ser Ala Val His Glu Ser Ser Gly Leu Gln Asp Thr
                            495                 500                 505 gct cac att ctt gaa gat ggg aaa agc ata tac aat gca acc tta aac        1649
Ala His Ile Leu Glu Asp Gly Lys Ser Ile Tyr Asn Ala Thr Leu Asn
            510                 515                 520 atg tct gac ctg gca cta ggt gtg aac agc tac tat gta ctc cag atc        1697
Met Ser Asp Leu Ala Leu Gly Val Asn Ser Tyr Tyr Val Leu Gln Ile
        525                 530                 535 att gaa cag gat gat ggg tct gag tgc tac gta ttt cgt aag tgg gga        1745
Ile Glu Gln Asp Asp Gly Ser Glu Cys Tyr Val Phe Arg Lys Trp Gly
540                 545                 550                 555 cgg gtt ggg agt gag aaa att gga ggg caa aaa ctg gag gag atg tca        1793
Arg Val Gly Ser Glu Lys Ile Gly Gly Gln Lys Leu Glu Glu Met Ser
            560                 565                 570 aaa act gag gca atc aag gaa ttc aaa aga tta ttt ctt gag aag act        1841
Lys Thr Glu Ala Ile Lys Glu Phe Lys Arg Leu Phe Leu Glu Lys Thr
        575                 580                 585 gga aac tca tgg gaa gct tgg gaa tgt aaa acc aat ttt cgg aag cag        1889
Gly Asn Ser Trp Glu Ala Trp Glu Cys Lys Thr Asn Phe Arg Lys Gln
            590                 595                 600 cct ggg aga ttt tac cca ctt gat gtt gat tat ggt gtt aag aaa gca        1937
Pro Gly Arg Phe Tyr Pro Leu Asp Val Asp Tyr Gly Val Lys Lys Ala
        605                 610                 615 cca aaa cgg aaa gat atc agt gaa atg aaa agt tct ctt gct cct caa        1985
Pro Lys Arg Lys Asp Ile Ser Glu Met Lys Ser Ser Leu Ala Pro Gln
620                 625                 630                 635 ttg cta gaa ctc atg aag atg ctt ttc aat gtg gag aca tat aga gct        2033
Leu Leu Glu Leu Met Lys Met Leu Phe Asn Val Glu Thr Tyr Arg Ala
            640                 645                 650 gct atg atg gaa ttt gaa att aat atg tca gaa atg cct ctt ggg aag        2081
Ala Met Met Glu Phe Glu Ile Asn Met Ser Glu Met Pro Leu Gly Lys
        655                 660                 665 cta agc aag gaa aat att gag aaa gga ttt gaa gca tta act gag ata        2129
Leu Ser Lys Glu Asn Ile Glu Lys Gly Phe Glu Ala Leu Thr Glu Ile
            670                 675                 680 cag aat tta ttg aag gac acc gct gat caa gca ctg gct gtt aga gaa        2177
Gln Asn Leu Leu Lys Asp Thr Ala Asp Gln Ala Leu Ala Val Arg Glu
        685                 690                 695 agc tta att gtt gct gcg agc aat cgc ttt ttc act ctt atc cct tct        2225
Ser Leu Ile Val Ala Ala Ser Asn Arg Phe Phe Thr Leu Ile Pro Ser
700                 705                 710                 715 att cat cct cat att ata cgg gat gag gat gat ttg atg atc aaa gcg        2273
Ile His Pro His Ile Ile Arg Asp Glu Asp Asp Leu Met Ile Lys Ala
            720                 725                 730 aaa atg ctt gaa gct ctg cag gat att gaa att gct tca aag ata gtt        2321
Lys Met Leu Glu Ala Leu Gln Asp Ile Glu Ile Ala Ser Lys Ile Val
        735                 740                 745 ggc ttc gat agc gac agt gat gaa tct ctt gat gat aaa tat atg aaa        2369
Gly Phe Asp Ser Asp Ser Asp Glu Ser Leu Asp Asp Lys Tyr Met Lys
            750                 755                 760 ctt cac tgt gac atc acc ccg ctg gct cac gat agt gaa gat tac aag        2417
Leu His Cys Asp Ile Thr Pro Leu Ala His Asp Ser Glu Asp Tyr Lys
        765                 770                 775 tta att gag cag tat ctc ctc aac aca cat gct cct act cac aag gac        2465
Leu Ile Glu Gln Tyr Leu Leu Asn Thr His Ala Pro Thr His Lys Asp
780                 785                 790                 795 tgg tcg ctg gaa ctg gag gaa gtt ttt tca ctt gat cga gat gga gaa        2513
Trp Ser Leu Glu Leu Glu Glu Val Phe Ser Leu Asp Arg Asp Gly Glu
            800                 805                 810 ctt aat aag tac tca aga tat aaa aat aat ctg cat aac aag atg cta        2561
```

```
Leu Asn Lys Tyr Ser Arg Tyr Lys Asn Asn Leu His Asn Lys Met Leu
             815                 820                 825 tta tgg cac ggt tca agg ttg acg aat ttt gtg gga att ctt agt caa      2609
Leu Trp His Gly Ser Arg Leu Thr Asn Phe Val Gly Ile Leu Ser Gln
         830                 835                 840 ggg cta aga att gca cct cct gag gca cct gtt act ggc tat atg ttc      2657
Gly Leu Arg Ile Ala Pro Pro Glu Ala Pro Val Thr Gly Tyr Met Phe
845                 850                 855 ggc aaa ggc ctc tac ttt gca gat cta gta agc aag agc gca caa tac      2705
Gly Lys Gly Leu Tyr Phe Ala Asp Leu Val Ser Lys Ser Ala Gln Tyr
860                 865                 870                 875 tgt tat gtg gat agg aat aat cct gta ggt ttg atg ctt ctt tct gag      2753
Cys Tyr Val Asp Arg Asn Asn Pro Val Gly Leu Met Leu Leu Ser Glu
                880                 885                 890 gtt gct tta gga gac atg tat gaa cta aag aaa gcc acg tcc atg gac      2801
Val Ala Leu Gly Asp Met Tyr Glu Leu Lys Lys Ala Thr Ser Met Asp
            895                 900                 905 aaa cct cca aga ggg aag cat tcg acc aag gga tta ggc aaa acc gtg      2849
Lys Pro Pro Arg Gly Lys His Ser Thr Lys Gly Leu Gly Lys Thr Val
910                 915                 920 cca ctg gag tca gag ttt gtg aag tgg agg gat gat gtc gta gtt ccc      2897
Pro Leu Glu Ser Glu Phe Val Lys Trp Arg Asp Asp Val Val Val Pro
925                 930                 935 tgc ggc aag ccg gtg cca tca tca att agg agc tct gaa ctc atg tac      2945
Cys Gly Lys Pro Val Pro Ser Ser Ile Arg Ser Ser Glu Leu Met Tyr
940                 945                 950                 955 aat gag tac atc gtc tac aac aca tcc cag gtg aag atg cag ttc ttg      2993
Asn Glu Tyr Ile Val Tyr Asn Thr Ser Gln Val Lys Met Gln Phe Leu
                960                 965                 970 ctg aag gtg cgt ttc cat cac aag agg tagctgggag actaggcaag            3040
Leu Lys Val Arg Phe His His Lys Arg
                975                 980 tagagttgga aggtagagaa gcagagttag gcgatgcctc ttttggtatt attagtaagc    3100
ctggcatgta tttatgggtg ctcgcgcttg atccattttg gtaagtgttg cttgggcatc    3160
agcgcgaata gcaccaatca cacactttta cctaatgacg ttttactgta ta            3212

<210> SEQ ID NO 11
<211> LENGTH: 980
<212> TYPE: PRT
<213> ORGANISM: Zea mays

<400> SEQUENCE: 11

Met Ala Ala Pro Pro Lys Ala Trp Lys Ala Glu Tyr Ala Lys Ser Gly
1               5                   10                  15

Arg Ala Ser Cys Lys Ser Cys Arg Ser Pro Ile Ala Lys Asp Gln Leu
            20                  25                  30

Arg Leu Gly Lys Met Val Gln Ala Ser Gln Phe Asp Gly Phe Met Pro
        35                  40                  45

Met Trp Asn His Ala Arg Cys Ile Phe Ser Lys Lys Asn Gln Ile Lys
    50                  55                  60

Ser Val Asp Asp Val Glu Gly Ile Asp Ala Leu Arg Trp Asp Asp Gln
65                  70                  75                  80

Glu Lys Ile Arg Asn Tyr Val Gly Ser Ala Ser Ala Gly Thr Ser Ser
                85                  90                  95

Thr Ala Ala Pro Pro Glu Lys Cys Thr Ile Glu Ile Ala Pro Ser Ala
            100                 105                 110

Arg Thr Ser Cys Arg Arg Cys Ser Glu Lys Ile Thr Lys Gly Ser Val
        115                 120                 125
```

-continued

```
Arg Leu Ser Ala Lys Leu Glu Ser Glu Gly Pro Lys Gly Ile Pro Trp
    130                 135                 140

Tyr His Ala Asn Cys Phe Phe Glu Val Ser Pro Ser Ala Thr Val Glu
145                 150                 155                 160

Lys Phe Ser Gly Trp Asp Thr Leu Ser Asp Glu Asp Lys Arg Thr Met
                165                 170                 175

Leu Asp Leu Val Lys Lys Asp Val Gly Asn Asn Glu Gln Asn Lys Gly
            180                 185                 190

Ser Lys Arg Lys Lys Ser Glu Asn Asp Ile Asp Ser Tyr Lys Ser Ala
        195                 200                 205

Arg Leu Asp Glu Ser Thr Ser Glu Gly Thr Val Arg Asn Lys Gly Gln
    210                 215                 220

Leu Val Asp Pro Arg Gly Ser Asn Thr Ser Ser Ala Asp Ile Gln Leu
225                 230                 235                 240

Lys Leu Lys Glu Gln Ser Asp Thr Leu Trp Lys Leu Lys Asp Gly Leu
                245                 250                 255

Lys Thr His Val Ser Ala Ala Glu Leu Arg Asp Met Leu Glu Ala Asn
            260                 265                 270

Gly Gln Asp Thr Ser Gly Pro Glu Arg His Leu Leu Asp Arg Cys Ala
        275                 280                 285

Asp Gly Met Ile Phe Gly Ala Leu Gly Pro Cys Pro Val Cys Ala Asn
    290                 295                 300

Gly Met Tyr Tyr Tyr Asn Gly Gln Tyr Gln Cys Ser Gly Asn Val Ser
305                 310                 315                 320

Glu Trp Ser Lys Cys Thr Tyr Ser Ala Thr Glu Pro Val Arg Val Lys
                325                 330                 335

Lys Lys Trp Gln Ile Pro His Gly Thr Lys Asn Asp Tyr Leu Met Lys
            340                 345                 350

Trp Phe Lys Ser Gln Lys Val Lys Lys Pro Glu Arg Val Leu Pro Pro
        355                 360                 365

Met Ser Pro Glu Lys Ser Gly Ser Lys Ala Thr Gln Arg Thr Ser Leu
    370                 375                 380

Leu Ser Ser Lys Gly Leu Asp Lys Leu Arg Phe Ser Val Val Gly Gln
385                 390                 395                 400

Ser Lys Glu Ala Ala Asn Glu Trp Ile Glu Lys Leu Lys Leu Ala Gly
                405                 410                 415

Ala Asn Phe Tyr Ala Arg Val Val Lys Asp Ile Asp Cys Leu Ile Ala
            420                 425                 430

Cys Gly Glu Leu Asp Asn Glu Asn Ala Glu Val Arg Lys Ala Arg Arg
        435                 440                 445

Leu Lys Ile Pro Ile Val Arg Glu Gly Tyr Ile Gly Glu Cys Val Lys
    450                 455                 460

Lys Asn Lys Met Leu Pro Phe Asp Leu Tyr Lys Leu Glu Asn Ala Leu
465                 470                 475                 480

Glu Ser Ser Lys Gly Ser Thr Val Thr Val Lys Val Lys Gly Arg Ser
                485                 490                 495

Ala Val His Glu Ser Ser Gly Leu Gln Asp Thr Ala His Ile Leu Glu
            500                 505                 510

Asp Gly Lys Ser Ile Tyr Asn Ala Thr Leu Asn Met Ser Asp Leu Ala
        515                 520                 525

Leu Gly Val Asn Ser Tyr Tyr Val Leu Gln Ile Ile Glu Gln Asp Asp
    530                 535                 540

Gly Ser Glu Cys Tyr Val Phe Arg Lys Trp Gly Arg Val Gly Ser Glu
```

-continued

```
        545                 550                 555                 560
Lys Ile Gly Gly Gln Lys Leu Glu Glu Met Ser Lys Thr Glu Ala Ile
                    565                 570                 575
Lys Glu Phe Lys Arg Leu Phe Leu Glu Lys Thr Gly Asn Ser Trp Glu
                580                 585                 590
Ala Trp Glu Cys Lys Thr Asn Phe Arg Lys Gln Pro Gly Arg Phe Tyr
            595                 600                 605
Pro Leu Asp Val Asp Tyr Gly Val Lys Ala Pro Lys Arg Lys Asp
        610                 615                 620
Ile Ser Glu Met Lys Ser Ser Leu Ala Pro Gln Leu Leu Glu Leu Met
625                 630                 635                 640
Lys Met Leu Phe Asn Val Glu Thr Tyr Arg Ala Ala Met Met Glu Phe
                645                 650                 655
Glu Ile Asn Met Ser Glu Met Pro Leu Gly Lys Leu Ser Lys Glu Asn
                660                 665                 670
Ile Glu Lys Gly Phe Glu Ala Leu Thr Glu Ile Gln Asn Leu Leu Lys
            675                 680                 685
Asp Thr Ala Asp Gln Ala Leu Ala Val Arg Glu Ser Leu Ile Val Ala
        690                 695                 700
Ala Ser Asn Arg Phe Phe Thr Leu Ile Pro Ser Ile His Pro His Ile
705                 710                 715                 720
Ile Arg Asp Glu Asp Asp Leu Met Ile Lys Ala Lys Met Leu Glu Ala
                725                 730                 735
Leu Gln Asp Ile Glu Ile Ala Ser Lys Ile Val Gly Phe Asp Ser Asp
                740                 745                 750
Ser Asp Glu Ser Leu Asp Asp Lys Tyr Met Lys Leu His Cys Asp Ile
            755                 760                 765
Thr Pro Leu Ala His Asp Ser Glu Asp Tyr Lys Leu Ile Glu Gln Tyr
        770                 775                 780
Leu Leu Asn Thr His Ala Pro Thr His Lys Asp Trp Ser Leu Glu Leu
785                 790                 795                 800
Glu Glu Val Phe Ser Leu Asp Arg Asp Gly Glu Leu Asn Lys Tyr Ser
                805                 810                 815
Arg Tyr Lys Asn Asn Leu His Asn Lys Met Leu Leu Trp His Gly Ser
                820                 825                 830
Arg Leu Thr Asn Phe Val Gly Ile Leu Ser Gln Gly Leu Arg Ile Ala
            835                 840                 845
Pro Pro Glu Ala Pro Val Thr Gly Tyr Met Phe Gly Lys Gly Leu Tyr
        850                 855                 860
Phe Ala Asp Leu Val Ser Lys Ser Ala Gln Tyr Cys Tyr Val Asp Arg
865                 870                 875                 880
Asn Asn Pro Val Gly Leu Met Leu Ser Glu Val Ala Leu Gly Asp
                885                 890                 895
Met Tyr Glu Leu Lys Lys Ala Thr Ser Met Asp Lys Pro Pro Arg Gly
                900                 905                 910
Lys His Ser Thr Lys Gly Leu Gly Lys Thr Val Pro Leu Glu Ser Glu
            915                 920                 925
Phe Val Lys Trp Arg Asp Asp Val Val Val Pro Cys Gly Lys Pro Val
        930                 935                 940
Pro Ser Ser Ile Arg Ser Ser Glu Leu Met Tyr Asn Glu Tyr Ile Val
945                 950                 955                 960
Tyr Asn Thr Ser Gln Val Lys Met Gln Phe Leu Leu Lys Val Arg Phe
                965                 970                 975
```

```
His His Lys Arg
            980

<210> SEQ ID NO 12
<211> LENGTH: 1010
<212> TYPE: PRT
<213> ORGANISM: Artificial Sequence
<220> FEATURE:
<223> OTHER INFORMATION: fusion protein between APP N-terminal domain
      and GUS protein

<400> SEQUENCE: 12

Met Ala Asn Lys Leu Lys Val Asp Glu Leu Arg Leu Lys Leu Ala Glu
1               5                   10                  15

Arg Gly Leu Ser Thr Thr Gly Val Lys Ala Val Leu Val Glu Arg Leu
                20                  25                  30

Glu Glu Ala Ile Ala Glu Asp Thr Lys Lys Glu Ser Lys Ser Lys
            35                  40                  45

Arg Lys Arg Asn Ser Ser Asn Asp Thr Tyr Glu Ser Asn Lys Leu Ile
            50                  55                  60

Ala Ile Gly Glu Phe Arg Gly Met Ile Val Lys Glu Leu Arg Glu Glu
65                  70                  75                  80

Ala Ile Lys Arg Gly Leu Asp Thr Thr Gly Thr Lys Lys Asp Leu Leu
                85                  90                  95

Glu Arg Leu Cys Asn Asp Ala Asn Asn Val Ser Asn Ala Pro Val Lys
            100                 105                 110

Ser Ser Asn Gly Thr Asp Glu Ala Glu Asp Asp Asn Asn Gly Phe Glu
            115                 120                 125

Glu Glu Lys Lys Glu Glu Lys Ile Val Thr Ala Thr Lys Lys Gly Ala
            130                 135                 140

Ala Val Leu Asp Gln Trp Ile Pro Asp Glu Ile Lys Ser Gln Tyr His
145                 150                 155                 160

Val Leu Gln Arg Gly Asp Asp Val Tyr Asp Ala Ile Leu Asn Gln Thr
                165                 170                 175

Asn Val Arg Asp Asn Asn Asn Lys Phe Phe Val Leu Gln Val Leu Glu
            180                 185                 190

Ser Asp Ser Lys Lys Thr Tyr Met Val Tyr Thr Arg Trp Gly Arg Val
            195                 200                 205

Gly Val Lys Gly Gln Ser Lys Leu Asp Gly Pro Tyr Asp Ser Trp Asp
            210                 215                 220

Arg Ala Ile Glu Ile Phe Thr Asn Lys Phe Asn Asp Lys Thr Lys Asn
225                 230                 235                 240

Tyr Trp Ser Asp Arg Lys Glu Phe Ile Pro His Pro Lys Ser Tyr Thr
                245                 250                 255

Trp Leu Glu Met Asp Tyr Gly Lys Glu Glu Asn Asp Ser Pro Val Asn
            260                 265                 270

Asn Asp Ile Pro Ser Ser Ser Glu Val Lys Pro Glu Gln Ser Lys
            275                 280                 285

Leu Asp Thr Arg Val Ala Lys Phe Ile Ser Leu Ile Cys Asn Val Ser
            290                 295                 300

Met Met Ala Gln His Met Met Glu Ile Gly Tyr Asn Ala Asn Lys Leu
305                 310                 315                 320

Pro Leu Gly Lys Ile Ser Lys Ser Thr Ile Ser Lys Gly Tyr Glu Val
                325                 330                 335

Leu Lys Arg Ile Ser Glu Val Ile Asp Arg Tyr Asp Arg Thr Arg Leu
            340                 345                 350
```

-continued

```
Glu Glu Leu Ser Gly Glu Phe Tyr Thr Val Ile Pro His Asp Phe Gly
        355                 360                 365

Phe Lys Lys Met Ser Gln Phe Val Ile Asp Thr Pro Gln Lys Leu Lys
    370                 375                 380

Gln Lys Ile Glu Met Val Glu Ala Leu Gly Glu Ile Glu Leu Ala Thr
385                 390                 395                 400

Lys Leu Leu Ser Val Asp Pro Met Val Arg Pro Val Glu Thr Pro Thr
                405                 410                 415

Arg Glu Ile Lys Lys Leu Asp Gly Leu Trp Ala Phe Ser Leu Asp Arg
                420                 425                 430

Glu Asn Cys Gly Ile Asp Gln Arg Trp Trp Glu Ser Ala Leu Gln Glu
            435                 440                 445

Ser Arg Ala Ile Ala Val Pro Gly Ser Phe Asn Asp Gln Phe Ala Asp
        450                 455                 460

Ala Asp Ile Arg Asn Tyr Ala Gly Asn Val Trp Tyr Gln Arg Glu Val
465                 470                 475                 480

Phe Ile Pro Lys Gly Trp Ala Gly Gln Arg Ile Val Leu Arg Phe Asp
                485                 490                 495

Ala Val Thr His Tyr Gly Lys Val Trp Val Asn Asn Gln Glu Val Met
            500                 505                 510

Glu His Gln Gly Gly Tyr Thr Pro Phe Glu Ala Asp Val Thr Pro Tyr
        515                 520                 525

Val Ile Ala Gly Lys Ser Val Arg Ile Thr Val Cys Val Asn Asn Glu
    530                 535                 540

Leu Asn Trp Gln Thr Ile Pro Pro Gly Met Val Ile Thr Asp Glu Asn
545                 550                 555                 560

Gly Lys Lys Lys Gln Ser Tyr Phe His Asp Phe Phe Asn Tyr Ala Gly
                565                 570                 575

Ile His Arg Ser Val Met Leu Tyr Thr Thr Pro Asn Thr Trp Val Asp
            580                 585                 590

Asp Ile Thr Val Val Thr His Val Ala Gln Asp Cys Asn His Ala Ser
        595                 600                 605

Val Asp Trp Gln Val Val Ala Asn Gly Asp Val Ser Val Glu Leu Arg
    610                 615                 620

Asp Ala Asp Gln Gln Val Val Ala Thr Gly Gln Gly Thr Ser Gly Thr
625                 630                 635                 640

Leu Gln Val Val Asn Pro His Leu Trp Gln Pro Gly Glu Gly Tyr Leu
                645                 650                 655

Tyr Glu Leu Cys Val Thr Ala Lys Ser Gln Thr Glu Cys Asp Ile Tyr
            660                 665                 670

Pro Leu Arg Val Gly Ile Arg Ser Val Ala Val Lys Gly Glu Gln Phe
        675                 680                 685

Leu Ile Asn His Lys Pro Phe Tyr Phe Thr Gly Phe Gly Arg His Glu
    690                 695                 700

Asp Ala Asp Leu Arg Gly Lys Gly Phe Asp Asn Val Leu Met Val His
705                 710                 715                 720

Asp His Ala Leu Met Asp Trp Ile Gly Ala Asn Ser Tyr Arg Thr Ser
                725                 730                 735

His Tyr Pro Tyr Ala Glu Glu Met Leu Asp Trp Ala Asp Glu His Gly
            740                 745                 750

Ile Val Val Ile Asp Glu Thr Ala Ala Val Gly Phe Asn Leu Ser Leu
        755                 760                 765

Gly Ile Gly Phe Glu Ala Gly Asn Lys Pro Lys Glu Leu Tyr Ser Glu
    770                 775                 780
```

```
Glu Ala Val Asn Gly Glu Thr Gln Gln Ala His Leu Gln Ala Ile Lys
785                 790                 795                 800

Glu Leu Ile Ala Arg Asp Lys Asn His Pro Ser Val Val Met Trp Ser
            805                 810                 815

Ile Ala Asn Glu Pro Asp Thr Arg Pro Gln Gly Ala Arg Glu Tyr Phe
        820                 825                 830

Ala Pro Leu Ala Glu Ala Thr Arg Lys Leu Asp Pro Thr Arg Pro Ile
        835                 840                 845

Thr Cys Val Asn Val Met Phe Cys Asp Ala His Thr Asp Thr Ile Ser
    850                 855                 860

Asp Leu Phe Asp Val Leu Cys Leu Asn Arg Tyr Tyr Gly Trp Tyr Val
865                 870                 875                 880

Gln Ser Gly Asp Leu Glu Thr Ala Glu Lys Val Leu Glu Lys Glu Leu
                885                 890                 895

Leu Ala Trp Gln Glu Lys Leu His Gln Pro Ile Ile Ile Thr Glu Tyr
            900                 905                 910

Gly Val Asp Thr Leu Ala Gly Leu His Ser Met Tyr Thr Asp Met Trp
        915                 920                 925

Ser Glu Glu Tyr Gln Cys Ala Trp Leu Asp Met Tyr His Arg Val Phe
    930                 935                 940

Asp Arg Val Ser Ala Val Val Gly Glu Gln Val Trp Asn Phe Ala Asp
945                 950                 955                 960

Phe Ala Thr Ser Gln Gly Ile Leu Arg Val Gly Gly Asn Lys Lys Gly
                965                 970                 975

Ile Phe Thr Arg Asp Arg Lys Pro Lys Ser Ala Ala Phe Leu Leu Gln
            980                 985                 990

Lys Arg Trp Thr Gly Met Asn Phe  Gly Glu Lys Pro Gln  Gln Gly Gly
        995                 1000                1005

Lys Gln
    1010

<210> SEQ ID NO 13
<211> LENGTH: 25
<212> TYPE: DNA
<213> ORGANISM: Artificial sequence
<220> FEATURE:
<223> OTHER INFORMATION: degenerated PCR primer
<220> FEATURE:
<221> NAME/KEY: misc_feature
<222> LOCATION: (11)..(11)
<223> OTHER INFORMATION: n represents a,g,c or t
<220> FEATURE:
<221> NAME/KEY: misc_feature
<222> LOCATION: (23)..(23)
<223> OTHER INFORMATION: n represents a,g,c or t

<400> SEQUENCE: 13
ccgaattcgg ntayatgtty ggnaa                                            25

<210> SEQ ID NO 14
<211> LENGTH: 25
<212> TYPE: DNA
<213> ORGANISM: Artificial sequence
<220> FEATURE:
<223> OTHER INFORMATION: degenerated PCR primer
<220> FEATURE:
<221> NAME/KEY: misc_feature
<222> LOCATION: (11)..(11)
<223> OTHER INFORMATION: n represents a, g, c or t

<400> SEQUENCE: 14
```

-continued ccgaattcac natrtaytcr ttrta                                        25

<210> SEQ ID NO 15
<211> LENGTH: 25
<212> TYPE: DNA
<213> ORGANISM: Artificial sequence
<220> FEATURE:
<223> OTHER INFORMATION: oligonucleotide for use as PCR primer

<400> SEQUENCE: 15
gggaccatgt agtttatctt gacct                                        25

<210> SEQ ID NO 16
<211> LENGTH: 26
<212> TYPE: DNA
<213> ORGANISM: Artificial sequence
<220> FEATURE:
<223> OTHER INFORMATION: oligonucleotide for use in PCR

<400> SEQUENCE: 16
gacctcgtac cccaactctt ccccat                                       26

<210> SEQ ID NO 17
<211> LENGTH: 36
<212> TYPE: DNA
<213> ORGANISM: Artificial sequence
<220> FEATURE:
<223> OTHER INFORMATION: oligonucleotide for use in PCR

<400> SEQUENCE: 17
aagtcgacgc ggccgccaca cctagtgcca ggtcag                            36

<210> SEQ ID NO 18
<211> LENGTH: 24
<212> TYPE: DNA
<213> ORGANISM: Artificial sequence
<220> FEATURE:
<223> OTHER INFORMATION: oligonucleotide for use in PCR

<400> SEQUENCE: 18
atctcaattg tacatttctc agga                                         24

<210> SEQ ID NO 19
<211> LENGTH: 31
<212> TYPE: DNA
<213> ORGANISM: Artificial sequence
<220> FEATURE:
<223> OTHER INFORMATION: oligonucleotide for use in PCR

<400> SEQUENCE: 19
aggatcccat ggcgaacaag ctcaaagtga c                                 31

<210> SEQ ID NO 20
<211> LENGTH: 26
<212> TYPE: DNA
<213> ORGANISM: Artificial sequence
<220> FEATURE:
<223> OTHER INFORMATION: oligonucleotide for use in PCR

<400> SEQUENCE: 20
aggatcctta gtgcttgtag ttgaat                                       26

<210> SEQ ID NO 21
<211> LENGTH: 4947
<212> TYPE: DNA
<213> ORGANISM: Artificial sequence
<220> FEATURE:

```
<223> OTHER INFORMATION: APP promoter fusion with beta-glucuronidase
      gene
<220> FEATURE:
<221> NAME/KEY: promoter
<222> LOCATION: (1)..(1961)
<223> OTHER INFORMATION:
<220> FEATURE:
<221> NAME/KEY: misc_feature
<222> LOCATION: (1962)..(1964)
<223> OTHER INFORMATION: translation initiation codon
<220> FEATURE:
<221> NAME/KEY: misc_feature
<222> LOCATION: (3795)..(3795)
<223> OTHER INFORMATION: n represents a,c,g or t
<220> FEATURE:
<221> NAME/KEY: misc_feature
<222> LOCATION: (3796)..(3796)
<223> OTHER INFORMATION: n represents a,c,g or t
<220> FEATURE:
<221> NAME/KEY: misc_feature
<222> LOCATION: (3797)..(3797)
<223> OTHER INFORMATION: n represents a,c,g or t
<220> FEATURE:
<221> NAME/KEY: misc_feature
<222> LOCATION: (3798)..(3798)
<223> OTHER INFORMATION: n represents a,c,g or t
<220> FEATURE:
<221> NAME/KEY: misc_feature
<222> LOCATION: (3799)..(3799)
<223> OTHER INFORMATION: n represents a,c,g or t
<220> FEATURE:
<221> NAME/KEY: misc_feature
<222> LOCATION: (3800)..(3800)
<223> OTHER INFORMATION: n represents a,c,g or t

<400> SEQUENCE: 21
ctcgagatag tatattttt agttactatc attacataag tatattttaa aaaactaatt      60
atatgaatta tgtagctaac tagatagata atcgtataac caattcatgt tagtatagta    120
tagtttaagt atgtattttg ggattacaag tgtggttggc atcaagacaa ggatggtgat    180
agcctttctc tgtaatttgg tttaagaaaa gttttgcat tttatgtata aacgtgtttt     240
ttttttataa tttcaaattt caacaaaaaa caatttttt taataatgat tgaccactat    300
agacaattta aatgataaaa aaagggggga attttcaca atgttttgga gattagtcta    360 gatttttgt ccaaattttc cgattgtaag aattaagaag caatgaacat tgtgttaag     420 cttaatgatt tgtactcaca atatcttta aatttaaaat tgttaaccaa aatatccat    480 atattgtact tgtaatagaa atataaacta ttaaaaacaa cactttattc atataatata   540
agttaaaaca tatgttttt ttagtatgtt ctaatcacac ctattaaaaa agttgaagc    600 taaatgagcc aaaaagaaaa ataaagatag gggatgggga caggctgtaa tgttaggcgg    660
ttggtatatg aactgagaac atgtctgttg gttcggtcca tctacgccac tcaaccattt    720
ggctatgttt tcttttggc ttttgcatgt tctctctact tttcttcttt ggtcaaaatc     780
tctatctcgt cttttacatg gcttacccga atgttagttg tcatgtaaat ttggttatga    840
aaagatattt tatataaact ttatcgtata ttaatatcgt tatcatctaa ccattttta    900 aaactaaact agaaccatcc agtttacaa gagttttttt ttttttttc taactaaata     960 atatttgaag tgtacaatat taacaatata tgggccaaat aatagtggaa accaaatcgt   1020
tagtcccact ttatgatggg cctgttgatt cttatgtctt cttcgtaagt tgtgattatg   1080
cagattacgg gctaataaac atgcatgttt agttttact gtccaagtaa cgaaatttta    1140
tcttttgggt tgttggccca tttcatatat tccaaatgcc aaatccagcc cggctcgaca   1200
cagcactgct cggctcaaca ctcgtatgcg gttggtagcc acttaagacc ttggtttgat   1260
taacatgtta cgaataattt gtgtcccttt ttcttcaagg agactaatct cttttaataa   1320
```

```
aaaagaattg tgtcattagt caacacaagt cctataatcc gtttacgtaa tttgtatgca   1380
cgtccttgga aaagtgagta gtggcgtacg ttacagccaa aaactatttg tatattttct   1440
ttcgttaaac aaccagcaaa attttcagaa aaatgttctt aaattataaa ttagtagtac   1500
attttaaaac atagagattt tttgtttctt ttaatagaag agttaaacct atgtacaaaa   1560
tttcaactcc ttttcaaagt atttgcctgt tactagattt ttaacctttt ttttttatc    1620 tttcatgatt ttctattgct tgccatcatc aatggtagga aataaatact attttaaaaa   1680
ggtcaggggt ggatttaaga atcaatccaa aagtttgggg tcttttggag attaaaaagt   1740
tatatgggaa atatccacaa atatgaacga gaacttttgt caaaaaaatt taaaataatt   1800
tttcaaaaag ccctaaagct ttcaagggaa gccatcgatg aagaagaaaa cgaagaagaa   1860
gactcttcaa acgttcgcgc gaactcactt ctgacgaaaa ccatacttcc tcagtctcat   1920 tcccttttccg acgaactatt ctcctgaaga agaagacgaa aatggcgaac aagctcaaag   1980
tcgacatggt ccgtcctgta gaaacccaa cccgtgaaat caaaaaactc gacggcctgt    2040
gggcattcag tctggatcgc gaaaactgtg gaattgatca gcgttggtgg aaagcgcgt    2100 tacaagaaag ccgggcaatt gctgtgccag gcagttttaa cgatcagttc gccgatgcag   2160
atattcgtaa ttatgcgggc aacgtctggt atcagcgcga agtctttata ccgaaaggtt   2220
gggcaggcca gcgtatcgtg ctgcgtttcg atgcggtcac tcattacggc aaagtgtggg   2280
tcaataatca ggaagtgatg gagcatcagg gcggctatac gccatttgaa gccgatgtca   2340
cgccgtatgt tattgccggg aaaagtgtac gtatcaccgt ttgtgtgaac aacgaactga   2400
actggcagac tatcccgccg ggaatggtga ttaccgacga aaacggcaag aaaaagcagt   2460
cttacttcca tgatttcttt aactatgccg gaatccatcg cagcgtaatg ctctacacca   2520
cgccgaacac ctgggtggac gatatcaccg tggtgacgca tgtcgcgcaa gactgtaacc   2580
acgcgtctgt tgactggcag gtggtggcca atggtgatgt cagcgttgaa ctgcgtgatg   2640
cggatcaaca ggtggttgca actggacaag gcactagcgg gactttgcaa gtggtgaatc   2700
cgcacctctg gcaaccgggt gaaggttatc tctatgaact gtgcgtcaca gccaaaagcc   2760
agacagagtg tgatatctac ccgcttcgcg tcggcatccg gtcagtggca gtgaagggcg   2820
aacagttcct gattaaccac aaaccgttct actttactgg ctttggtcgt catgaagatg   2880
cggacttacg tggcaaagga ttcgataacg tgctgatggt gcacgaccac gcattaatgg   2940
actggattgg ggccaactcc taccgtacct cgcattaccc ttacgctgaa gagatgctcg   3000
actgggcaga tgaacatggc atcgtggtga ttgatgaaac tgctgctgtc ggctttaacc   3060
tctctttagg cattggtttc gaagcgggca acaagccgaa agaactgtac agcgaagagg   3120
cagtcaacgg ggaaactcag caagcgcact acaggcgat taaagagctg atagcgcgtg    3180
acaaaaacca cccaagcgtg gtgatgtgga gtattgccaa cgaaccggat acccgtccgc   3240
aagtgcacgg gaatatttcg ccactggcgg aagcaacgcg taaactcgac ccgacgcgtc   3300
cgatcacctg cgtcaatgta atgttctgcg acgctcacac cgataccatc agcgatctct   3360
ttgatgtgct gtgcctgaac cgttattacg atggtatgt ccaaagcggc gatttggaaa    3420
cggcagagaa ggtactggaa aaagaacttc tggcctggca ggagaaactg catcagccga   3480
ttatcatcac cgaatacggc gtggatacgt tagccgggct gcactcaatg tacaccgaca   3540
tgtggagtga agagtatcag tgtgcatggc tggatatgta tcaccgcgtc tttgatcgcg   3600
tcagcgccgt cgtcggtgaa caggtatgga atttcgccga ttttgcgacc tcgcaaggca   3660
tattgcgcgt tggcggtaac aagaaaggga tcttcactcg cgaccgcaaa ccgaagtcgg   3720
```

```
cggcttttct gctgcaaaaa cgctggactg gcatgaactt cggtgaaaaa ccgcagcagg    3780
gaggcaaaca atgannnnnn gaattggtcc tgctttaatg agatatgcga gacgcctatg    3840
atcgcatgat atttgctttc aattctgttg tgcacgttgt aaaaaacctg agcatgtgta    3900
gctcagatcc ttaccgccgg tttcggttca ttctaatgaa tatatcaccc gttactatcg    3960
tatttttatg aataatattc tccgttcaat ttactgattg taccctacta cttatatgta    4020
caatattaaa atgaaaacaa tatattgtgc tgaataggtt tatagcgaca tctatgatag    4080
agcgccacaa taacaaacaa ttgcgtttta ttattacaaa tccaatttta aaaaaagcgg    4140
cagaaccggt caaacctaaa agactgatta cataaatctt attcaaattt caaaaggccc    4200
caggggctag tatctacgac acaccgagcg gcgaactaat aacgttcact gaagggaact    4260
ccggttcccc gccggcgcgc atgggtgaga ttccttgaag ttgagtattg gccgtccgct    4320
ctaccgaaag ttacgggcac cattcaaccc ggtccagcac ggcggccggg taaccgactt    4380 gctgcccga gaattatgca gcattttttt ggtgtatgtg ggcccaaat gaagtgcagg     4440 tcaaaccttg acagtgacga caatcgttg ggcgggtcca gggcgaattt tgcgacaaca    4500
tgtcgaggct cagcaggact ctagaggatc cccgggtacc gagctcgaat tcactggccg    4560
tcgttttaca acgtcgtgac tgggaaaacc ctggcgttac ccaacttaat cgccttgcag    4620
cacatccccc tttcgccagc tggcgtaata gcgaagaggc ccgcaccgat cgcccttccc    4680
aacagttgcg cagcctgaat ggcgaatggc gcctgatgcg gtattttctc cttacgcatc    4740
tgtgcggtat ttcacaccgc atatggtgca ctctcagtac aatctgctct gatgccgcat    4800
agttaagcca gccccgacac ccgccaacac ccgctgacgc gccctgacgg gcttgtctgc    4860
tcccggcatc cgcttacaga caagctgtga ccgtctccgg gagctgcatg tgtcagaggt    4920
tttcaccgtc atcaccgaaa cgcgcga                                        4947
```